United States Patent [19]
Smith et al.

[11] Patent Number: 5,397,803
[45] Date of Patent: Mar. 14, 1995

[54] USE OF GLUTAMINE TO REDUCE RATE OF PATHOGENIC MICROORGANISM INFECTION

[75] Inventors: Robert J. Smith; Douglas Wilmore, both of Brookline, Mass.

[73] Assignee: Brigham and Women's Hospital, Boston, Mass.

[21] Appl. No.: 51,941

[22] Filed: Apr. 26, 1993

Related U.S. Application Data

[63] Continuation of Ser. No. 845,819, Mar. 9, 1992, abandoned, which is a continuation-in-part of Ser. No. 360,839, Jun. 2, 1989, abandoned, which is a continuation-in-part of Ser. No. 906,530, Sep. 12, 1986, Pat. No. 4,857,555, which is a continuation-in-part of Ser. No. 775,214, Sep. 12, 1985, abandoned.

[51] Int. Cl.⁶ .......................................... A61K 31/195
[52] U.S. Cl. ................................................... 514/563
[58] Field of Search .......................................... 514/563

[56] References Cited

U.S. PATENT DOCUMENTS

| | | | |
|---|---|---|---|
| 1,909,591 | 5/1933 | Nevin | 604/56 |
| 2,283,817 | 5/1942 | martin et al. | 167/55 |
| 2,662,046 | 12/1953 | Howe | 167/58 |
| 2,868,693 | 1/1959 | Shive et al. | 167/55 |
| 3,195,778 | 7/1965 | Coates | 222/80 |
| 3,217,711 | 11/1965 | Pecina et al. | 128/214 |
| 3,574,857 | 4/1971 | Cevallos | 424/319 |
| 3,701,666 | 10/1972 | Wimitz | 99/1 |
| 3,793,450 | 2/1974 | Schnell | 424/195 |
| 3,832,465 | 8/1974 | Ghadimi | 424/177 |
| 3,920,838 | 11/1975 | Flatt et al. | 424/319 |
| 3,950,529 | 4/1976 | Fischer et al. | 424/273 |
| 3,982,534 | 9/1976 | Buckman | 128/214 |
| 3,988,466 | 10/1976 | Takagi et al. | 424/274 |
| 4,200,095 | 4/1980 | Reti | 128/214 |
| 4,265,240 | 5/1981 | Jenkins | 128/214 |
| 4,334,535 | 6/1982 | Wilson et al. | 128/214 |
| 4,396,383 | 8/1983 | Hart | 604/56 |
| 4,414,202 | 11/1983 | Silvetti et al. | 424/147 |
| 4,439,448 | 3/1984 | Munakata et al. | 424/309 |
| 4,778,679 | 10/1988 | Silvetti et al. | 424/147 |
| 4,857,555 | 8/1989 | Smith et al. | 514/563 |
| 5,039,704 | 8/1991 | Smith et al. | 514/563 |

FOREIGN PATENT DOCUMENTS

| | | |
|---|---|---|
| 1285491 | 7/1991 | Canada . |
| 052296 | 10/1981 | European Pat. Off. . |
| 059694 | 9/1982 | European Pat. Off. . |
| 087750 | 3/1983 | European Pat. Off. . |
| 56-131554 | 10/1981 | Japan . |
| 59-130253 | 7/1984 | Japan . |
| 1125820 | 9/1968 | United Kingdom . |

OTHER PUBLICATIONS

Alberts, S. et al., "Complete Parenteral Nutrition in Rats With and Without a Synthetic Dipeptide (L–Alanyl–L–Glutamine) With Experimental Catabolism", *Akt. Ernarh.*:147–149 (1984) [English translation].

Alberts, S. et al., "Complete Parenteral Feeding With and Without a Synthetic Dipeptide (L–alanyl–L–glutamine) in Rats With Experimental Catabolism", *Chem. Abs.* 102:Abstr. 23355h (1985).

(List continued on next page.)

*Primary Examiner*—Richard L. Raymond
*Attorney, Agent, or Firm*—Sterne, Kessler, Goldstein & Fox

[57] ABSTRACT

The invention relates to a method for treating catabolic, gut-associated pathological processes including intestinal mucosal and pancreatic atrophy and enhanced gut permeability, impairment of host defenses and compromised immune function, and for promoting recovery from bone marrow transplantation in an animal, which comprises administering to an animal a therapeutically effective amount of glutamine or an analogue thereof.

5 Claims, 9 Drawing Sheets

OTHER PUBLICATIONS

Alverdy, J. C., "The GI Tract as an Immunogenic Organ", *Contemporary Surgery* 35(5-A):14–18 (1989).

Alverdy, John C. et al., "The Effect of Route of Nutrient Administration on the Secretory Immune System", *Current Surgery*, pp. 10–13 (Jan./Feb. 1985).

Alverdy, John C. et al., "The Effect of Parenteral Nutrition on Gastrointestinal Immunity—The Importance of Enteral Stimulation", *Ann. Surg.* 202 (6):681–684 (Dec. 1985).

Amberger, I. et al., "The Potential Parenteral Application of the Peptide L-Alanyl-L-Glutamine as a Nitrogen Source in Severe Catabolic States", *Hoppe-Seyler's Z. Physiol. Chem.* 364:1253–1254 (1983).

Andrassy, Richard et al., "Symposium: Nutrition for AIDS Patients", *Contemp. Surg.* 35:53–79 (Nov. 1989).

Aoki, Thomas T. et al., "Leucine Meal Increases Glutamine and Total Nitrogen Release from Forearm Muscle", *J. Clin. Invest.* 68:1522–1528 (Dec. 1981).

Askanazi, J. et al., "Muscle and Plasma Amino Acids after Injury", *Ann. Surg.* 191(4):465–472 (Apr. 1980).

Askanazi, J. et al., "Muscle and Plasma Amino Acids Following Injury—Influence of Intercurrent Infection", *Ann. Surg.* 192(1):78–85 (Jul. 1980).

Baskerville, A. et al., "Pathological Features of Glutaminase Toxicity", *Br. J. exp. Path.* 61:132–138 (1980).

Bergner, H. et al., "Influence of the Glutamic Acid Content of the Diet on the Catabolic Rate of Labeled Glutamic Acid in Rats: 1. Timecourse of the carbon-1-4-labeled carbon dioxide-excretion after labeling with carbon-14-labeled glutamic acid by intragastric infusion", *Biol. Abstr.* 79(10):Abstract 88557 (1985).

Bergström, J. et al., "Intracellular Free Amino Acid Concentration in Human Muscle Tissue", *J. App. Physiol.* 36(6):693–697 (Jun. 1974).

Cersosimo, E. et al., "Role of Glutamine in Adaptations in Nitrogen Metabolism during Fasting", *Am. J. Physiol.* 250:E622–E628 (1986).

Cheney, Carrie L. et al., "Body Composition Changes in Marrow Transplant Recipients Receiving Total Parenteral Nutrition", *Cancer* 59:1515–1519 (1987).

Chipponi, Jacques X. et al., "Deficiencies of Essential and Conditionally Essential Nutrients", *Am. J. Clin. Nutr.* 35:1112–1116 (May 1982).

Clowes, George H. A. et al., "Effects of Parenteral Alimentation on Amino Acid Metabolism in Septic Pateients", *Surgery* 88(4):531–543 (Oct. 1980).

Cunningham, Beth Ann et al., "Nutritional Considerations during Marrow Transplantation", *Nursing Clinics of North America* 18(3):585–596 (Sep. 1983).

Derr, R. F. et al., "Total Parenteral Nutrition: Improved Formula For Healing Rat Jejunal Anastomoses", *Bio. Abs.* 72(7):Abstr. 47176 (1981).

Derr, Robert F. et al., "Total Parenteral Nutrition: Improved Formula for Healing Rat Jejunal Anastomoses", *Nutrition Reports International* 23(4):749–753 (Apr. 1981).

Durschlag, Roberta P. et al., "Glutamine Production by Skeletal Muscle in Tissue Culture", *Federation Proceedings* 42:996 [Entry 4126] (1983).

Durschlag, Roberta P. et al., "Regulation of Glutamine Production by Skeletal Muscle Cells in Culture", *Am. J. Physiol.* 248:C442–C448 (1985).

Elia, Marinos et al., "Alanine and Glutamine Release from the Human Forearm: Effects of Glucose Administration", *Chem. Abs.* 103:Abstr. 102688t (1985).

Fürst, P. et al., "Influence of Amino Acid Supply on Nitrogen and Amino Acid Metabolism in Severe Trauma", *Act Chir. Scand. Suppl.* 494:136–138 (1979).

Gamble, James L., "Physiological Information Gained from Studies on the Life Raft Ration", *Harvey Lectures* 42:247–273 (1946–1947).

Hambleton, P. et al., "Clinical Biochemical Aspects of Glutaminase Toxicity in Rabbits and Rhesus Monkeys", *Br. J. exp. Path.* 61:208–216 (1980).

Hammarqvist, Folke et al., "Addition of Glutamine to Total Parenteral Nutrition after Elective Abdominal Surgery Spares Free Glutamine in Muscle, Counteracts the Fall in Muscle Protein Synthesis, and Improves Nitrogen Balance", *Ann. Surg.* 209(4):455–461 (Apr. 1989).

Hanson, Peter John et al., "Metabolism and Transport of Glutamine and Glucose in Vascularly Perfused Small Intestine Rat", *Biochem. J.* 166:509–519 (1977).

Harada, M. et al., "Changes in Biological Elements in Mouse Stress Ulcer and Effects of Drugs", *Folia Pharmacol. JPN* 69(6):322P (1973).

Heath, D. F. et al., "The Effects of the Stress Caused by Experimental Procedures on Alanine, Aspartate, Glutamate and Glutamine in Rat Liver", *Biochem. J.* 125:765–771 (1971).

Hong, Chang-Zern et al., "Metabolic Effects of Exhaustive Training of Athletes", *Biol. Abstr.* 78(9):Abstr. 70581 (1984).

(List continued on next page.)

OTHER PUBLICATIONS

Hughes, C. A. et al., "Speed of Change in Pancreatic Mass and in Intestinal Bacteriology of Parenterally Fed Ras", *Clinical Science* 59:329-336 (1980).

Ivanova, I. A. et al., "Comparative Study of Some Drugs on Different Models of Brain Hypoxia", *Biol. Abstr.* 80(4):Abstr. 34601 (1985).

Johnson, Daniel J. et al., "Branched Chain Amino Acid Uptake and Muscle Free Amino Acid Concentrations Predict Postoperative Muscle Nitrogen Balance", *Ann. Surg.* 204(5):513-523 (Nov. 1986).

Johnson, Daniel J. et al., "Glutamine Infusion Supports Plasma Amino Acid Metabolism during Simulated Stress", *Curr. Surg.* 43:31-34 (Jan.-Feb. 1986).

Johnson, Leonard R., "Regulation of Gastrointestinal Growth", chapter 10 of *Physiology of the Gastrointestinal Tract, 2nd ed.* (L. R. Johnson, ed.), Raven Press, New York (1987).

Johnson, Leonard R. et al., "Structural and Hormonal Alterations in the Gastrointestinal Tract of Parenterally Fed Rats", *Gastroenterology* 68(5):1177-1183 (1975).

Johnson, Leonard R. et al., "Effect of Long-Term Parenteral Feeding on Pancreatic Secretion and Serum Secretin", *Amer. J. Physiol.* 233:E524-E529 (1977).

Kapadia, C. Raja et al., "Maintenance of Skeletal Muscle Intracellular Glutamine during Standard Surgical Trauma", *J. of Parenteral and Enteral Nutrition* 9(5):583-589 (1985).

Kapadia, C. Raja et al., "Alterations in Glutamine Metabolism in Response to Operative Stress and Food Deprivation", *Surgical Forum* 33:19-21 (1982).

Korein, Julius, "Oral L-Glutamine Well Tolerated", *The New England Journal of Medicine* 301:1066 (Nov. 8, 1979).

Korein, Julius, "Treatment Questioned in Familial Spasmodic Torticollis", *Neurology* 27:899-900 (Sep. 1977).

Lenssen, Poly et al., "Parenteral Nutrition in Marrow Transplant Recipients after Discharge from the Hospital", *Exp. Hematol.* 11(10):974-981 (Nov. 1983).

Lenssen, Polly et al., "Intravenous Branched Chain Amino Acid Trial in Marrow Transplant Recipients", *J. of Parenteral and Enteral Nutrition* 11(2):112-118 (Mar.-/Apr. 1987).

Levine, Gary M. et al., "Role of Oral Intake in Maintenance of Gut Mass and Disaccharide Activity", *Gastroenterology* 67(5):975-982 (Nov. 1974).

Levine, Gary M. et al., "Small-Bowel Resection—Oral Intake Is the Stimulus for Hyperplasia", *Digestive Diseases* 21(7):542-546 (Jul. 1976).

Levintow, Leon et al., "The Role of Glutamine in Protein Biosynthesis in Tissue Culture", *J. Biol. Chem.* 227:929-941 (1957).

Longton, R. W. et al., "Initiation of Gingival Lesions during Amino Acid Stress", *BioReviews* 10:183 [Entry 498] (1973).

MacLennan, Peter A. et al., "A Positive Relationship between Protein Synthetic Rate and Intracellular Glutamine Concentration in Perfused Rat Skeletal Muscle", *FEBS l 215(1):187-191 (May 1987).*

MacLennan, Peter A. et al., "Inhibition of Protein Breakdown by Glutamine in Perfused Rat Skeletal Muscle", *FEBS* 237:133-136 (Sep. 1988).

Marliss, E. B. et al., "Muscle and Splanchinic Glutamine and Glutamate Metabolism in Postabsorptive and Starved Man", *J. Clin. Invest.* 50:814-817 (1971).

Menzies, Ian S., "Absorption of Intact Oligosaccharide in Health and Disease", *Biochem. Soc. Trans.* 550(2):1042-1047 (1974).

Milakofsky, Louis et al., "Rat Plasma Levels of Amino Acids and Related Compounds during Stress", *Life Sciences* 36:753-761 (1985).

Moyer, Mary Pat et al., "Effects of Gastrin, Glutamine, and Somatostatin on the In Vitro Growth of Normal and Malignant Human Gastric Mucosal Cells", *Chem. Abstr.* 104:Abstr. 219523x (1986).

Muhlacher, Ferdinand et al., "Effects of Glucocorticoids on Glutamine Metabolism in Skeletal Muscle", *Am. J. Physiol.* 247:E75-E83 (1984).

Newsholme, E. A. et al., "The Role of High Rates of Glycolysis and Glutamine Utilization in Rapidly Dividing Cells", *Bioscience Reports*:393-400 (1985).

O'Dwyer, S. T. et al., "5-Fluorouracil Toxicity on Small Intestinal Mucosa but not White Blood Cells is Decreased by Glutamine", *Clinical Research* 35(3):369A (1987).

Ohta, H. et al., "Effect of L-Glutamate, Injected into the Posterior Hypothatmus, on Blood Pressure and Heart Rate in Unanesthetized and Unrestrained Rats", *Neuropharmacology* 24(5):445-451 (1985).

(List continued on next page.)

OTHER PUBLICATIONS

Okabe, Susumu et al., "Inhibitory Effect of L-Glutamine on Gastric Irritation and Back Diffusion of Gastric Acid in Response to Aspirin in the Rat", *Digestive Disease* 20(7):626-631 (Jul. 1975).

Okabe, Susumu et al., "Effect of L-Glutamine on Indomethacin-Induced Gastric Lesions in the Rat", *Japan J. Pharmacol.* 24:169-171 (1974).

Okabe, Susumu et al., "Effects of L-Glutamine on Various Gasric Lesions in Rats and Guinea Pigs", *Digestion* 14:325-331 (1976).

*Physicians Desk Reference*—1972, pp. 705-707.

*Physicians Desk Reference*—1983, pp. 1418-1421.

*Physicians Desk Reference*—1987, pp. 1419-1422.

Pitts, Robert F., "Renal Production and Excretion of Ammonia", *Am. J. Med.* 36:720-742 (May 1964).

Richardson, C. T., "Gastric Ulcer", in:*Gastrointestinal Disease*, pp. 879-909, Sleisenger, M. H. et al., eds., W. B. Saunders Co. (1989).

Roth, E., "Changes of the Protein Metabolism in Cachexia and Catabolism", *Biol. Abstr.* 80(11):Abstr. 96470 (1985).

Roth, E. et al., "Biochemical Methods for the Determination of a Clinical Protein Catabolism", *Biol. Abstr.* 72(4):Abstr. 25963 (1980).

Roth, E. et al., "Metabolic Responses to Severe Infection and Sepsis", *Biol. Abstr.* 80(11):Abstr. 96352 (1985).

Schmidt Gerhard M. et al., "Parenteral Nitrition in Bone Marrow Transplant Recipients", *Exp. Hemat.* 8(4):506-511 (Apr. 1980).

Schrek, Robert et al., "Effect of Asparagine and Glutamine Deficiency on Normal and Leukemic Cells", *J. Natl. Cancer Inst.* 51:1103-1107 (1973).

Schwartau, M. et al., "An Experiemntal Animal Study of Chronic Lack of Thiamin: Alterations in Carbohydrate and Amino-Acid Metabolism at Rest and Under Strain", *Biol. Abstr.* 79(7):Abstr. 61030 (1985).

Schwartau, M. et al., "Tierexperimentelle Studie zum Chronischen Thiaminmangel. Veränderungen des Kohlenhydrat-und Aminosäurenstoffwechsels unter Ruhe— und Belastungsbedingungen", *Z. Ernaehrungswiss* 23:206-218 (1984).

Smith, Robert J. et al., "Tissue Specific Nutritional Regulation of Glutamine Metabolism", *Clinical Research* 34(2):393A (1986).

Smith, Robert J. et al., "Regulation of Glutamine Metabolism in Cultured Skeletal Muscle Cells", *Diabetes* 31:24A (1982).

Smith, Robert J. et al., "Mechanisms of Selective Alanine and Glutamine Release from Skeletal Muscle", *Diabetes* 33:Suppl., 2A (1984).

Smith, Robert J. et al., "Regulation of Glutamine Synthetase and Glutaminase Activities in Cultured Skeletal Muscle Cells", *J. Cell. Physiol.* 120:197-203 (1984).

Souba, Wiley W., "Glutamine Metabolism in Catabolic States: Role of the Intestinal Tract", *Thesis in Harvard Medical Library* (Jun. 1984).

Souba, Wiley W. et al., "Glucocorticoids Alter Amino Acid Metabolism in Visceral Organs", *Surgical Forum* 34:74-78 (1983).

Souba, Wiley W. et al., "Postoperative Alteration of Arteriovenous Exchange of Amino Acids Across the Gastrointestinal Tract", *Surgery* 94(2):342-350 (Aug. 1983).

Souba, Wiley W. et al., "Intestinal Consumption of Intravenously Administered Fuels", *J. of Parenteral and Enteral Nutrition* 9(1):18-22 (Jan./Feb. 1985).

Souba, Wiley W. et al., "Effects of Glucocorticoids on Glutamine Metabolism in Visceral Organs", *Metabolism* 34(5):450-456 (May 1985).

Souba, Wiley W. et al., "Gut-Liver Interaction During Accelerated Gluconeogenesis", *Arch Surg* 120:66-70 (Jan. 1985).

Stehle, P. et al., "Effect of Parenteral Glutamine Peptide Supplements on Muscle Glutamine Loss and Nitrogen Balance After Major Surgery", *Lancet* ii:231-233 (Feb. 4, 1989).

Szeluga, Debra J. et al., "Nutritional Support of Bone Marrow Transplant Recipients: A Prospective, Randomized Clinical Trial Compraring Total Parenteral Nutrition to an Enteral Feeding Program", *Cancer Research* 47:3309-3316 (Jun. 15, 1987).

Tischler, Marc E. et al., "Leucine Degradation and Release of Glutamine and Alanine by Adipose Tissue", *Biol. Abstr.* 71(3):Abstr. 14875 (1980).

Towne, Jonathan B. et al., "Mechanism of Hyperalimentation in the Suppression of Upper Gastrointestinal Secretions", *Am. J. Surg.* 126:714-716 (Dec. 1973).

(List continued on next page.)

OTHER PUBLICATIONS

Viallard, V. et al., "Effect of Glutamine Deprivation and Glutamate or Ammonium Chloride Addition on Growth Rate, Metabolism and Differentiation of Human Colon Cancer Cell-Line HT29", *Chem. Abstr.* 127504p (1986).

Vinnars, Eric et al., "Effect of Parenteral Nutrition on Intracellular Free Amino Acid Concentration", *J. of Parenteral and Enteral Nutrition* 4(2):184–187 (Mar.-/Apr. 1980).

Weisdorf, Sally A. et al., "Positive Effect of Prophylactic Total Parenteral Nutrition on Long-Term Outcome of Bone Marrow Transplantation", *Transplantation* 43(6):833–838 (1987).

Weisdorf, Sally A. et al., "Total Parenteral Nutrition in Bone Marrow Transplantation: A clinical Evaluation", *J. of Pediatric Gastroenterology and Nutrition*:95–100 (1984).

Wilmore, Douglas W. et al., "The Gut: A Central Organ After Surgical Stress", *Surgery* 104(5):917–923 (Nov. 1988).

Windmueller, Herbert G., "Glutamine Utilization by the Small Intestine", *Adv. Enzymol.* 53:201–237 (1982).

Wolfe, Bruce M. et al., "Substrate Interaction in Intravenous Feeding 13 Comparative Effects of Carbohydrate and Fat on Amino Acid Utilization in Fasting Man", *Ann. Surg.* 186(4):518–540 (Oct. 1977).

Zanello, M. et al., "Alterations in the Enzyme Profile in Intensive Care Patients Undergoing Total Parenteral Nutrition", *Biol. Abstr.* 70(8):Abstr. 52747 (1980).

Ziegler, Thomas R. et al., "Clinical and Metabolic Efficacy of Glutamine-Supplemented Parenteral Nutrition after Bone Marrow Transplantation", *Ann. Int. Med.* 116(10):821–828 (May 15, 1992).

USE OF GLUTAMINE TO REDUCE RATE OF PATHOGENIC MICROORGANISM INFECTION

STATEMENT AS TO RIGHTS TO INVENTIONS MADE UNDER FEDERALLY-SPONSORED RESEARCH AND DEVELOPMENT

This invention was funded by research grants from the National Institutes of Health, Trauma Center Grant No. GM29327-05, and the United States Department of the Army, Contract No. DAMD-17-81-C-1201, which provide to the United States Government certain rights in the invention.

CROSS REFERENCE TO RELATED APPLICATION

This is a continuation of Ser. No. 07/845,819, filed Mar. 9, 1992, (now abandoned), which is a continuation-in-part of application Ser. No. 07/360,839, filed Jun. 2, 1989, (now abandoned), which is continuation-in-part of application Ser. No. 06/906,530, filed Sep. 12, 1986 (issued as U.S. Pat. No. 4,857,555), which is a continuation-in-part of application Ser. No. 06/775,214, filed Sep. 12, 1985 (now abandoned).

BACKGROUND OF THE INVENTION

1. Field of the Invention

The present invention relates to a method for treating catabolic, gut-associated pathological processes including intestinal mucosal and pancreatic atrophy and other disorders associated with enhanced gut permeability, impairment of host defenses, and compromised immune function. The invention further relates to a method for promoting recovery in subjects undergoing bone marrow transplantation.

2. Description of the Background Art

Catabolic processes (dysfunctions) are those physiological conditions in which the degradation of an anatomical structure occurs. Such conditions typically affect not only skeletal muscle, but also the lining of the gut. Catabolic activity resulting in tissue damage frequently follows surgery, sepsis, burn injury, cancer chemotherapy, radiation therapy/injury, or glucocorticoid therapy, often in association with inadequate food intake. such injuries, diseases, and treatments also typically result in compromised immune function.

In patients undergoing bone marrow transplantation, for example, the radiation and/or chemotherapeutic regimens pre- and post-transplant, coupled with the frequent occurrence of graft-versus-host disease, produce both catabolic and serious nutritional consequences. Many factors contribute to a requirement for total parenteral nutrition (TPN) in these patients, including oral and esophageal mucositis, diarrhea, nausea, vomiting, xerostomia, and dysgeusia (Cunninhgam et al., *Nurs. Clin. N. Amer.*, 18:585–596 (1983); Cheney et al., *Cancer* 59:1515–1519 (1987)). Although TPN is believed to be necessary and beneficial in bone marrow transplant patients, trials with i.v. infusion of specialized formulas high in branched-chain amino acids (BCAA) during the first month after transplantation did not improve nitrogen balance (Lenssen et al., *J. Parent. Ent. Nutr.* 11:112–118 (1987)).

A catabolic response, damage to the gastrointestinal tract and compromised immune function brought on by the various causes listed above can be a major cause of death and disability. These clinical states are frequently associated with abnormal metabolism of the non-essential amino acid, glutamine (GLN). GLN can be synthesized to some extent by most tissues. Unlike most amino acids, GLN has two amine moieties: an alpha-amino group and an amide group. The presence of the amide group enables GLN to remove ammonia from the peripheral tissues of the body and transport nitrogen to visceral organs. In addition, it is common for tissues that remove GLN from the circulation to utilize the carbon skeleton for energy.

Glutaminase and glutamine synthetase are the two principal enzymes involved in the regulation of GLN metabolism. Glutaminase catalyzes the hydrolysis of GLN to glutamate and ammonia, while glutamine synthetase catalyzes the synthesis of GLN from glutamate and ammonia. While most tissues have both of these enzymes, usually one is more active than the other, depending on the particular tissue.

GLN synthesis and exportation occurs primarily in skeletal muscle and the brain. In turn, GLN is consumed by such replicating cells as fibroblasts, hemopoietic cells, lymphocytes, intestinal epithelium, and tumor cells. Characteristically, these cells possess high levels of glutaminase activity and low levels of intracellular GLN. This fact may have clinical significance for patients having large wounds, inflammation associated with infection, or a gastrointestinal dysfunction which precludes normal enteral feeding since the desirable proliferation of the cell types in these conditions may depend on the availability of sufficient levels of GLN.

In the gastrointestinal tract, GLN is used as a respiratory fuel. The enteral administration of GLN results in increased uptake of luminal GLN by the gut mucosa accompanied by a simultaneous decrease in uptake of GLN from the circulation. Thus, the consumption of GLN by the gut is balanced between these two sources of GLN.

Most of the GLN taken up by the gastrointestinal tract occurs via the epithelial cells lining the villi of the small intestine. The GLN metabolism which occurs in the small intestine provides a major source of energy for the gut and produces precursors for hepatic ureagenesis and gluconeogenesis by processing nitrogen and carbon from other tissues.

Baskerville et al. (*Brit. J. Exp. Pathol.*, 61:132 (1980)) lowered the concentration of plasma GLN to undetectable levels by infusing purified glutaminase into rhesus monkeys, marmosets, rabbits, and mice, resulting in vomiting, diarrhea, villus atrophy, mucosal ulcerations, and intestinal necrosis Martin et al. (U.S. Pat. No. 2,283,817) disclose a composition containing GLN which is used as a detoxicant, rather than a dietary supplement. In the patent, GLN is combined synergistically with other amino acids to act directly on a toxin to inhibit any deleterious effect.

In Shive et al. (U.S. Pat. No. 2,868,693), GLN-containing compositions for the treatment of peptic ulcers are disclosed.

Further evidence of the potential protective effect of GLN was shown by Okabe et al., *Digestive Disease*, 20:66 (1975), who found that GLN could protect against aspirin-induced gastric ulcerations in humans. These effects were not observed when GLN was given by tube feedings into the intestine, thus preventing direct exposure of the gastric mucosa to GLN. This indicates that the GLN effects on gastric ulceration were local and not secondary to altered systemic nutrition. The non-essential amino acid GLN is not present in standard parenteral alimentation solutions yet is a preferred oxidative fuel for the small intestine (Windmeuller, H. G., *Adv. Enzyml.* 53:201-237 (1982)) and has trophic effects on the intestinal mucosa of intravenously (i.v.) fed rodents (Hwang, T. L. et al., *Surgical Forum* 37:56-58 (1986); O'Dwyer, S. T. et al., *Clin. Res.* 35:369A (1987)). This visceral GLN requirement may be even greater during critical illness, when GLN metabolism by the small intestine is known to be increased (Souba et al., *Surgery*, 94(2):342 (1983)). Although GLN is known to be rapidly consumed by the pancreas and appears to be concentrated in the exocrine part of the gland (Cassano, G. B. et al., *J. Neurochemistry* 12:851-855 (1965)), the effect of exogenously administered GLN on the exocrine pancreas of intact animals has not been reported.

At present, the nutritional requirements of patients who are unable to feed themselves adequately are met through the administration of enteral or parenteral diets. Enteral diets are usually administered using small-bore tubing which is placed through the nose into the gastric, or duodenal regions, or through surgical implantation as in, for example, gastrostomy, or jejunostomy. Those enteral formulas which are presently available can be divided into four basic categories: elemental, polymeric, modular, and altered amino acids. These formulae contain GLN. The levels of nutrients present in the enteral diets, however, are generally based upon the dietary requirements of a normal individual and not that of a patient suffering from a catabolic disease.

Elemental formulas require minimal digestive action and are composed primarily of small peptides and/or amino acids, glucose oligosaccharides, and vegetable oil or medium-chain triglycerides.

In polymeric formulas, complex nutrients such as, for example, soy protein, lactalbumin, or casein are utilized as a source of protein; maltodextrins or corn syrup solids as a source of carbohydrate; and vegetable oils or milk fat as a source of fat.

Modular diets can be produced by combining protein, carbohydrate, or fat with a monomeric or polymeric formula to meet special nutritional requirements.

Formulas which are composed of altered amino acid compositions are used primarily for patients with genetic errors of nitrogen metabolism or acquired disorders of nitrogen accumulation, the object often being to limit the intake by the patient of certain amino acids which may be detrimental.

Parenteral diets are usually administered intravenously (i.v.). These i.v. fluids are sterile solutions composed of simple chemicals such as, for example, sugars, amino acids, and electrolytes, which can be easily assimilated.

The term "total parenteral nutrition" (TPN) is used to describe formulas for use in patients who derive their entire dietary requirements i.v. Total parenteral nutrition formulas, unlike enteral formulas, do not normally contain GLN. The absence of GLN from parenteral formulas is due, in part, to concern with respect to its instability at room temperature, and the resulting generation of ammonia and pyroglutamic acid. There has also been concern about the generation of glutamic acid from GLN because of the potential toxicity of glutamic acid as a neurotransmitter. In fact, these concerns do not appear to be justified at the pH values of enteral and parenteral nutrition solutions.

TPN results in villus atrophy, a phenomenon which is generally reversible when oral feedings are resumed. Since TPN formulas lack GLN, the body's requirements for this amino acid must be met from synthetic pathways in body tissues.

In patients with critical illnesses, net protein catabolism is associated with markedly diminished muscle GLN pools and reduced plasma GLN (Askanazi et al., *Ann. Surg.* 192:78 (1980); Askanazi et al., *Ann. Surg.*, 191:465 (1980)), and a presumed increase in intestinal GLN utilization (Souba et al., *Arch. Surg.*, 120:66 (1985); Souba et al., *Surgery*, 94(2):342 (1983)). Glucocorticoids also are known to increase GLN consumption by the small intestine (Souba et al., *Surgical Forum*, 34:74 (1983)).

TPN is associated with reduced pancreatic weight and diminished pancreatic exocrine secretion in addition to gastrointestinal mucosal atrophy (Hughes, C. A. et al., *Clin. Science* 59:329-336 (1980); Johnson, L. R. et al., *Gastroenterology* 68:1177-1183 (1975); Johnson, L. R. et al., *Am. J. Physiol.* 233:E524-E529 (1977); Towne, J. B. et al., *Am. J. Surg.* 126: 714-716 (1973)). Animals given sufficient nutrients i.v. to sustain body growth, develop as much pancreatic atrophy as occurs during starvation (Johnson, L. R. et al., (1975), supra). The etiology of pancreatic atrophy is poorly understood and may be secondary to various factors that normally accompany oral nutrient intake including: (1) the absence of luminal substrates (Clark, R. M., *Clin. Sci.* 50:139 (1976)); (2) lack of dietary amines (Seidel, E. R. et al., *Am. J. Physiol.* 249:G434-438 (1985)); (3) absence of fermentable fiber (Jacobs, L. R. et al., *Am. J. Physiol.* 246:G378-G385 (1984)); (4) alterations in neurohumoral processes (Johnson, L. R., *Physiology of the Gastrointestinal Tract*, 2d Ed., pp. 301-319, Raven Press, NY (1987)) or (5) changes in pancreaticobiliary secretions (Fine, H. et al., *Am. J. Physiol.* 245:G358-G363 (1983)). Additionally or alternatively, pancreatic atrophy may be influenced by the absence of specific nutrients in currently available parenteral alimentation solutions (Wilmore, W. W. et al., *Surgery* 104(5):917-923 (1988)).

Bone marrow transplantation is increasingly utilized in the treatment of hematologic malignancies (Thomas et al., Indications for bone marrow transplantation. *Annu Rev Med* 35:1-9 (1984)). Individuals undergoing bone marrow transplantation consistently lose body protein due to the catabolic effects of chemotherapy, total body irradiation and graft-versus-host disease, while gastrointestinal toxicity often limits consumption and absorption of enteral nutrients (Schmidt et al. *Exp Hematol* 8:506-11 (1980); Szeluga et al. *JPEN J Parenter Enteral Nutr* 9:139-43 (1985); Cheney et al. *Cancer* 59:1515-9 (1987); Weisdorf et al., *J Pediatr Gastroenterol Nutr* 3:95-100 (1984); and McDonald et al. *Gastroenterology* 90:460-84 (1986)). Infectious complications also remain a major cause of morbidity in marrow transplant patients (Meyers J. D., In: Mandell G. L., Douglas R. G., Bennett J. E. (ed): Principles and Practice of Infectious Diseases, 3rd edition. New York: Churchill Livingstone; pp. 2291-4. (1991)). Infection accelerates protein loss (Wilmore D. W., The Metabolic Management of the Critically Ill, 2nd edition. New York: Plenum Medical Book Company, 1980.) and protein-calorie malnutrition may decrease host resistance to microbial invasion (Scrimshaw et al., *Am J Med Sci.* 237:367-403 (1973)).

Modification of amino acid formulations may improve clinical and metabolic efficacy of parenteral nutrition. In this study, we evaluate the effect of intravenous nutrition supplemented with glutamine. Glutamine is absent in all commercially available parenteral nutrient solutions, as it has a shorter shelf life than other amino acids commonly utilized and has been considered a nonessential amino acid. However, during catabolic states, glutamine concentrations in intracellular pools (primarily skeletal muscle) fall rapidly as glutamine is utilized for renal ammoniagenesis and serves as an oxidizable fuel for stimulated lymphocytes and macrophages and intestinal mucosal cells (Wilmore et al. Injured man: Trauma and sepsis. In: Winters R. W., ed. Nutritional Support of the Seriously Ill Patient. New York: Academic Press, pp. 33–52 (1983); Welbourne T. C., *Am J Physiol* 253:F1069-76 (1987); Windmueller H. G., *Adv Enzymol* 53:201-37 (1982); Newsholme et al. *Nutrition* 4:261-68 (1988)). Recent animal studies demonstrate that glutamine-enriched parenteral or enteral nutrition enhances nitrogen balance, attenuates intestinal mucosal damage, decreases bacteremia and improves survival following irradiation or chemotherapy when compared to glutamine-free nutrition (O'Dwyer et al. *Clin Res* 35:369A (1987); Klimberg et al. *Cancer* 66:62-8 (1990); Fox et al. *JPEN J Parenter Enteral Nutr.* 12:325-31 (1988); Fox et al. *JPEN J Parenter Enteral Nutr.* 12(suppl):8S (1987)). Limited clinical studies in postoperative patients have shown improved nitrogen retention with glutamine-enriched parenteral feeding (Stehle et al. *Lancet* i:231-23 (1989); Hammarqvist et al. *Ann Surg* 209:455-61 (1989)). The clinical safety of L-glutamine added as a component of balanced parenteral nutrient solutions has recently been documented (Ziegler et al. *JPEN J Parenter Enteral Nutr.* 14(suppl):137S-46S (1990)).

None of the prior art studies have shown that breakdown of skeletal muscle, atrophy of intestinal villi and of the pancreas, breakdown of the gut wall leading to enhanced permeability, compromised immune function, or other catabolic dysfunctions which occur during TPN can be prevented through the administration of high levels of GLN.

SUMMARY OF THE INVENTION

In the invention, an animal having, or at risk of having, catabolic, gut-associated pathological processes (catabolic dysfunction) including intestinal mucosal and pancreatic atrophy, enhanced gut permeability, impairment of host defenses and compromised immune function, associated with cancer radiation therapy or chemotherapy or intravenous feeding, or being treated with bone marrow transplantation, is given a therapeutically effective amount of GLN. This amount of GLN is greater than that normally encountered in the diet of healthy individuals. This increased level of GLN is necessary to compensate for the greater demand for GLN which occurs during certain catabolic dysfunctions. In the absence of an exogenous source, GLN would be derived through the breakdown of muscle tissue during such catabolic conditions. The decline in GLN concentrations in the plasma in spite of accelerated GLN release from muscle during catabolic dysfunction indicates systemic GLN deficiency. In spite of accelerated GLN release from muscle, intestinal mucosal cell demand exceeds the supply. This, in turn, predisposes to intestinal villus atrophy, and breakdown of the gut wall barrier. Loss of this barrier, along with associated compromised immune function in gut-associated as well as in other lymphoid tissue, are important predisposing factors for infection. In addition to intestinal damage, pancreatic atrophy occurs under similar conditions.

Thus, the present invention provides a method for treating catabolic, gut-associated pathological processes including intestinal mucosal and pancreatic atrophy, enhanced gut permeability, impaired host defenses and compromised immune function and for promoting recovery from bone marrow transplantation, in an animal, the method comprising administering to the animal a therapeutically effective amount of GLN or functional analogues of GLN.

Provision of exogenous GLN to a stressed patient better supports the metabolic requirements of the small intestine and immune system and decreases the rate of systemic protein catabolism. Provision of GLN to patients undergoing bone marrow transplantation is especially beneficial in ameliorating gastrointestinal damage and compromised immune function consequent to radiation/chemotherapy, graft-versus-host disease, and TPN. Provision of GLN in patients with inflammatory bowel disease is also beneficial.

It is conceivable that the therapeutic efficacy of glucocorticoids in inflammatory bowel disease is related not only to their anti-inflammatory properties, but also to their role in increasing substrate metabolism within the enterocytes lining the gut. Administration of exogenous GLN by providing even more substrate for the enterocytes also contributes to prevention of GLN depletion of plasma and skeletal muscle. Similarly, GLN may promote the survival of transplanted small bowel or support gut metabolism in infants with intestinal immaturity.

DETAILED DESCRIPTION OF THE PREFERRED EMBODIMENTS

Figure 1:
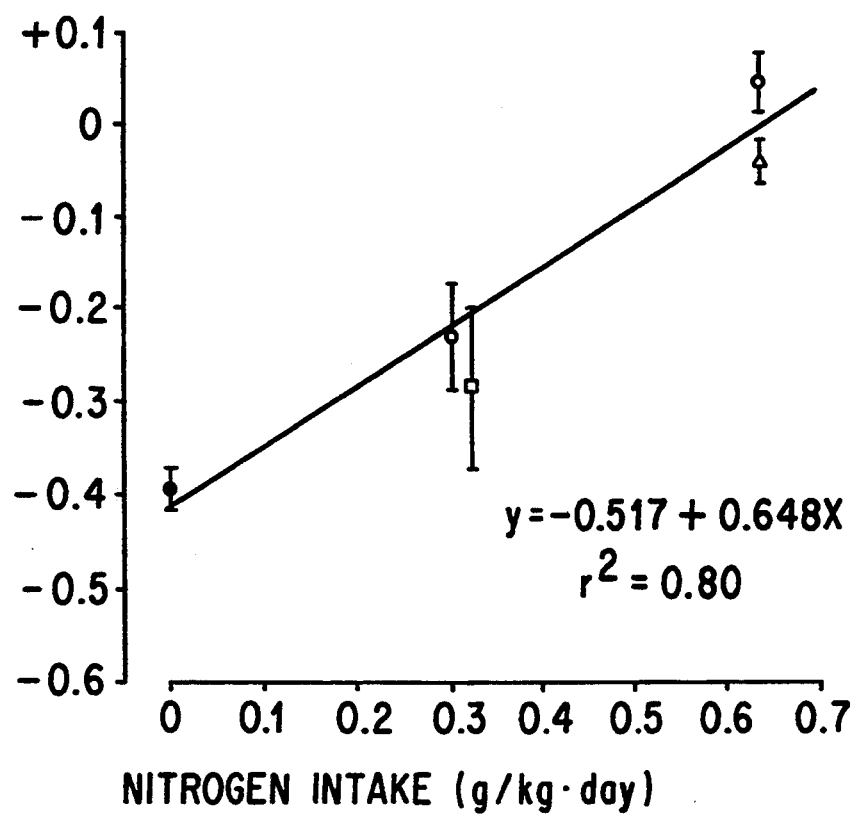
FIG. 1 shows a plot of nitrogen balance as a function of nitrogen intake.

The inventors have devised a new method of treating catabolic, gut-associated pathological processes (catabolic dysfunctions) including intestinal mucosal and pancreatic atrophy, enhanced gut permeability, impairment of host defenses and compromised immune function. The present invention comprises the administration to an animal afflicted with, or likely to develop, one of the above disease states, a therapeutically effective amount of GLN or a functional analogue thereof. This therapeutically effective amount is greater than that present in a normal diet. The normal dietary intake for humans is about 2 to 4 g/day.

A catabolic dysfunction is a condition which induces a net catabolic response in which the degradation of an anatomical structure occurs. The dietary administration of GLN appears to satisfy the biochemical requirements of these catabolic conditions such that it is not necessary for the body to synthesize GLN or to obtain GLN from the breakdown of skeletal muscle.

The present invention is intended to be used in all catabolic dysfunctions where there is an increased demand for GLN. These catabolic dysfunctions can either be associated with organs and cells of the gastrointestinal tract or with other cells and organs systems. Atrophy of the villi of the small intestine during administration of a parenteral diet does not usually occur due to direct catabolic activity on the enterocytes, but rather, is due to the lack of GLN in the diet of patients.

The term "enteral" is intended to indicate a method of administration of nutrients to that portion of the alimentary canal between the stomach and the anus.

The term "parenteral" denotes method of administration of nutrients to that region outside of the digestive tract.

Parenteral catabolic dysfunctions which display increased demand for GLN occur in many clinical states including sepsis, during or following surgery, burn injuries, calorie deprivation and uncontrolled diabetes.

Animals in which the invention is effective are those commonly classified as mammals, including humans.

The term "pathologic gut permeability" denotes an enhancement in the permeability of the gut wall associated with a disease state. Such gut permeability, detectable by various means such as, for example, the absorption and urinary excretion of intragastrically introduced lactulose, is associated with administration of cancer chemotherapeutic agents, with TPN, and with other injuries or disease states. Increased gut permeability can increase the pathogenicity of microorganisms which are normally prevented from passing across the gut wall barrier.

By the term "treating" is intended prevention, amelioration, or cure of a symptom or set of symptoms constituting a disease state.

The term "pancreatic atrophy" denotes loss of pancreatic tissue, or pancreatic function.

The term "compromised immune function" denotes a reduction in an immunological function, which can be measured in vitro or in vivo. Such functions include, but are not limited to, lymphocyte proliferation in response to an antigen or a mitogen, antibody responses, cell mediated immune responses such as delayed hypersensitivity. Various forms of compromised immune function, all of which are intended by the term, can lead to decreased host defenses to a variety of pathogens such as pathogenic microorganisms. Compromised immune function is a well-known consequence of treatment with chemotherapeutic drugs, and is also a consequence of certain forms of physical trauma, burns, malnutrition, diabetes and other disease states.

The term "impairment of host defense" denotes an increase in susceptibility to infection by a variety of pathogenic microorganisms, including, but not limited to, bacteria, viruses, and fungi. Many microorganisms which are not normally pathogenic, or only mildly pathogenic, become pathogenic due to an impairment of host defense (opportunistic microorganism). These include, but are not limited to Candida albicons, staphylococcus sp., Aspergillus sp., and E. coli. Such impairment occurs following breakdown in the gut wall barrier, allowing the normally prevented passage of pathogens from the gut lumen across the mucosal barrier. Such impairment may result from compromised immune function, in which the cells of the immune system are suppressed in their ability to respond to the antigenic structures associated with the pathogens. Impaired host defense also results from abnormal function of other cells including depressed leukocyte chemotaxis, phagocytosis, and killing, altered macrophage function, and of other innate mechanisms of host resistance, which are well known in the art (see Mims, C. A., The Pathogenesis of Infectious Disease (2nd Edition), 1982, Academic Press, N.Y., which is hereby incorporated by reference.)

A requirement for GLN in tissue culture medium for the survival or growth of a large variety of cell types is well known in the art (Freshney, CULTURE OF ANIMAL CELLS, A Manual of Basic Technique, Alan R. Liss, Inc., New York, 1983), which is hereby incorporated by reference). It is well known, for example, that lymphocyte proliferation and differentiation in vitro is highly dependent on increased concentrations of GLN in the medium. Insufficiency of GLN in vivo, for example following TPN to which GLN has not been added, can be shown to lead to a suppression of lymphocyte function. This loss of function is either prevented in part, or is partially restored, by the addition of GLN to the TPN formula.

The term "substantially associated with," as applied to the dysfunctions or symptoms for which the method of the invention is effective, means those dysfunctions wherein the biochemical demand for GLN occurs during or after the dysfunction, and is related thereto.

The administration of GLN can be by both enteral and parenteral means.

Examples of the means of enteral administration of GLN is the use of small-bore tubing placed via the nose into the gastric or duodenal regions, or through surgical implantation as in, for example, gastrostomy, or jejunostomy.

Examples of parenteral routes of administration include, but are not limited to, subcutaneous, intramuscular or intravenous injection, and nasopharyngeal, mucosal or transdermal absorption. In most cases, the GLN is administered i.v. In i.v. administration, the therapeutically effective amount of GLN, in liquid form, is directly administered from a reservoir from which tubing connects to a needle which is placed into a large vein of the patient.

Regardless of which route of administration is utilized, the GLN can be administered either singly or as a dietary supplement. When used as a dietary supplement, the GLN can be mixed with an existing enteral or parenteral diet prior to administration to the patient. It is also possible to administer the GLN without mixing it directly with the other components of a diet as, for example, in i.v. feeding wherein the GLN is not directly added to the main i.v. bottle, but instead is added to a common reservoir using a "piggy-back" bottle.

Functional analogues, derivatives, substitution products, isomers, or homologues of GLN which retain the characteristics of GLN are contemplated as equivalents. Preferred are those analogues capable of donating an amine group and being metabolized in the Krebs cycle. Most preferred are compounds which possess the amino acid residue at one terminus of a carbon chain and an amine moiety at the other terminus of the carbon chain.

The therapeutically effective dose ranges for the administration of GLN are those large enough to prevent the catabolism or atrophy of the tissues of the body in order to maintain metabolic homeostasis. In an enteral diet GLN would be administered at a rate greater than or equal to 0.3 grams per kilogram of body weight per day. Such administration rates could be 0.3 to 2.0 grams per kilogram of body weight per day, preferably 0.3 to 1.5 grams per kilogram of body weight per day, and more preferably 0.4 to 1.0 grams per kilogram of body weight per day. The rate of administration for GLN when administered i.v. would be greater than or equal to 0.1 grams per kilogram of body weight per day. Such administration rates could be 0.2 to 3.0 grams per kilogram of body weight per day, preferably 0.3 to 2.5 grams per kilogram of body weight per day, more preferably 0.4 to 2.0 grams per kilogram of body weight per day.

According to the method of the invention, GLN may be administered by simply modifying existing dietary formulas to contain the proper concentration of GLN. Most preferably, the GLN would remain in a dry form such as, for example, a sterile lyophilized powder which is aseptically hydrated at the time of administration and mixed at the proper concentration with the other components of the dietary composition. Alternatively, the GLN could be premixed with the other components of a dry formula which is aseptically rehydrated at time of administration, or stored as a frozen concentrate which is thawed and mixed at the proper concentration at time of use.

The use of GLN by the method according to the invention is ideally suited for the preparation of compositions. These compositions may comprise GLN, GLN-containing dipeptides, GLN salts, either alone or in combination with other chemicals. These other chemicals can be pharmaceutically acceptable carriers, as well as other active substances of the diet as, for example, free amino acids, protein hydrolysates, or oils.

Preparations for parenteral administration include sterile aqueous or non-aqueous solutions, suspensions, and emulsions. Carriers or occlusive dressings can be used to increase skin permeability and enhance cutaneous absorption.

The invention also relates to a medicament or pharmaceutical composition comprising the components of the invention, the medicament being used for treating catabolic dysfunction, gut-associated pathologies including intestinal mucosal and pancreatic atrophy, enhanced gut permeability, impairment of host defenses and compromised immune function and for promoting recovery from bone marrow transplantation.

The invention also relates to GLN-rich compositions for preventing or ameliorating catabolic dysfunctions. Compositions which are GLN-rich contain GLN in levels which are therapeutically effective and are greater than that present in the normal diet.

Containers containing the composition of the invention can be used to facilitate the administration of GLN according to the method of the invention. These containers are designed to contain, for example, the daily dosage of GLN to be administered to the patient.

Containers adapted for i.v. administration of GLN alone or in combination with other amino acids are especially useful. Such containers could comprise a receptacle for the liquid GLN-containing composition, and a liquid conducive means capable of attachment to a needle.

The liquid conducive means could be any object capable of conveying the liquid composition in the receptacle to the needle such as, for example, plastic tubing.

The needle attached to the conducive means could either be inserted directly into a blood vessel or i.v. catheter of the human recipient or could be inserted into a reservoir to enable mixing with another solution before being administered to the patient.

The above disclosure generally describes the present invention. A more complete understanding can be obtained by reference to the following specific examples which are provided herein for purposes of illustration only and are not intended to be limiting unless otherwise specified.

EXAMPLES

Example 1

Animal Care and Operative Procedures

Twenty-two mongrel dogs, weighing between 20 and 40 kg, were obtained from a farm where they had been regularly exercised and screened for parasites. All female animals were nonpregnant. While in the kennel, the animals were maintained in accordance with the guidelines of the Committee on Animals at Harvard Medical School and the Committee on Care and Use of Laboratory Animals of the Institute for Laboratory Animal Resources, the National Research Council (DHEW Publication #NIH 78-23, reviewed 1978). The animals were kept in individual kennels at a constant temperature of 20° C. with 24-hour light exposure. They were exercised for two hours every morning, provided water ad libitum, and given a single daily feeding between 1:00 and 3:00 pm of Agway Respond 2000 Dry Dog Chow ® (contains at least 25% protein, 10% fat, and the remaining calories as carbohydrate).

Five to seven days were allowed for the dogs to acclimate to the kennel conditions, during which time they were trained to rest quietly in a Pavlov stand. On the day before obtaining basal samples, all food was removed from the kennel at 5:00 pm. After an overnight fast, the dog was walked for at least 20 minutes, placed in a Pavlov stand, and a foreleg vein was cannulated. After the dog had rested in the stand for at least 20 minutes, a venous blood sample was obtained for amino acid determination. Following rapid induction of anesthesia with intravenous sodium thiopental (Abbott Laboratories, 5 mg/kg body weight), a biopsy of the vastus lateralis muscle was obtained by the method of Bergstrom et al., *Journal of Applied Physiology* 36:693–697 (1974). The animal was then taken out of the stand and a 5-ml sample of arterial blood was obtained from the femoral artery via percutaneous puncture.

The animal was allowed to recover from the biopsy for a minimum of two days prior to the standard operative procedure. On the day prior to surgery, all food was again removed from the kennel at 5:00 pm. At 7:00 am, the dog was walked for 20 minutes and then taken to the operating suite where it was anesthetized with i.v. sodium pentobarbital (Abbott Laboratories, 30 mg/kg body weight). An endotracheal tube was placed, and the animal was allowed to spontaneously breathe a mixture of oxygen and room air. The dog was placed on an operating table in a supine position, and a cannula was placed by percutaneous puncture into the external jugular vein and directed into the superior vena cava. After noting the starting time, the infusion solution was administered via this cannula by constant infusion (IMED pump®, San Diego, Calif.) at 4 ml/hr/kg. Penicillin G (E. R. Squibb, Princeton, N.Y.; 600 mg) and Keflin® (Eli Lilly, Indianapolis, Ind.; 1 gram) were given i.v. The urinary bladder was catheterized, the initial urine sample was discarded, and the catheter was connected to a closed urine bag for 24-hour collection. The abdomen and flanks of the dog were shaved, and the skin was washed with soap and water and prepared with a povidone iodine prep solution (Clinipad Corporation, Guilford, Conn.). The dog was draped with sterile sheets and the abdominal cavity entered via a vertical infra-umbilical incision in females and a right paramedial incision in males. The bowel was retracted into the upper abdomen, and the exposed retroperitoneum incised. The right deep circumflex iliac artery and vein and the medial sacral artery were isolated by sharp and blunt dissection. A specially prepared catheter consisting of a 6 cm segment of polyethylene tubing (2.08 mm OD) coated with silastic and linked to a 2.8 mm OD polyethylene catheter was inserted 6 cm cranially into the aorta via a right deep circumflex iliac artery. A similar catheter was inserted into the middle sacral artery, its tip being positioned approximately 1 cm proximal to the bifurcation of the aorta, but distal to the inferior mesenteric artery. A third catheter was inserted into the inferior vena cava via the right deep circumflex iliac vein and positioned distal to the renal vein. All catheters were secured and exteriorized through stab wounds in the flank. The abdomen was then closed and the animal turned onto its left side. The exterior catheters were cut to appropriate lengths, plugged with blunt needles connected to intermittent injection ports (Jelco®, Critikon, Inc, Tampa, Fla.), flushed with saline, filled with heparin (1,000 units/ml), and buried subcutaneously. The injection ports were positioned high on the flank of the animal under the skin and in the approximate vicinity of the vertebral column. This allowed access to the aorta and vena cava by percutaneous puncture of the injection ports of the catheters. Two further doses of Keflin® (1 gram) were given 8 and 24 hours post-operatively via the venous catheter.

Following the operative procedure, the animal was placed on its side, and body temperature was maintained with heat lamps and blankets during recovery from anesthesia. Approximately five hours after the start of the infusion, the animal was placed in Pavlov stand, and a solution of para-aminohippuric acid (PAH, 0.5% w/v in saline) was infused at a rate of 0.76 ml/minute with a Harvard pump into the distal aorta through the medial sacral artery catheter. After 40 minutes of dye infusion, simultaneous arterial and venous samples were obtained for measurement of amino acid and PAH concentrations. Three sample sets were drawn at 10-minute intervals over a period of 20 minutes. The catheters were then flushed, filled with heparin, and the animal was kept in a Pavlov sling. Twenty-three hours following the initiation of the experiment, the hindquarter flux studies were repeated. After 24 hours, the urine collection was terminated. The animal received i.v. sodium thiopental, as previously described, and biopsy of the vastus lateralis muscle in the leg not previously biopsied was performed. The i.v. infusion was terminated, and the animal placed in a metabolic cage for the ensuing 24 hours where it was offered water ad libitum and no food.

Example 2

Infusion Solutions

All animals received an infusion at a rate of 4 ml/hr/kg. Five control animals received 0.9% saline. Other animals were given commercially available amino acid solution (FreAmine III®, American McGaw) at two different concentrations designed to deliver approximately 0.312 (N=2) or 0.624 (N=6) grams of nitrogen/24 hr/kg body weight. The higher dose was designed to provide the equivalent of 4 grams of protein/24 hr/kg body weight. Three animals received a solution containing GLN at 0.312 grams nitrogen/24 hr/kg. A final group (N=6) received an equal mixture of GLN and FreAmine®, providing nitrogen at 0.624 grams/24 hr/kg. The GLN solutions were made by dissolving L-GLN (Sigma, St. Louis, Mo.) in distilled water to form a 0.157M solution which was then adjusted to pH 6.8 with sodium hydroxide. This solution was sterilized by filtration through a 0.22 uM membrane and stored at 4° C. for less than 24 hours. On the morning of utilization, the solutions were formulated at required concentrations in 2-liter bags (American McGaw) and maintained at 4° C. until use. A 10 ml sample was taken from each bag at the end of the infusion and stored at −20° C. for analysis of nitrogen content. An additional 10 ml sample was adjusted to pH 4.75 as described below and stored frozen for analysis of GLN content.

Example 3

Preparation and Analysis of Samples

Whole blood and plasma samples were deproteinized by combining with equal volumes of ice cold 10% (w/v) perchloric acid and then centrifuging at 3,000 rpm at 4° C. for 20 minutes. A 2 ml aliquot of the supernatant was buffered with 0.2 ml of 0.2M sodium acetate buffer (pH 4.90), adjusted to pH 4.75–4.90 with 5N potassium hydroxide, and brought to a final volume of 4 ml with distilled water. The samples were stored at −20° C. for later batch analysis of GLN and glutamate concentrations, using an enzymatic microfluorometric assay modified from the method of Lund (In: Bergmeyer (ed.) *Methods of Enzymatic Analysis*, Vol. 4, Academic Press, 1974, pp. 1719–1722.)

During the muscle biopsy procedure, a stop watch was started immediately when the tissue was removed. The muscle was dissected free of fat and connective tissue and divided into two unequal portions. Both samples were weighed at least four times over the ensuing two minutes, and the weight and time following biopsy were recorded. Actual muscle wet weight at time zero was calculated from the best fit linear regression of weight plotted against time. The smaller sample (approximately 15 mg) was dried to a constant weight in a 90° oven, and the weight of dry, fat-free solids was obtained after extraction in petroleum ether. This sample was then digested in 250 ul of 1N nitric acid, and the chloride content was measured by titration with silver nitrate using a semi-automated titrator (Radiometer, Copenhagen). Plasma chloride was also determined and intra- and extracellular water calculated by the method of Bergstrom et al., supra. The second muscle sample (approximately 100 mg) was homogenized in 0.5 ml of ice cold perchloric acid (10% w/v) with a Polytron Homogenizer (Brinkman, Westbury, N.Y.). The homogenate was centrifuged and the supernatant prepared for enzymatic GLN and glutamate analysis.

At the start of this study, plasma and intracellular GLN and glutamate concentrations were determined by an enzymatic method previously described (Muhlbacher et al., *American Journal of Physiology* 247:E75−E83 (1984)). Concentrations of other amino acids were determined by automated high performance liquid chromatography (HPLC) after pre-column derivatization with o-phthalaldehyde. All amino acids commonly found in proteins were quantitated except GLN, glutamate, proline, cysteine, and lysine. As the study progressed, techniques were developed for GLN-glutamate measurement using HPLC. Samples measured by the two techniques (enzymatic and HPLC) yielded comparable glutamine-glutamate concentrations; hence, only HPLC analysis was utilized in the latter portion of the study. The concentration of PAH in arterial and venous samples was determined spectrophotometrically following deproteinization with 5% trichloroacetic acid (Muhlbacher et al., supra).

Urine excreted during the 24 hours of infusion was collected in the closed urinary collecting system and stored in acidified, refrigerated containers. Aliquots were stored frozen at −20° C. for batch analysis. The nitrogen content of the infusion solution and urine was determined in the same batch by the macro-Kjeldahl method (Peters et al., *Quantitative Clinical Chemistry*, Vol. II, Williams & Wilkins, Baltimore, Md., 1932, pp. 516–538).

Statistical calculations were performed on an IBM 4341 Computer utilizing a standard statistical package (Minitab, The Pennsylvania State University, State College, Pa., 1983). The results are expressed as mean±SEM. Paired and unpaired Student's t-tests were used as appropriate. Analysis of variance was used for multiple group comparisons. Regression analysis was performed using methods of least squares. Because of the small sample size in the groups receiving 0.312 grams of nitrogen/24 hr/kg, most statistical comparisons were only performed between the other groups.

Hindquarter blood flow was calculated as previously described (Muhlbacher et al., supra), and the rate was expressed per kg body weight to account for variation in size of the animals. Amino acid flux rates were calculated as the product of blood flow and arterial-venous concentration differences. Three sets of samples were drawn, flux was calculated for each set, and the mean of the three values determined (Muhlbacher et al., supra). Total amino acid nitrogen in whole blood, plasma, and intracellular water was calculated by taking into account the nitrogen content of each amino acid and summing the individual concentrations.

Example 4

Plasma and Intracellular Amino Acid Concentrations

Plasma amino acid concentrations were measured pre-operatively and 24 hours following the standard operation. In the saline-treated animals, the total nitrogen content of the plasma was unchanged by the operative procedure (Table I). The GLN concentration remained constant, but the BCAA's rose, the sum of their concentrations increasing from 326±21 to 501±9 umol/l ($p<0.01$). In the animals receiving 0.624 grams N/24 hr/kg, there was an upward trend in the plasma nitrogen concentration that was statistically significant only in the group receiving the mixture of amino acids plus GLN. The plasma GLN concentration also rose in this group. BCAA's were elevated in all animals receiving amino acid infusions.

Skeletal muscle nitrogen concentration declined during saline infusion (Table II). This decrease in total amino acid nitrogen was reflected primarily by a fall in GLN from 21.48±3.21 umol/l intracellular water to 15.86±3.80 ($p<0.05$). Although the sum of the concentrations of non-essential amino acids diminished, the sum of total essential amino acids in the intracellular pool remained unchanged. No change in intracellular nitrogen of GLN occurred in animals receiving 0.624 gm of amino acid nitrogen/24 hr/kg (Table II). There was an upward trend in the intracellular concentration of BCAA's with infusion of the higher amino acid loads, although statistical significance was achieved only in the animals receiving the mixture of amino acids and GLN. There was not a significant change in the total concentrations of essential and non-essential amino acids in these two groups following operation. In contrast to the animals receiving the higher dose of nitrogen, the five animals infused with 0.312 gm N/24 hr/kg did not consistently maintain the skeletal muscle intracellular nitrogen pool, regardless of the solution infused. Intracellular GLN fell in three of the animals, remained unchanged in one, and increased in one (data not shown).

Thus, providing amino acid at 0.624 gm N/24 hr/kg as an amino acid mixture with or without GLN, maintained the skeletal muscle intracellular amino acid pool. A decrease in the intracellular pool, which was characterized by a fall in intracellular GLN, occurred consistently in the animals receiving saline and was variable in the animals receiving the lower dose of amino acids.

Net hindquarter amino acid flux, calculated as the sum of the nitrogen flux of the individual amino acids, averaged −19.05±4.06 umol N/min/kg when measured at 6 hours post-operation in the animals receiving saline. This was significantly greater than the efflux rates of −7.70±5.9 and −6.50±1.18 umol N/min/kg observed in the two groups of animals receiving 0.624 gm of amino acids/24 hr/kg (Table III). However, GLN efflux from the hindquarter was unchanged among these three groups. In contrast, BCAA's were released receiving the higher does of amino acids. Hindquarter exchange of BCAA's appeared to be related to the rate of BCAA administration; the hindquarter demonstrated BCAA release in the saline-treated group, balance with the solution containing amino acids plus GLN, and greater uptake in the group receiving the highest BCAA dose. In the five animals receiving 0.312 gm N/24hr/kg, there was not a significant alteration in hindquarter nitrogen efflux compared to the saline-treated dogs. However, there was considerable variation in these flux data, and the number of animals studied was small. Hindquarter amino acid flux studies 24 hours following operation demonstrated no differences between groups (Table III).

Nitrogen excretion in the five animals infused with saline was 0.492±0.022 gm N/24 hr/kg. In the six animals receiving the highest dose of commercial amino acid mixture, measured nitrogen intake was 0.632±0.001 gm N/24 hr/kg, and nitrogen excretion averaged 0.684±0.031 (Table IV). In the six animals receiving the solution made up of one-half commercial amino acid solution and one-half GLN, nitrogen intake was comparable, but excretion was greater, averaging 0.775±0.019 gm N/24 hr/kg ($p<0.05$). Nitrogen balance in these two groups was significantly less negative than in the animals receiving saline, averaging −0.052±0.031 and −0.140±0.022 gm N/24 hr/kg, respectively. In the five animals that received approximately 0.312 gm N/24 hr/kg, the average nitrogen excretion was intermediate between that observed in the saline controls and in the animals receiving the larger quantity of infused nitrogen. Taken together, these studies demonstrated that nitrogen balance approached equilibrium as the quantity of administered nitrogen increased (FIG. 1). When GLN was combined with a commercial GLN-free amino acid solution, the effects on nitrogen balance were additive. When summed together, the nitrogen retained in response to the infusion of commercial amino acids or GLN alone accounted for the nitrogen retained when the solutions were combined.

These studies show that operative stress in dogs stimulates net skeletal muscle protein breakdown, as evidenced by negative nitrogen balance and increased amino acid efflux from the hindquarter in association with a fall in the intracellular skeletal muscle free amino acid pool. Previous studies have demonstrated that protein wasting is not related to fasting or anesthesia, but is clearly a response to the operative stress (Kapadia et al., *Surgical Forum* 33:19–21 (1982)). The release of amino acids from the hindquarter 6 hours post-operation in the saline-treated group was approximately 6 to 8 times that observed in chronically catheterized, post-absorptive dogs studied under basal conditions (Mulhbacher et al., *American Journal of Physiology* 247:E75–E83 (1984)). This rate of hindquarter nitrogen release cannot be accounted for by depletion of the intracellular free amino acid pool and therefore must reflect net skeletal muscle proteolysis.

Provision of amino acids in the perioperative period offset the nitrogen loss, maintained or increased plasma amino acid concentrations, and diminished the fall in the skeletal muscle intracellular free amino acid pool. These effects appear to be related to the quantity of amino acid nitrogen infused. Whole body and hindquarter nitrogen losses were greatly decreased at the highest amino acid doses, which also maintained intracellular pools of GLN and other amino acids. These results differ from the findings reported by Askanazi et al., *Annals of Surgery* 191:465 (1980), who described a decline in the intracellular concentrations of GLN and other amino acids in patients after hip replacement that could not be reversed by infusion of dextrose and amino acids. Results obtained using the method of the invention indicate that this earlier finding may be related to the quantity of amino acids infused and/or the lack of GLN in the infusate. Infusion of lower concentrations of amino acids (0.312 gm N/24 hr/kg), either as GLN alone or as FreAmine ®, failed to maintain the intracellular amino acid pool in three of the five animals studied. In contrast, the higher rate of amino acid infusion stabilized or increased the intracellular pool. Thus, it appears that an adequate quantity of administered nitrogen can maintain the skeletal muscle intracellular amino acid pool post-operatively.

The change in the intracellular free amino acid pool in saline-infused animals, largely attributable to a rapid fall in GLN, was prevented when adequate nitrogen was provided. This occurred even when GLN was not present in the commercially available solution. The mechanism by which intracellular GLN was maintained under these circumstances is unclear, although it seems probable that GLN substrate for GLN synthesis was derived from the BCAA's via transamination. For unexplained reasons, net GLN efflux was similar in all groups. Hindquarter release of GLN was not accelerated by BCAA's or attenuated by the provision of GLN in the amino acid solution. The results in this post-operative model differ from reported effects of BCAA's in normal humans, in whom BCAA forearm uptake following the administration of leucine orally was associated with accelerated GLN release (Aoki et al., *Journal of Clinical Investigation* 65:1522 (1981)).

Although there were marked differences in composition of the two amino acid solutions administered at the rate of 0.624 gm N/24 hr/kg, hindquarter nitrogen efflux was comparable in both groups of animals. occurred even though the quantity of essential amino acids and BCAA's in the balanced solution was twice that in the GLN-containing solution. Thus, in this experimental model of operative stress, GLN supplementation of a balanced amino acid formula was at least as effective as two-fold concentration of standard balanced formula in diminishing hindquarter loss.

In the dogs that received saline, BCAA's were released from skeletal muscle. Quantitative transfer rates calculated from these data suggest that a marked uptake of BCAA's must have occurred in visceral organs, most probably in the liver, during the early post-operative period. The provision of BCAA's appeared to offset this translocation, perhaps by both meeting visceral requirements and reversing skeletal muscle efflux. A quantitative relationship also existed between hindquarter nitrogen balance and preservation of the intracellular nitrogen pool. When intracellular pools were maintained, the hindquarter was near nitrogen equilibrium; when saline was administered, amino acid concentrations in the intracellular pool were markedly depleted and there was a marked loss of hindquarter nitrogen. Although the relationship between skeletal muscle proteolysis and nitrogen concentration in the free amino acid pool is unknown, these data suggest that skeletal muscle nitrogen balance is related to the intracellular amino acid concentration and that GLN can play an essential role in maintaining a homeostatic balance in the body.

TABLE I

Plasma Amino Acid Concentration (Mean ± SEM)

| Solution Infused | Pre-operative | | | 24 Hours Post-Operative | | |
|---|---|---|---|---|---|---|
| | Total Nitrogen (mmol/l) | GLN*** Conc (umol/l) | Sum BCAA Conc (umol/l) | Total Nitrogen (mmol/l) | GLN*** Conc (umol/l) | Sum BCAA Conc (umol/l) |
| Saline | 4.51 ± 0.37 | 845 ± 99 | 326 ± 21 | 4.56 ± 0.29 | 742 ± 60 | 501 ± 9* |
| Amino Acids (0.624 gm N/24 hr/kg) | 4.84 ± 0.58 | 829 ± 87 | 339 ± 31 | 5.57 ± 0.61 | 631 ± 75 | 767 ± 99** |
| Amino Acids + Glutamine (0.624 gm N/24 hr/kg) | 3.86 ± 0.29 | 643 ± 36 | 297 ± 31 | 5.92 ± 0.49* | 1042 ± 88* | 592 ± 82* |

*p < 0.01, when compared to pre-operative value by paired t-test.
**p < 0.001, when compared to pre-operative value by paired t-test.
***GLN = glutamine, BCAA = branched chain amino acids.

TABLE II

Muscle Amino Acid Concentration (Mean ± SEM) (Expressed as mmol/l Intracellular Water)

| Solution Infused | Pre-operative | | | | | 24 Hours Post-Operative | | | | |
|---|---|---|---|---|---|---|---|---|---|---|
| | Total Nitrogen | GLN | Sum BCAA | Sum EAA*** | Sum NEAA | Total Nitrogen | GLN | Sum BCAA | Sum EAA | Sum NEAA |
| Saline | 69.8 ± 8.5 | 21.48 ± 3.21 | 0.437 ± 0.017 | 1.81 ± 0.23 | 40.92 ± 4.38 | 52.8 ±** 8.4 | 15.86 ±* 3.80 | 0.591 ± 0.0165 | 1.90 ± 0.32 | 31.50 ±** 4.70 |
| Amino Acids (0.624 gm N/24 hr/kg) | 65.2 ± 10.3 | 18.69 ± 3.74 | 0.471 ± 0.074 | 2.24 ± 0.29 | 39.00 ± 6.10 | 62.5 ± 9.6 | 18.20 ± 3.75 | 0.795 ± 0.144 | 2.77 ± 0.36 | 36.70 ± 5.40 |
| Amino Acids + Glutamine (0.624 gm N/24 hr/kg) | 63.5 ± 7.0 | 19.85 ± 3.17 | 0.442 ± 0.022 | 1.99 ± 0.29 | 37.50 ± 3.82 | 68.3 ± 4.4 | 21.65 ± 2.08 | 0.773 ±* 0.125 | 2.72 ± 0.22 | 39.74 ± 2.34 |

*p < 0.05, when compared to pre-operative value by paired t-test.
**p < 0.01, when compared to pre-operative value by paired t-test.
***EAA = essential amino acids; NEAA = non-essential amino acids.

TABLE III

Hindquarter Nitrogen Flux (Mean ± SEM; umol/min/kg)

| Solution Infused | 6-Hour Flux | | | 24-Hour Flux | | |
|---|---|---|---|---|---|---|
| | Total Amino Acid Nitrogen | GLN | BCAA | Total Amino Acid Nitrogen | GLN | BCAA |
| Saline | −19.05 ± 4.06* | −2.69 ± 1.07 | −1.41 ± 0.26** | −3.50 ± 12.10 | −1.71 ± 0.70 | 0.49 ± 1.51 |
| Amino Acids (0.624 gm N/24 hr/kg) | −7.70 ± 5.90 | −1.93 ± 0.59 | 1.62 ± 0.86 | −8.42 ± 2.90 | −1.24 ± 0.44 | 2.08 ± 1.53 |
| Amino Acids + Glutamine (0.624 gm N/24 hr/kg) | −6.52 ± 1.81 | −1.19 ± 0.46 | 0.28 ± 0.15 | −3.03 ± 3.75 | −0.16 ± 0.82 | 0.09 ± 0.22 |

*p < 0.05; saline different from all animals receiving 0.624 gm N/24 hr/kg.
**p < 0.01; saline < amino acids + glutamine < amino acids.
− = release
+ = uptake

TABLE IV

Nitrogen Balance (Mean ± SEM)

| Solution | Projected Nitrogen Intake (gm N/24 hr/kg) | N | Nitrogen gm/24 hr/kg | | |
|---|---|---|---|---|---|
| | | | Measured Intake | Excretion | Balance |
| Saline | 0 | 5 | 0 | 0.492 ± 0.022* | −0.492 ± 0.002** |
| Amino Acids*** | 0.312 | 2 | 0.304 ± 0.002 | 0.637 ± 0.056 | −0.332 ± 0.058 |
| Glutamine | 0.312 | 3 | 0.323 ± 0.003 | 0.709 ± 0.085 | −0.386 ± 0.086 |
| Amino Acids*** | 0.624 | 6 | 0.632 ± 0.001 | 0.684 ± 0.031 | −0.052 ± 0.031 |
| Amino Acids Plus**** | 0.624 | 6 | 0.635 ± 0.004 | 0.775 ± 0.019 | −0.140 ± 0.022 |

*p < 0.05; saline < 0.624 gm N/24 hr/kg amino acids < 0.624 amino acids + glutamine.
**p < 0.05; saline < 0.624 gm N/24 hr/kg amino acids + glutamine < 0.624 amino acids.
***PreAmine III
****One-half of nitrogen provided by PreAmine and one-half by glutamine.

Example 5

BCAA Uptake and Muscle Free Amino Acid Concentrations Predict Postoperative Muscle Nitrogen Balance To investigate the effectiveness of BCAA infusion to reduce skeletal muscle and whole body protein catabolism, amino acid formulas containing varying concentrations of BCAA were given preoperatively in this study to three groups of dogs undergoing a standard laparotomy and retroperitoneal dissection. A fourth group was given saline alone. Using hindquarter flux techniques, individual and total amino acid nitrogen exchange rates were measured and utilized in estimating skeletal muscle protein catabolism. Intracellular free amino acid concentrations were measured in percutaneous muscle biopsy samples. The work focuses on the effects of i.v. amino acid solutions containing varying concentrations of BCAA's on the regulation of skeletal muscle amino acid metabolism following a standardized surgical procedure in the dog. By measuring hindquarter amino acid flux and free amino acid concentrations in plasma and skeletal muscle during the first 24 hours following operation, it has been possible to evaluate the anticatabolic response to the infusion of BCAA's and other amino acids.

A. Materials and Methods

1. Preparation of Animals and Sequence of Study

Twenty-seven male and non-pregnant female mongrel dogs were obtained from a farm where they had been conditioned and screened for parasites. The dogs weighed between 18 and 40 kilograms and were housed for at least one week prior to study in the Harvard Medical School animal care facility. All procedures were in accordance with the guidelines of the Committee on Animals at Harvard Medical School and the Committee on Care and Use of Laboratory Animals of the Institute for Laboratory Animal Resources, the National Research Council, supra. The animals were kept in individual kennels with 24-hour light exposure and were exercised each morning. Water was provided ad libitum and a single daily feeding of Pro-Pet Respond 2000 dry dog food (Syracuse, N.Y., at least 25% protein by weight) was provided between 1:00 and 3:00 p.m. The animals were trained to rest quietly in a Pavlov sling prior to study.

All food was removed from the kennels at 5:00 p.m. the night before basal studies or operation. Basal studies were performed at 8:00 a.m. after the animal was exercised and placed in the sling. These studies consisted of the collection of a blood sample from a cannulated foreleg vein for plasma amino acid determination and a percutaneous needle biopsy of the vastus lateralis muscle performed under sodium thiopental anesthesia (Abbott, North Chicago, Ill., 5 mg/kg body weight, IV) to quantitate intracellular free amino acids. After the biopsy, with the dog still anesthetized, a 5 ml sample of arterial blood was obtained by percutaneous puncture of the femoral artery for analysis of whole blood amino acids.

The animal was allowed to recover for three days before further studies were performed. At 7:00 a.m. on the day of operation, again after an overnight fast, the animal was exercised and taken to the operating room where it was anesthetized with sodium pentobarbital (Abbott, North Chicago, Ill., 30 mg/kg body weight, IV) via a foreleg cannula. An endotracheal tube was placed and the animal was allowed to breathe spontaneously a mixture of room air and oxygen provided at 5 L/minute. The dog was placed on an operating table in the supine position and a 16-Fr. catheter was placed percutaneously into the superior vena cava via the external jugular vein. After noting the starting time, an infusion of either saline or the appropriate test amino acid solution was begun via this central catheter with an IMED pump (San Diego, Calif.). Cephalothin (Lilly, Indianapolis, Ind., 1 gram, IV) was given immediately before and upon completion of the operation. The urinary bladder was catheterized and, after discarding residual urine, a closed drainage collection was begun at the start of the infusion and carried on for 24 hours. Urine was also collected for a second 24-hour period, with the animal in a metabolic cage after termination of the IV infusion.

The abdomen and flanks of the dog were shaved, washed with soap and water, and prepped with a povidone iodine solution. The animal was sterilely draped, and the abdomen was entered via an infra-umbilical midline incision in females and a right paramedian incision in males. The bowel was retracted aside, and the retroperitoneum exposed for complete dissection around the distal aorta and inferior vena cava. The right deep circumflex iliac artery and vein as well as the right internal iliac artery were isolated. The two arteries were cannulated with specially prepared catheters consisting of a 6-cm segment of polyethylene tubing (2.08 mm O.D.) linked to 2.8 mm O.D. polyethylene tubing. One arterial catheter was positioned 6 cm proximally into the aorta via the circumflex iliac artery and the other catheter positioned one cm proximal to the aortic bifurcation, but distal to the caudal mesenteric artery, via the internal iliac artery. A third catheter was inserted into the inferior vena cava via the deep circumflex iliac vein and positioned distal to the renal vein. All catheters were secured and exteriorized through stab wounds in the right flank. The abdomen was closed in layers and the animal turned on its left side. The exteriorized catheters were cut to appropriate lengths, plugged with blunt needles, capped with intermittent injection ports (Jelco, Critikon, Tampa, Fla.), flushed with saline, filled with heparin (100 uU/ml), and buried subcutaneously. The injection ports were positioned high in the flanks, allowing easy access to arterial (aortic) and venous (vena caval) blood by percutaneous puncture.

Following these procedures, which generally took two hours, the animal was placed on its side and body temperature was maintained with blankets during recovery from anesthesia. Five hours after the start of the infusion and operation, the animal was placed in the Pavlov sling and a solution of 0.5% para-amino-hippurate (PAH) was infused at a rate of 0.7 ml/minute with a Harvard pump into the distal aortic catheter. After 40 minutes of dye infusion, three sets of simultaneous arterial and venous samples were obtained at 10-minute intervals for measurement of amino acid and PAH concentrations. The catheters were then flushed and filled with heparin. The animal was kept in the sling under constant surveillance until the hindquarter flux studies were repeated 24 hours after the start of the infusion. At this point, the first 24-hour urine collection was terminated, and a repeat percutaneous hind limb biopsy was performed on the leg not previously biopsied, again under brief general anesthesia. The infusion was then terminated and the animal placed in a metabolic cage for the second 24-hour period.

2. Infusion Solutions

All solutions were infused at the rate of 4 ml/minute/kg. Five control animals received 0.9% saline. Amino acid solutions (Table V) containing BCCA's at three different concentrations (11%, 22%, or 44% of total amino acids) were prepared by adding amino acids to an 8.5% standard amino acid formula, FreAmine III (American McGaw, Irvine, Calif.). The total BCAA infusion rates were 0.46, 0.92, and 1.84 grams/24 hours/kg, respectively. All three amino acid solutions were isonitrogenous, providing approximately 0.624 grams of nitrogen/24 hours/kg, with a constant ratio of valine to leucine to isoleucine (1:1.38:1.05). Nine animals received an 11% BCAA solution which was made by dissolving a mixture of non-essential amino acids (NEAA) in 2.13% FreAmine III to make a solution that provided 0.624 grams of nitrogen/24 hours/kg. In six animals, NEAA consisted of L-GLN alone and in three, NEAA consisted of a mixture of all of the NEAA found in FreAmine III (alanine, glycine, arginine, histidine, serine, and proline) in the same ratios as in FreAmine III. Six animals received 4.25% FreAmine III alone (22% BCAA). The final seven animals received 2.13% FreAmine III supplemented with enough BCAA's to make a 44% solution. This final formula was made isonitrogenous by adding NEAA as L-GLN alone (n=4) or a mixture of the NEAA found in FreAmine III (n=3). All solutions were sterilized by passage through a 0.22 $\mu$M filter (Millipore, Millis, Mass.) and stored overnight at 4° C. prior to administration. A 10-ml sample of each solution was taken at the end of the infusion period and stored at $-20°$ C. for analysis of nitrogen by the macro-Kjeldahl method.

3. Preparation and Analysis of Blood, Tissue, and Urine Samples

Whole blood and plasma samples were deproteinized by adding an equal volume of ice-cold 10% perchloric acid (PCA) and then centrifuging at 7000 rpm at 4° C. for 20 minutes. A 2-ml aliquot of the supernatant was buffered with 0.3 ml of 0.2M sodium acetate buffer (pH=4.90), adjusted to pH 4.75-4.90 with 5N potassium hydroxide, brought to a final volume of 4 ml with distilled water, and centrifuged again. The resulting supernatant was stored at $-20°$ C. for later batch analysis.

During the muscle biopsy procedure, a stopwatch was started at the time of tissue removal. The muscle was dissected free of fat and connective tissue and divided into two unequal portions. Multiple weights on each sample were recorded at 15-second intervals for one minute, and the initial muscle wet weight at time=0 was calculated from the best fit linear regression of weight plotted against time. The smaller sample (approximately 15-20 mg) was dried to a constant weight in an oven at 90° C., and the weight of dried fat-free solids was obtained after extraction in petroleum ether. The sample was then soaked in 250 ml of 1N nitric acid, and the chloride content was measured by titration with silver nitrate using a semi-automated titrator (Radiometer, Copenhagen). Plasma chloride was also determined by a similar method. Intracellular and extracellular water were then calculated using the chloride technique, as previously described. The second muscle sample (approximately 80-100 mg) was weighed and homogenized in 0.5 ml of ice-cold PCA using a Polytron homogenizer (Brinkmann, Westbury, N.Y.). The homogenate was centrifuged, and the supernatant was prepared for analysis by addition of buffer and by pH adjustment to pH 4.75-4.90 as described for blood and plasma samples.

Whole blood, plasma, and muscle intracellular GLN and glutamate concentrations were determined by an enzymatic microfluorometric method modified from the method of Lund (supra), or by automated high performance liquid chromatography (HPLC) after precolumn derivatization with o-phthalaldehyde (Smith et al., *J. Liq. Chromatog.* 8:1783-1795 (1985)). The two techniques yielded comparable results. Other amino acids except proline, cystine, and lysine were determined with a similar HPLC method. The concentration of PAH in the arterial and venous blood was determined spectrophotometrically following deproteinization with 5% trichloroacetic acid (Muhlbacher et al., *Am. J. Physiol.* 247:E75-E83 (1984)).

Urine excreted during the 24 hours of infusion was collected in a closed urinary drainage system and stored in acidified, refrigerated containers. Aliquots were stored frozen at $-20°$ C. for later batch analysis of nitrogen by the macro-Kjeldahl method (Peters et al., In: *Quantitative Clinical Chemistry*, Vol. II, 516-538, Williams & Williams (1932)). Another portion was centrifuged for 10 minutes at 2000 rpm and frozen for later analysis of urea and creatinine on the Technicon Autoanalyzer (Tarrytown, N.Y.).

4. Calculations and Statistical Analysis

Hindquarter bloodflow was calculated as previously described (Muhlbacher, F., et al., supra). Flux rates for the individual amino acids were calculated as the product of bloodflow and arteriovenous concentration difference. Three sets of samples were drawn at each time point, the flux was calculated for each set, and the mean of the three values was determined. Total amino acid nitrogen flux as well as plasma, whole blood, and intracellular nitrogen concentrations were calculated as the millimolar sum of the nitrogen groups of all amino acids measured. Skeletal muscle free intracellular amino acid concentrations were expressed per liter of intracellular water.

Statistical calculations were performed using a standard statistical package (Minitab, the Pennsylvania State University, State College, Pa., 1983). The results are expressed as mean $\pm$SEM. Paired and unpaired Student's t-tests were used as appropriate. Analysis of variance was used for multiple group comparisons. Regression analysis was performed using the method of least squares.

B. Results

All animals survived the operative procedure except for one dog that died shortly after administration of sodium pentobarbital, before the start of the i.v. infusion. This animal was not included in the study. Blood loss during the procedure was uniformly minimal. All sample catheters were patent at the 6- and 24-hour time points, with the exception of one venous catheter at the 24-hour time point in an animal in the 22% BCAA group.

Hindquarter bloodflow at 6 hours was 36.1$\pm$6.8 ml/minute/kg in the saline control group and was not affected by treatment (11% BCAA, 33.3$\pm$4.9; 22% BCAA, 42.4$\pm$8.8; 44% BCAA, 28.7$\pm$3.5; differences not significant). Flow at 24 hours was unchanged (57.9$\pm$10.2, 38.6$\pm$8.2; 54.9$\pm$6.5; 49.7$\pm$13.2, respectively). The tendency toward higher flow rates and increased variability at 24 hours may be attributable to greater motor activity of the animals following from anesthesia recovery.

1. Urinary Nitrogen Excretion and Nitrogen Balance

Following operation, the volume of urine excreted was comparable in the four treatment groups, although the dogs receiving saline alone tended to excrete less urine volume (Table VI). Urinary nitrogen excretion averaged 0.492±0.20 grams/24 hours kg in the saline group. The amino acid treated animals excreted 35–65% more nitrogen than the saline group, primarily in the form of urea. The dogs infused with the 22% BCAA solution excreted significantly less urea nitrogen and less total nitrogen than the 11% or 44% BCAA groups. Excretion of creatinine and ammonia was comparable in all groups.

Blood urea nitrogen and plasma creatinine were measured before and 24 hours following operation in selected animals from all groups. These concentrations were normal in all animals before operation and fell slightly or did not change postoperatively. Thus, the rate of urinary excretion of urea was similar to the rate of urea production; the higher urea production observed in the animals receiving the 11% and 44% BCAA solutions was significantly related ($p<0.05$) to the extra nitrogen provided by addition of BCAA or NEAA to the balanced amino acid mixture.

Nitrogen balance was less negative with amino acid administration; approximately 50% of the infused amino acid nitrogen was retained. Because nitrogen intake was the same in all animals receiving amino acids, the alterations in nitrogen excretion already discussed were reflected in nitrogen balance (Table VI). Thus, the animals receiving the 22% balanced amino acid solution achieved significantly greater nitrogen retention than the dogs receiving solutions containing 11% or 44% BCAA.

2. Whole Blood Amino Acid Concentrations

In the saline-treated animals, whole blood amino acid nitrogen fell at 6 hours postoperation, but returned to normal preoperative levels by 24 hours (Table VII). This transient hypoaminoacidemia was accounted for in large part by a decrease in the concentration of the non-essential amino acids (glutamine, alanine, arginine, serine, and asparagine), although significant decreases in some essential amino acids also occurred (threonine and tyrosine). In contrast, the animals receiving amino acid infusions maintained whole blood amino acid nitrogen concentrations at 6 hours postoperation. These levels increased above preoperative control levels by 24 hours ($p<0.05$).

Figure 2:
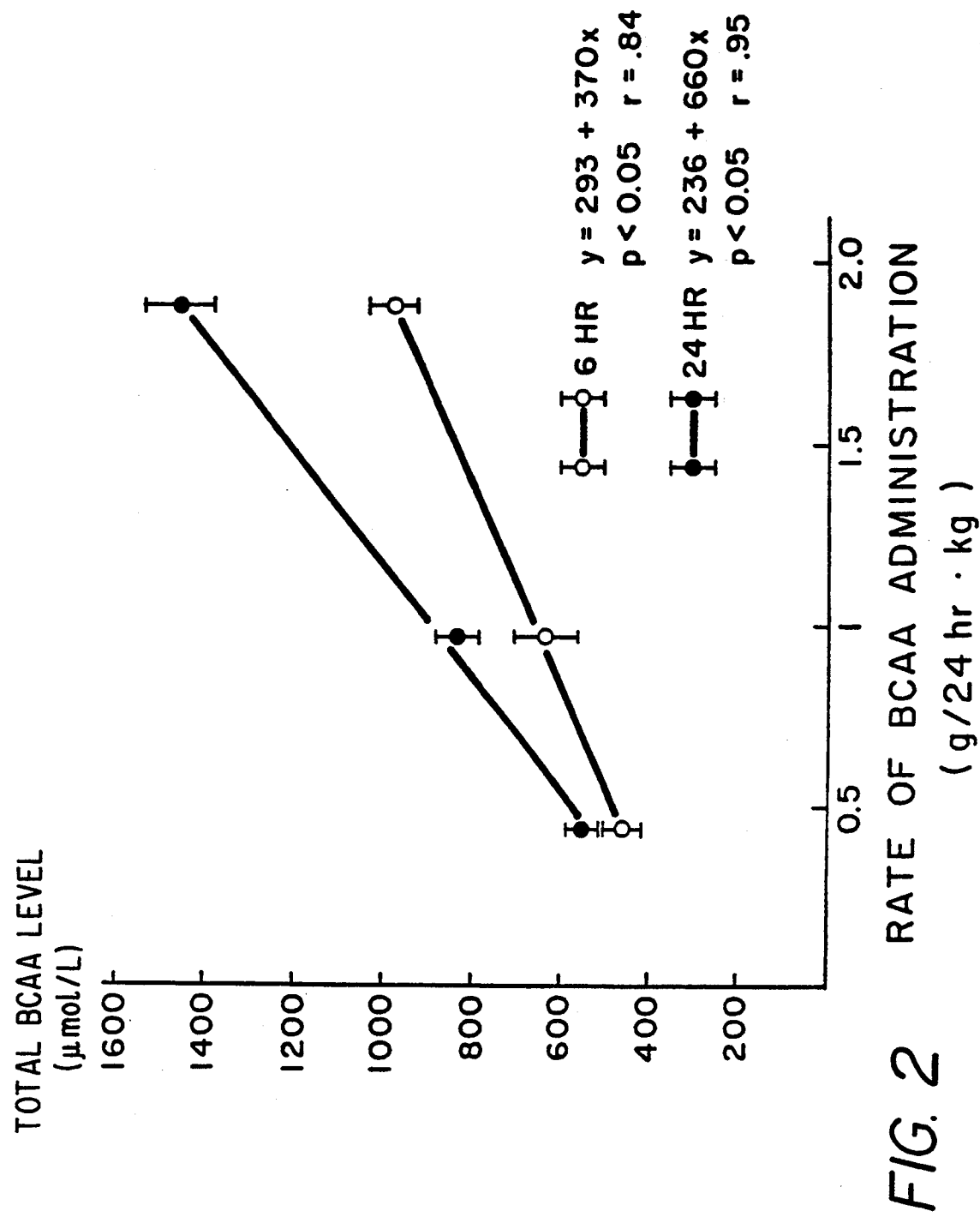
FIG. 2 is a graphic presentation of data generated in Example 5 comparing total branch chain amino acid (BCAA) level in arterial blood with the rate of administration of BCAA. Data represents mean ±SEM. Data from animals receiving saline is not included.

Concentrations of specific amino acids in the blood of the animals receiving amino acid infusions reflected the compositions of the solutions infused. For example, BCAA concentrations were related to the rate of BCAA administration at both 6 and 24 hours (FIG. 2). In general, whole blood GLN concentrations at 6 hours were lower than preoperative levels (Table VII). The exception was the group receiving GLN enriched 11% BCAA solution, in which the blood GLN concentration was maintained. In these animals, GLN comprised more than one-half of the non-essential nitrogen and accounted for more than 40% of the total amino acids delivered. By 24 hours the animals receiving GLN-containing infusions tended to have higher than normal whole blood GLN concentrations.

3. Skeletal Muscle Intracellular Free Amino Acids

In the saline-treated animals, intracellular free amino acid nitrogen fell significantly by 24 hours postoperation when compared to preoperative levels (Table VIII). This change was accounted for in large part (65%) by the marked fall in intracellular GLN, which comprised a major portion of the total intracellular free amino acid pool. In the animals receiving amino acid infusions, intracellular nitrogen was maintained, although intracellular GLN fell in the animals that received the GLN-free 11% BCAA solution. Intracellular GLN tended to increase in the animals receiving GLN-enriched solutions and BCAA concentrations increased in proportion to the rate of BCAA infusion.

4. Hindquarter Amino Acid Flux

In the saline-treated animals there was net release of amino acid nitrogen from the hindquarter at 6 hours postoperation (Table IX). This increased amino acid efflux reflected accelerated release of almost all amino acids measured, including the BCAA. At this time period, glutamate and aspartate were the only amino acids that maintained balance across the hindquarter. At 24 hours postoperation, the rate of hindquarter amino acid nitrogen release had diminished and, although highly variable, the arteriovenous differences for almost all amino acids could not be distinguished from zero. GLN efflux persisted at this time point.

Figure 3:
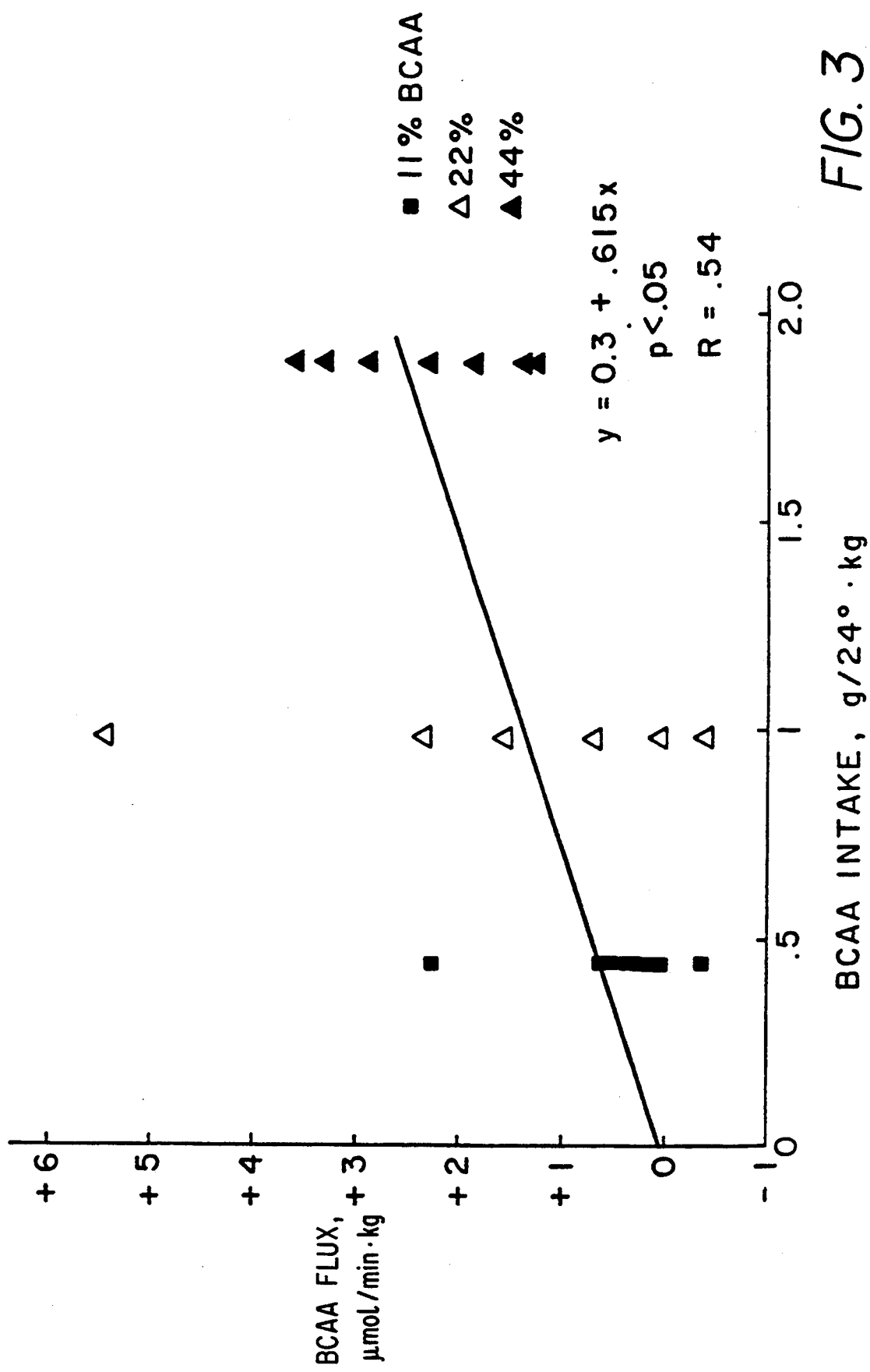
FIG. 3 is a graphic presentation of data generated in Example 5 comparing the relationship between BCAA flux (hindquarter) and BCAA infusion.
Figure 4:
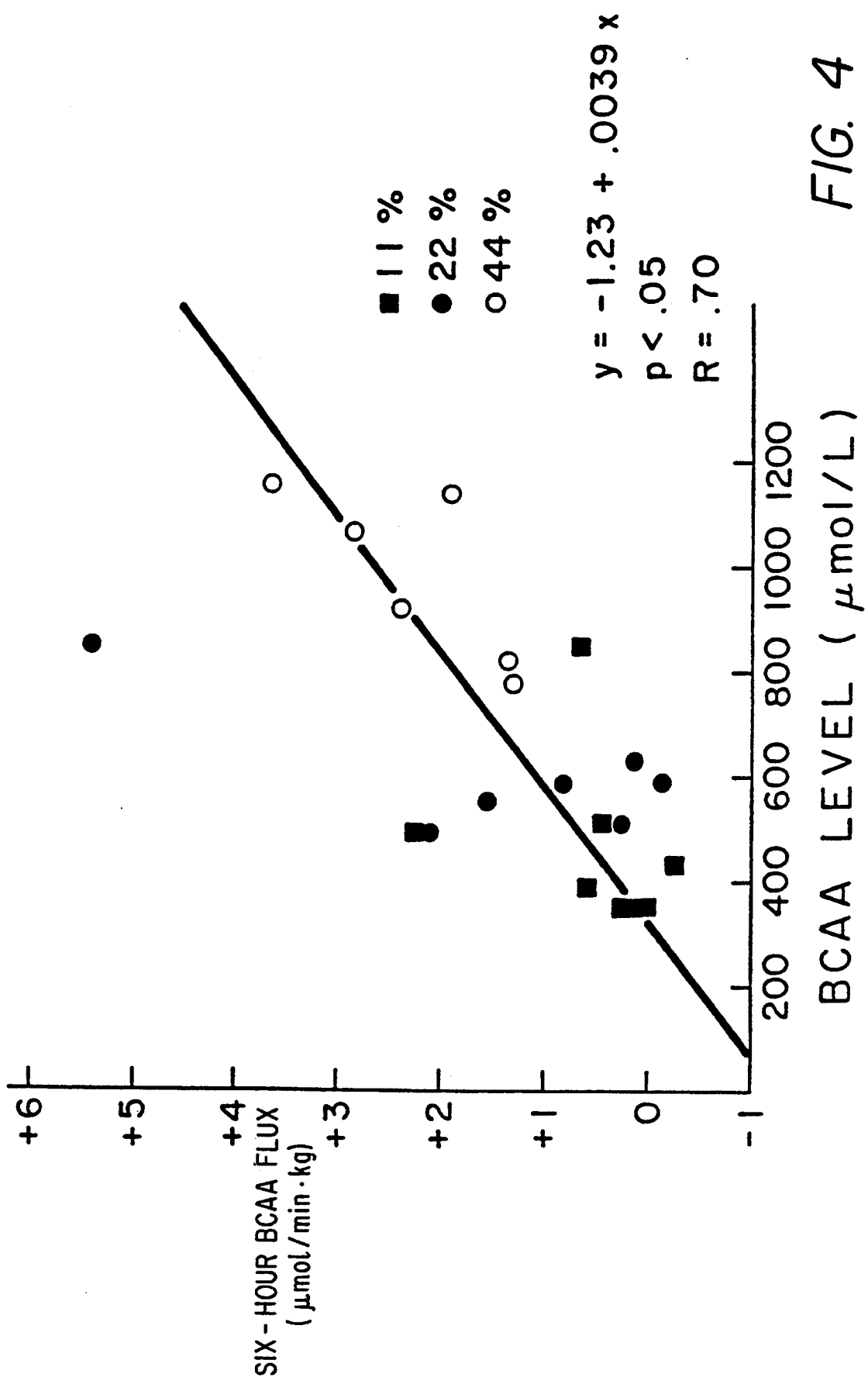
FIG. 4 is a graphic presentation of data generated in Example 5 comparing BCAA flux (hindquarters) six hours postoperative and the increase in concentration of BCAA arterial blood level.

In all groups of animals receiving amino acid infusions, hindquarter amino acid nitrogen efflux at 6 hours was similar and was significantly less than in the saline-treated animals ($p<0.05$). Both GLN and alanine efflux at 6 hours tended to be less in the animals receiving amino acids than in the saline controls. While BCAA's were released at 6 hours in the saline-infused animals, these amino acids were taken up in the dogs receiving amino acid infusions. BCAA hindquarter uptake was related to the rate of BCAA administration (FIG. 3) and whole BCAA concentrations (FIG. 4).

At 24 hours, hindquarter amino acid nitrogen efflux was similar in all the amino acid infusion groups and unchanged compared to 6 hours. At 24 hours, BCAA hindquarter exchange was slightly positive, tending to be greater in the 22% and 44% BCAA groups. At this time, BCAA uptake was unrelated to blood concentrations and rate of BCAA administration.

Figure 5:
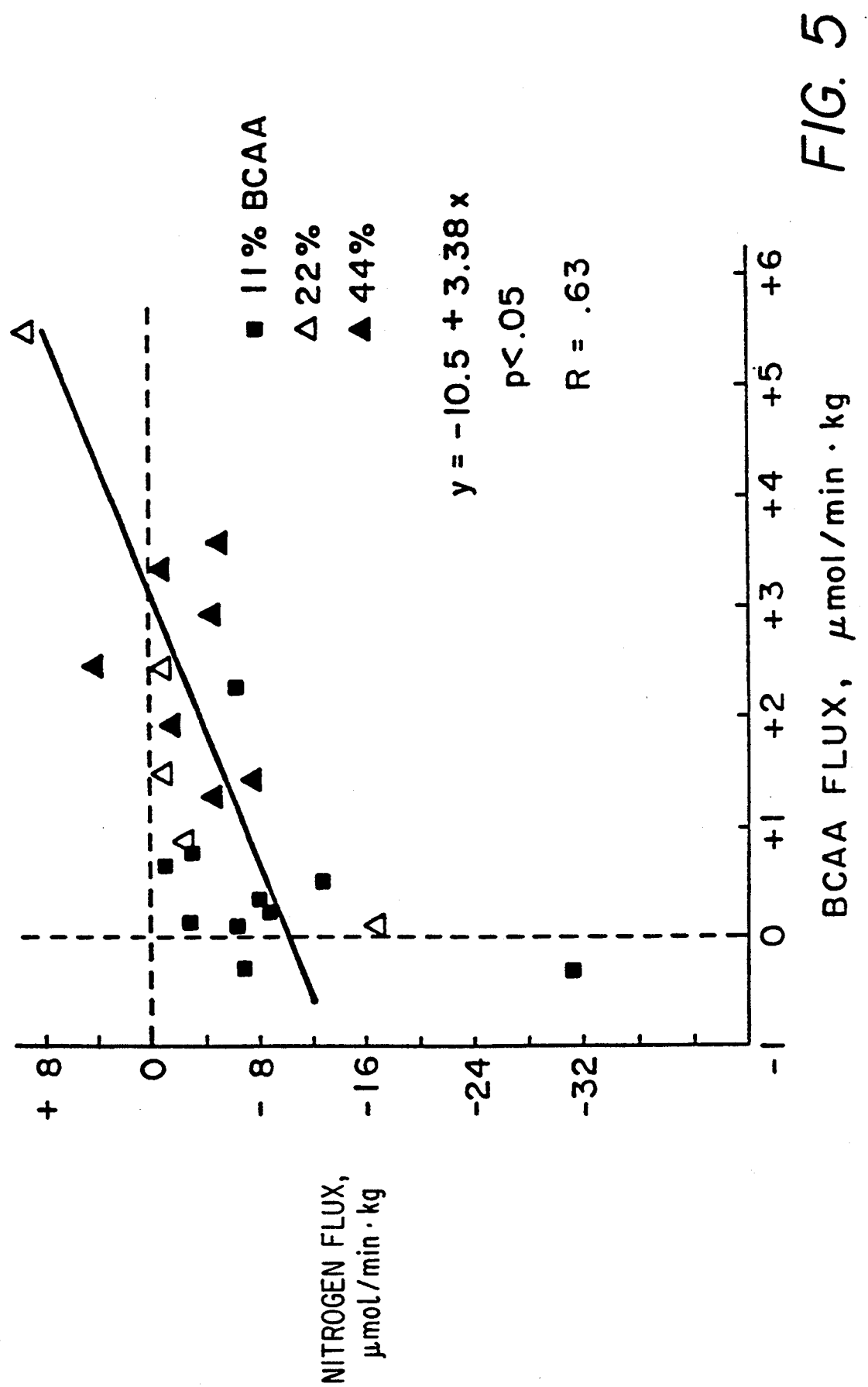
FIG. 5 is a graphic presentation of data generated by Example 5 comparing nitrogen flux (hindquarter) and BCAA flux (hindquarter) six (6) hours post-operation.

5. Relationship between BCAA Infusion, BCAA Hindquarter Uptake, and Hindquarter Amino Acid Nitrogen Release In the saline-infused dogs at 6 hours, hindquarter BCAA release was associated with accelerated amino acid efflux. In the animals receiving amino acid infusions, the hindquarter nitrogen balance correlated with BCAA uptake (FIG. 5). Saline controls were not included in this analysis since they were not receiving nitrogen; inclusion of control animals would have resulted in a regression line with a more positive slope. The correlation was maintained even if BCAA flux was not included in the summation of hindquarter amino acid nitrogen flux ($p<0.02$, $r=0.49$). Thus, nitrogen flux exclusive of BCAA flux was also related to BCAA uptake. Nitrogen flux did not correlate with total BCAA concentration in the blood or the rate of BCAA administration. None of these relationships existed at the 24-hour time point.

Figure 6:
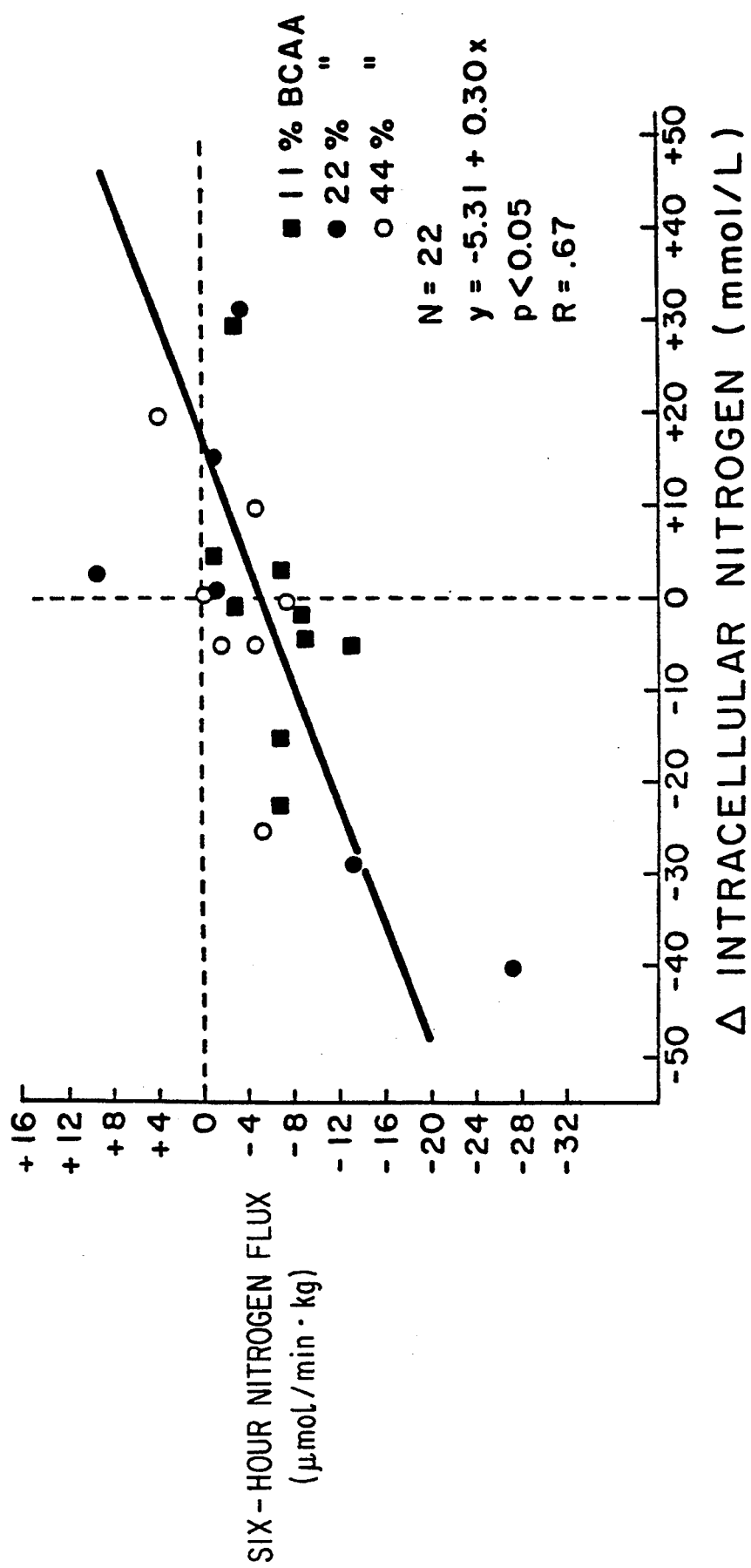
FIG. 6 is a graphic presentation of data generated in Example 5 comparing nitrogen flux (hindquarter) six (6) hours post-operation and the change in muscle intracellular amino acid nitrogen measured 24 hours post-operation.

Hindquarter amino acid nitrogen release at 6 hours also correlated with changes in the intracellular free amino acid nitrogen pool (FIG. 6). Alterations in intracellular GLN were closely related to changes in the total free amino acid nitrogen pool ($p<0.001$, $r=0.90$) and, thus, changes in the GLN pool were also significantly related to hindquarter nitrogen efflux ($p<0.05$;

r=0.66). These mathematical relationships were maintained when hindquarter amino acid nitrogen efflux was corrected for changes in the intracellular nitrogen pool. Since the flux and pool measurements were made at different points in time, we made this correction by assuming two different rates of change in the intracellular amino acid pool. First, it was assumed that the change in the intracellular pool occurred in the first 6 hours postoperatively. Alternatively, it was assumed that the change occurred at a constant rate over 24 hours. Neither correction altered the relationship between the change in the intracellular nitrogen pool and the amino acid nitrogen efflux.

BCAA uptake was not related to increased GLN release from the hindquarter at 6 or 24 hours. BCAA uptake was also unrelated to the changes that occurred in the skeletal muscle intracellular free amino acid pool (r=0.11, not significant). Hindquarter nitrogen flux could be predicted and most of the variability in the data could be accounted for when both BCAA 6-hour flux and the change in the free amino acid nitrogen pool were utilized. The relationship was:

$$y = -9.58 + 0.27x_1 + 3.02x_2$$

where
y = amino acid nitrogen flux at 6 hours, umol/min/kg
$x_1$ = BCAA flux at 6 hours (umol/min/kg)
$x_2$ = change in skeletal muscle intracellular free amino acid nitrogen (postop-preop, mmol/L/24 hours)
n=22, $p<0.05$, r=0.86

C. Discussion

A standardized laparotomy in anesthetized dogs has been shown to initiate many of the catabolic responses observed in critically ill humans. Total body protein catabolism, as measured by urinary nitrogen excretion, is increased. The control animals receiving saline excreted approximately 12-15 grams of nitrogen in the first 24 hours following operation. Prior studies in this model have demonstrated that nitrogen balance remains negative for three days following the operative procedure in spite of food intake (Kapadia et al., *Surg. Forum* 33:19-21 (1982)). In contrast, pair-fed sham-operated animals achieved nitrogen equilibrium in the first postoperative day. Consistent with and contributing to the increased urinary nitrogen loss, hindquarter release of total amino acid nitrogen at 6 hours following operation was 6 to 8 times that observed in control animals after an overnight fast (Muhlbacker et al., supra). Other changes in the saline-treated dogs, such as a decrease in blood and skeletal muscle amino acid concentrations, are similar to alterations reported during catabolic states in humans (Askanazi et al., *Ann. Surg.* 192:78-85 (1980)). Thus, the canine model exhibits postoperative responses that are similar to alterations in critically ill humans and, therefore, is suitable for examining the effects of exogenous amino acids on nitrogen metabolism and skeletal muscle amino acid exchange.

In the saline-treated animals, hindquarter release of amino acid nitrogen was markedly increased 6 hours postoperatively. This was associated with a net skeletal muscle release of all the BCAA's. At the same time, whole blood BCAA concentrations were unchanged, indicating that consumption of BCAA in visceral organs was roughly equivalent to the accelerated rate of skeletal muscle release. In the animals receiving amino acids, hindquarter total amino acid release was attenuated, whole blood and skeletal muscle nitrogen pools were maintained, the hindquarter was converted from an organ of BCAA release to one of uptake. BCAA, and more specifically leucine uptake, was not associated with increased skeletal muscle release of GLN.

This study demonstrates that skeletal muscle amino acid release and, hence, the net turnover of muscle protein, can be predicted from two independent measurements. These are the rate of BCAA flux across the skeletal muscle vascular bed and the concentration of nitrogen in the skeletal muscle free amino acid pool. Since GLN is the most abundant amino acid in the free pool, changes in its concentration largely determine changes in the total pool. In fact, changes in the free GLN predict muscle nitrogen balance as well as changes in total free amino acids.

TABLE V

Composition of Infused Solutions
(Expressed as Grams Infused/24 Hours/KG)

| Solution | | Essential Amino Acids | | Non-Essential Amino Acids | | Total Nitrogen |
|---|---|---|---|---|---|---|
| | | BCAA* | Other | Glutamine | Other | |
| Saline | 5 | 0 | 0 | 0 | 0 | 0 |
| 11% BCAA* + Glutamine | 6 | 0.46 | 0.54 | 1.64 | 1.04 | 0.62 |
| 11% BCAA* + NEAA** | 3 | 0.46 | 0.54 | 0 | 2.77 | 0.62 |
| 22% BCAA* = SAA*** | 6 | 0.92 | 1.09 | 0 | 2.07 | 0.62 |
| 44% BCAA* + Glutamine | 4 | 1.84 | 0.54 | 0.82 | 1.04 | 0.62 |
| 44% BCAA* + NEAA** | 3 | 1.84 | 0.54 | 0 | 1.90 | 0.62 |

*BCAA = Branched chain amino acids (valine, leucine, isoleucine)
**NEAA = Non-essential amino acids found in FreAmine III ® (American McGaw) (alanine, arginine, glycine, histidine, proline, serine)
***SAA = Standard amino acids supplied as FreAmine III ®

TABLE VI

Volume and Composition of 24-Hour Urinary Excretion

| Infusion | N | Volume (ml/kg) | Nitrogen Intake (g/kg) | Total Nitrogen Excretion (g/kg) | Nitrogen Balance | Urea N Excretion (g/kg) | Creatinine Excretion (g/kg) | Ammonium Excretion (g/kg) |
|---|---|---|---|---|---|---|---|---|
| Saline | 5 | 43.8 ± 10.2 | 0* | 0.492 ± .02* | −0.492 ± .02* | 0.409 ± .03* | 0.039 ± .002 | 0.037 ± .005 |
| 11% BCAA | 9 | 57.5 ± 6.9 | 0.627 ± .005 | 0.786 ± .02 | −0.160 ± .02 | 0.697 ± .01 | 0.033 ± .001 | 0.049 ± .004 |
| 22% BCAA | 6 | 64.2 ± 5.1 | 0.632 ± .001 | 0.685 ± .03** | −0.053 ± .03** | 0.603 ± .03** | 0.034 ± .002 | 0.045 ± .005 |

TABLE VI-continued

| | | | | Volume and Composition of 24-Hour Urinary Excretion | | | | |
|---|---|---|---|---|---|---|---|---|
| Infusion | N | Volume (ml/kg) | Nitrogen Intake (g/kg) | Total Nitrogen Excretion (g/kg) | Nitrogen Balance | Urea N Excretion (g/kg) | Creatinine Excretion (g/kg) | Ammonium Excretion (g/kg) |
| 44% BCAA | 7 | 74.0 ± 8.2 | 0.627 ± .003 | 0.825 ± .05 | −0.200 ± .05 | 0.701 ± .04 | 0.037 ± .002 | 0.041 ± .003 |

*Saline diff. from treatment groups, $p < 0.05$.
**Diff. from other 2 treatment groups, $p < 0.05$.

TABLE VII

Whole Blood Amino Acid Profile
(umol/l, MEAN ± SEM)

| | | | | 11% BCAA | | | | | |
|---|---|---|---|---|---|---|---|---|---|
| | Saline | | | GLN | | | NEAA | | |
| | PRE | 6* | 24* | PRE | 6* | 24* | PRE | 6* | 24* |
| GLN | 724.0 ± 55 | 565.0 ± 53 | 764.0 ± 64 | 764.0 ± 63 | 754 ± 57 | 1108 ± 110 | 808 ± 111 | 626.0 ± 20.6 | 679.9 ± 55.2 |
| ALA | 431.9 ± 42.6 | 257.9 ± 13.4 | 325.0 ± 56 | 429.0 ± 38.8 | 270.7 ± 35.1 | 290.9 ± 14.8 | 344.1 ± 18 | 364.0 ± 101 | 481.0 ± 152 |
| GLY | 414.0 ± 90 | 212.0 ± 14.5 | 239.9 ± 16.1 | 439.0 ± 57 | 419.0 ± 63 | 469.0 ± 60 | 194.3 ± 38.7 | 509.5 ± 34.4 | 595.0 ± 89 |
| ARG | 241.2 ± 27 | 152.5 ± 7.9 | 175.0 ± 9.1 | 262.1 ± 39.3 | 221.5 ± 18.2 | 265.9 ± 23.1 | 177.1 ± 29.6 | 229.8 ± 33.1 | 296.2 ± 41.2 |
| SER | 131.4 ± 9.3 | 96.8 ± 8.1 | 140.4 ± 8.4 | 166.7 ± 22.9 | 142.3 ± 5.7 | 179.3 ± 11.7 | 118.0 ± 24.8 | 222.5 ± 22.2 | 293.6 ± 36.9 |
| ASP | 29.8 ± 5.4 | 27.6 ± 4.6 | 29.3 ± 4.2 | 30.3 ± 3.7 | 25.9 ± 2.8 | 30.6 ± 3.4 | 27.1 ± 3.8 | 23.4 ± 4.1 | 22.3 ± 3.9 |
| ASN | 39.7 ± 4.9 | 26.7 ± 2.1 | 54.7 ± 2.6 | 48.0 ± 3.8 | 31.6 ± 1.1 | 50.4 ± 3.9 | 54.1 ± 8.7 | 33.1 ± 4.6 | 47.6 ± 8.0 |
| GLU | 65.8 ± 4.7 | 68.0 ± 4.1 | 72.3 ± 3.9 | 66.1 ± 4.3 | 67.1 ± 5.0 | 66.9 ± 2.6 | 66.0 ± 10.7 | 75.8 ± 11.4 | 63.6 ± 4.9 |
| HIS | 109.8 ± 8.3 | 108.0 ± 11.9 | 122.0 ± 10.1 | 105.1 ± 14.3 | 115.9 ± 10.e | 133.9 ± 10.e | 88.2 ± 6.0 | 116.8 ± 6.6 | 133.1 ± 11.9 |
| TYR | 72.8 ± 7.3 | 54.9 ± 1.2 | 66.2 ± 4.8 | 91.3 ± 24.6 | 53.3 ± 5.0 | 63.9 ± 4.9 | 52.1 ± 5.7 | 45.1 ± 0.1 | 54.3 ± 3.9 |
| TAU | 264.3 ± 39.3 | 411.0 ± 46 | 441.3 ± 29.5 | 246.0 ± 73 | 467.0 ± 58 | 474 ± 62 | 317.5 ± 45.1 | 401.3 ± 45.9 | 459 ± 65 |
| MET | 12.3 ± 0.9 | 16.6 ± 1.9 | 40.8 ± 2.6 | 42.2 ± 10.2 | 33.9 ± 6.2 | 54.3 ± 9.5 | 25.7 ± 3.0 | 20.7 ± 8.4 | 33.1 ± 6.8 |
| THR | 239.0 ± 29 | 160.5 ± 28.4 | 281.7 ± 28.7 | 264.0 ± 66 | 204.6 ± 30.5 | 306.3 ± 35.9 | 241.9 ± 24.5 | 245.2 ± 15.9 | 277.0 ± 67 |
| PHE | 44.7 ± 4.1 | 52.9 ± 4.6 | 69.3 ± 4.7 | 45.9 ± 5.4 | 74.2 ± 5.8 | 89.7 ± 5.7 | 41.9 ± 3.1 | 66.3 ± 2.0 | 82.5 ± 4.4 |
| VAL | 149.5 ± 11.3 | 143.4 ± 8.4 | 210.3 ± 13.9 | 165.9 ± 24.5 | 225.1 ± 32.0 | 250.5 ± 22.9 | 135.2 ± 16.8 | 203.9 ± 18.0 | 271.0 ± 10.2 |
| ILE | 53.1 ± 5.0 | 54.4 ± 3.8 | 85.7 ± 4.2 | 55.9 ± 5.8 | 97.3 ± 14.1 | 112.6 ± 9.5 | 45.4 ± 7.1 | 90.0 ± 9.5 | 121.6 ± 4.4 |
| LEU | 102.7 ± 7.4 | 96.2 ± 7.1 | 153.2 ± 7.3 | 105.2 ± 5.6 | 153.2 ± 29.7 | 166.6 ± 15.8 | 99.0 ± 19.0 | 140.7 ± 16.3 | 179.6 ± 5.8 |
| TOTAL BCAA | 305.3 ± 23 | 294.0 ± 17.6 | 449.3 ± 24.8 | 322.31 ± 30.9 | 475.6 ± 68.1 | 534.7 ± 51.0 | 279.6 ± 35.0 | 434.6 ± 35.7 | 562.1 ± 9.2 |
| TOTAL NITROGEN | 4.72 ± .36 | 3.82 ± .08 | 4.87 ± .20 | 5.27 ± .38 | 5.06 ± .20 | 6.69 ± .44 | 4.40 ± .50 | 5.00 ± .31 | 5.96 ± .64 |

| | | | | 44% BCAA | | | | | |
|---|---|---|---|---|---|---|---|---|---|
| | 22% BCAA | | | GLN | | | NEAA | | |
| | PRE | 6* | 24* | PRE | 6* | 24* | PRE | 6* | 24* |
| GLN | 693.0 ± 77 | 493.6 ± 29.7 | 648.7 ± 38.3 | 961.0 ± 130 | 723.6 ± 44.2 | 1040 ± 66 | 861.5 ± 40.5 | 607.0 ± 23/4 | 558.0 ± 33/5 |
| ALA | 379.0 ± 62 | 327.7 ± 38.0 | 366.0 ± 43 | 407.0 ± 55 | 242.2 ± 29.6 | 240.3 ± 9.7 | 372.0 ± 103 | 362.6 ± 49.1 | 359.1 ± 34.9 |
| GLY | 381.0 ± 67 | 521.9 ± 33.3 | 559 ± 51 | 247.0 ± 32.9 | 330.1 ± 88 | 255.4 ± 18.2 | 243.3 ± 51.4 | 376.7 ± 28.2 | 420.7 ± 16 |
| ARG | 208.9 ± 19.7 | 254.8 ± 8.3 | 323.8 ± 19.3 | 185.2 ± 17.4 | 184.9 ± 8.8 | 181.5 ± 5.6 | 191.2 ± 1.8 | 229.2 ± 15.0 | 261.9 ± 9.3 |
| SER | 126.2 ± 7.9 | 162.4 ± 11.0 | 223.9 ± 12.1 | 130.6 ± 6.3 | 135.5 ± 7.9 | 143.2 ± 11.9 | 153.6 ± 14.1 | 188.2 ± 8.9 | 226.6 ± 18 |
| ASP | 21.6 ± 1.9 | 18.9 ± 1.8 | 24.6 ± 1.3 | 39.1 ± 12.2 | 27.6 ± 2.1 | 21.7 ± 1.0 | 27.4 ± 4.1 | 24.6 ± 2.8 | 21.7 ± 1.7 |
| ASN | 37.9 ± 6.8 | 22.9 ± 2.1 | 37.1 ± 4.1 | 56.1 ± 4.7 | 32.0 ± 1.9 | 47.6 ± 3.3 | 55.6 ± 2.8 | 26.3 ± 1.0 | 38.4 ± 4.6 |
| GLU | 51.2 ± 4.3 | 51.74 ± 3.2 | 55.7 ± 2.5 | 62.0 ± 2.8 | 68.3 ± 3.9 | 59.5 ± 4.0 | 72.6 ± 9.6 | 66.4 ± 8.8 | 50.8 ± 7.4 |
| HIS | 100.3 ± 7.1 | 121.2 ± 15.6 | 136.7 ± 11.7 | 104.2 ± 5.8 | 119.9 ± 11.2 | 103.1 ± 1.6 | 92.0 ± 1.6 | 113.9 ± 2.5 | 109.3 ± 4.3 |
| TYR | 65.7 ± 5.8 | 54.2 ± 2.6 | 69.2 ± 2.6 | 63.3 ± 6.4 | 52.8 ± 5.2 | 45.9 ± 4.6 | 62.5 ± 6.6 | 45.1 ± 5.4 | 48.5 ± 4.3 |
| TAU | 248.9 ± | 327.7 ± | 430 ± | 317.8 ± | 360.4 ± | 295.5 ± | 3433.3 ± | 444.9 ± | 412.5 ± |

TABLE VII-continued

Whole Blood Amino Acid Profile
(umol/l, MEAN ± SEM)

|  | | | | | | | | | |
|---|---|---|---|---|---|---|---|---|---|
| MET | 23.5 ± 6.7 | 52.0 ± 14 | 95.4 ± 9.1 | 33.7 ± 6.6 | 14.2 ± 3.7 | 32.4 ± 13.2 | 35.0 ± 6.5 | 22.8 ± 3.7 | 43.3 ± |
|  | 32.7 | 38 | 49 | 17.4 | 48.7 | 22.6 | 31.6 | 11.6 | 32 |
| THR | 253.5 ± 29.4 | 239.7 ± 15.6 | 347.1 ± 31.3 | 227.7 ± 38.8 | 254.9 ± 34.4 | 224.4 ± 10.7 | 208.4 ± 8.2 | 185.7 ± 9.9 | 204.1 ± 18 |
| PHE | 45.5 ± 3.4 | 94.6 ± 2.1 | 103.1 ± 4.5 | 43.1 ± 2.5 | 63.5 ± 7.3 | 73.8 ± 4.9 | 37.2 ± 1.3 | 58.0 ± 3.9 | 72.9 ± 6.7 |
| VAL | 137.6 ± 17.3 | 304.1 ± 26.4 | 391.5 ± 21.3 | 128.2 ± 8.2 | 446.7 ± 42.6 | 636.8 ± 24.4 | 155.1 ± 11.3 | 513.1 ± 8.6 | 805.1 ± 10 |
| ILE | 49.6 ± 6.7 | 137.2 ± 16.8 | 175.6 ± 8.9 | 43.2 ± 4.2 | 177.0 ± 15.4 | 257.2 ± 8.7 | 57.1 ± 3.3 | 211.7 ± 8.6 | 325.9 ± 10 |
| LEU | 100.5 ± 15.4 | 196.2 ± 24.6 | 263.4 ± 16.7 | 95.1 ± 7.1 | 280.6 ± 21.6 | 420.4 ± 15.9 | 121.5 ± 1.6 | 341.2 ± 13.7 | 524.8 ± 19 |
| TOTAL BCAA | 299.1 ± 38.4 | 637.0 ± 67 | 830.0 ± 45 | 266.4 ± 15.8 | 904.4 ± 68.8 | 1314.4 ± 42.3 | 333.7 ± 12.2 | 1066.0 ± 31.2 | 1638.5 ± 49.6 |
| TOTAL NITROGEN | 4.71 ± .31 | 5.08 ± .17 | 6.31 ± .17 | 4.93 ± .28 | 5.07 ± .21 | 5.92 ± .18 | 4.76 ± .26 | 5.37 ± .10 | 6.03 ± .01 |

TABLE VIII

Skeletal Muscle Amino Acid Profile
(mmol/l, MEAN ± SEM)

|  | Saline | | 11% BCAA | | | | 22% BCAA | |
|---|---|---|---|---|---|---|---|---|
|  | | | GLN | | NEAA | | | |
|  | PRE | POST | PRE | POST | PRE | POST | PRE | POST |
| GLN | 21.48 ± 3.21 | 15.86 ± 3.80 | 19.85 ± 3.17 | 21.78 ± 2.01 | 30.25 ± 1.63 | 21.04 ± 1.92 | 18.69 ± 3.74 | 18.15 ± 3.76 |
| ALA | 5.35 ± .55 | 5.58 ± .88 | 4.81 ± .44 | 5.62 ± .39 | 5.59 ± .23 | 8.11 ± 2.35 | 4.71 ± .46 | 4.69 ± .79 |
| GLY | 2.85 ± .c31 | 2.28 ± .51 | 4.30 ± .65 | 3.22 ± .42 | 3.67 ± .37 | 3.63 ± .25 | 4.06 ± .74 | 4.52 ± 1.15 |
| ARG | 1.17 ± .24 | 0.73 ± .08 | 0.91 ± .21 | 0.78 ± .03 | 1.45 ± .41 | 2.06 ± .51 | 1.21 ± .14 | 1.14 ± .15 |
| SER | 1.42 ± .16 | 1.10 ± .19 | 1.42 ± .26 | 1.65 ± .13 | 1.52 ± .09 | 2.33 ± .22 | 2.10 ± .60 | 1.38 ± .22 |
| ASP | 0.93 ± .20 | 1.04 ± .13 | 0.50 ± .19 | 0.80 ± .19 | 1.63 ± .16 | 1.95 ± .41 | 0.85 ± .52 | 0.62 ± .15 |
| ASN | 0.43 ± .05 | 0.50 ± .07 | 0.51 ± .07 | 0.67 ± .08 | 0.53 ± .04 | 0.43 ± .06 | 0.43 ± .09 | 0.45 ± .08 |
| GLU | 6.30 ± .86 | 3.91 ± .30 | 4.48 ± .98 | 4.38 ± .84 | 11.23 ± .75 | 9.08 ± 1.25 | 5.96 ± .83 | 4.97 ± 1.30 |
| HIS | 0.81 ± .28 | 0.39 ± .02 | 0.45 ± .12 | 0.59 ± .11 | 0.69 ± .01 | 0.96 ± .14 | 0.79 ± .18 | 0.50 ± .03 |
| TYR | 0.17 ± .02 | 0.13 ± .02 | 0.27 ± .09 | 0.24 ± .05 | 0.36 ± .20 | 0.36 ± .09 | 0.32 ± .09 | 0.27 ± .05 |
| MET | 0.06 ± .03 | 0.04 ± .02 | 0.30 ± .02 | 0.06 ± .04 | 0.07 ± .01 | 0.13 ± .01 | 0.04 ± .03 | 0.06 ± .04 |
| THR | 1.20 ± .23 | 1.11 ± .17 | 1.36 ± .30 | 1.62 ± .18 | 2.24 ± .27 | 2.25 ± .21 | 1.59 ± .23 | 1.70 ± .26 |
| PHE | 0.11 ± .02 | 0.14 ± .05 | 0.11 ± .03 | 0.17 ± .02 | 0.12 ± .03 | 0.16 ± .01 | 0.09 ± .02 | 0.14 ± .02 |
| VAL | 0.19 ± .01 | 0.21 ± .04 | 0.20 ± .01 | 0.37 ± .05 | 0.20 ± .04 | 0.32 ± .04 | 0.22 ± .03 | 0.37 ± .07 |
| ILE | 0.09 ± .003 | 0.11 ± .02 | 0.09 ± .01 | 0.17 ± .03 | 0.11 ± .03 | 0.17 ± .02 | 0.10 ± .02 | 0.17 ± .03 |
| LEU | 0.16 ± .01 | 0.28 ± .12 | 0.16 ± .01 | 0.23 ± .05 | 0.18 ± .05 | 0.21 ± .03 | 0.16 ± .02 | 0.26 ± .04 |
| TOTAL BCAA | 0.44 ± .02 | 0.59 ± .17 | 0.42 ± .02 | 0.77 ± .13 | 0.50 ± .12 | 0.69 ± .16 | 0.47 ± .07 | 0.80 ± .14 |
| TOTAL NITROGEN | 69.8 ± 8.5 | 52.8 ± 8.4 | 63.5 ± 7.0 | 68.3 ± 4.4 | 96.4 ± 5.2 | 82.8 ± 5.9 | 65.2 ± 10.3 | 62.5 ± 9.6 |

|  | 44% BCAA | | | |
|---|---|---|---|---|
|  | GLN | | NEAA | |
|  | PRE | POST | PRE | POST |
| GLN | 24.83 ± 2.72 | 26.20 ± 3.86 | 22.55 ± 3.57 | 21.66 ± 2.27 |
| ALA | 5.16 ± .95 | 7.55 ± .89 | 4.45 ± .27 | 4.01 ± 1.67 |
| GLY | 3.70 ± .31 | 2.87 ± .17 | 4.08 ± .63 | 2.33 ± .82 |
| ARG | 1.06 ± .20 | 0.59 ± .13 | 1.10 ± .39 | 0.95 ± .35 |
| SER | 1.69 ± .12 | 1.63 ± .21 | 1.72 ± .32 | 1.34 ± .57 |
| ASP | 1.15 ± .12 | 2.86 ± .34 | 1.29 ± .31 | 1.69 ± .76 |
| ASN | 0.86 ± .15 | 0.60 ± .18 | 0.42 ± .09 | 0.36 ± .09 |
| GLU | 10.29 ± .83 | 9.29 ± 1.03 | 9.00 ± 2.08 | 8.98 ± 1.98 |
| HIS | 0.79 ± .14 | 0.62 ± .08 | 0.71 ± .18 | 0.46 ± .23 |
| TYR | 0.33 ± .11 | 0.22 ± .10 | 0.29 ± .11 | 0.15 ± .04 |
| MET | 0.08 ± .01 | 0.12 ± .01 | 0.06 ± .01 | 0.09 ± .01 |
| THR | 2.57 ± .48 | 2.29 ± .42 | 1.98 ± .30 | 1.43 ± .09 |
| PHE | 0.13 ± .02 | 0.16 ± .01 | 0.10 ± .01 | 0.15 ± .01 |
| VAL | 0.21 ± .03 | 0.80 ± .04 | 0.22 ± .01 | 1.01 ± .06 |
| ILE | 0.11 ± .02 | 0.27 ± .03 | 0.10 ± .003 | 0.29 ± .02 |
| LEU | 0.17 ± .02 | 0.42 ± .05 | 0.17 ± .001 | 0.44 ± .01 |
| TOTAL BCAA | 0.49 ± .07 | 1.49 ± .11 | 0.48 ± .01 | 1.75 ± .07 |
| TOTAL NITROGEN | 83.6 ± 7.0 | 85.9 ± 8.9 | 75.9 ± 11.8 | 70.8 ± 8.4 |

TABLE IX

| | Hindquarter Amino Acid Flux ($\mu$mol/min/kg, MEAN ± SEM) | | | | | | | | | | |
|---|---|---|---|---|---|---|---|---|---|---|---|
| | Saline | | 11% BCAA | | | | 22% BCAA | | 44% BCAA | | | |
| | | | GLN | | NEAA | | | | GLN | | NEAA | |
| | 6* | 24* | 6* | 24* | 6* | 24* | 6* | 24* | 6* | 24* | 6* | 24* |
| GLN | −2.69 | −1.71 | −1.19 | −0.16 | −2.10 | −1.92 | −1.92 | −1.24 | −0.73 | +0.74 | −2.00 | −4.13 |
| | ±1.07 | ±.70 | ±.46 | ±.82 | ±.62 | ±1.72 | ±.60 | ±.44 | ±.60 | ±1.76 | ±.32 | ±1.45 |
| ALA | −2.19 | −0.72 | −0.92 | −0.73 | −1.08 | −0.95 | −0.98 | −2.55 | −0.97 | −1.99 | −1.17 | −1.49 |
| | ±.52 | ±1.26 | ±.23 | ±.44 | ±.28 | ±.25 | ±.84 | ±.84 | ±.22 | ±.98 | ±.09 | ±.67 |
| GLY | −1.38 | −0.56 | −0.66 | −0.28 | −0.86 | +0.47 | −0.05 | −0.89 | −0.44 | −0.78 | −0.39 | −0.25 |
| | ±.36 | ±1.05 | ±.20 | ±.31 | ±.19 | ±.72 | ±.40 | ±.53 | ±.14 | ±.39 | ±.21 | ±.25 |
| ARG | −0.83 | +0.12 | −0.29 | −0.09 | −0.13 | +0.28 | −0.28 | −0.26 | −0.11 | −0.28 | −0.13 | ±0.02 |
| | ±.14 | ±.72 | ±.13 | ±.25 | ±.07 | ±.18 | ±.38 | ±.22 | ±.24 | ±.24 | ±0.06 | ±.16 |
| SER | −0.49 | +0.09 | −0.11 | +0.01 | −0.14 | +0.37 | −0.50 | +0.65 | −0.14 | −0.13 | −0.22 | +0.16 |
| | ±.11 | ±.49 | ±.28 | ±.23 | ±.07 | ±.29 | ±.45 | ±.50 | ±.10 | ±.22 | ±.11 | ±.06 |
| ASP | +0.04 | +0.19 | −0.01 | +0.02 | −0.00 | −0.03 | +0.02 | +0.00 | +0.03 | −0.24 | +0.01 | −0.09 |
| | ±.04 | ±.12 | ±.01 | ±.05 | ±.01 | ±.11 | ±.04 | ±.08 | .03 | ±.21 | ±.03 | ±.11 |
| ASN | −0.22 | −0.14 | −0.07 | −0.14 | −0.11 | −0.38 | −0.15 | −0.12 | −0.07 | −0.32 | −0.08 | −0.12 |
| | ±0.9 | ±.11 | ±.04 | ±.04 | ±.04 | ±.29 | ±.09 | ±.13 | ±.05 | ±.13 | ±.05 | ±.05 |
| GLU | +0.10 | +0.21 | +0.06 | +0.08 | +0.06 | +0.17 | +0.11 | +0.23 | +0.16 | +0.21 | −0.01 | −0.10 |
| | ±.18 | ±.11 | ±.07 | ±.02 | ±.07 | ±.09 | ±.06 | ±.13 | ±.04 | ±.15 | ±.03 | ±.09 |
| HIS | −0.44 | −0.19 | −0.09 | +0.08 | −0.03 | −0.05 | −0.34 | −0.24 | −0.03 | −0.25 | −0.06 | −0.03 |
| | ±.09 | ±.44 | ±.17 | ±.20 | ±.14 | ±.19 | ±.27 | ±.36 | ±.10 | ±.22 | ±.12 | ±.01 |
| TYR | −0.26 | −0.08 | −0.13 | −0.11 | −0.13 | −0.04 | −0.19 | −0.14 | −0.10 | −0.18 | −0.07 | −0.06 |
| | ±.09 | ±.40 | ±.02 | ±.04 | ±.04 | ±.08 | ±.06 | ±.05 | ±.01 | ±.09 | ±.03 | ±.00 |
| TAU | −1.05 | +0.78 | −0.23 | +0.18 | −0.27 | +1.39 | −0.08 | +0.24 | −0.08 | −0.48 | +0.21 | −0.50 |
| | ±.33 | ±2.18 | ±.28 | ±.51 | ±.10 | ±.74 | ±.61 | ±.39 | ±.15 | ±.34 | ±.07 | ±.1 |
| MET | −0.32 | −0.33 | −0.23 | −0.59 | −0.61 | −2.13 | −0.74 | −1.66 | −0.21 | −1.69 | −0.26 | −0.56 |
| | ±.09 | ±.33 | ±.11 | ±.28 | ±.40 | ±1.08 | ±.41 | ±.86 | ±.06 | ±.35 | ±.16 | ±.21 |
| THR | −1.06 | +0.72 | −0.30 | −0.27 | −0.07 | +1.28 | +0.19 | −0.13 | −0.06 | +0.57 | +028 | +0.27 |
| | ±.10 | ±.86 | ±.13 | ±.32 | ±.43 | ±.67 | ±.37 | ±.46 | ±.11 | ±.35 | ±.17 | ±.1 |
| PHE | −0.37 | −0.20 | −0.12 | −0.19 | −0.13 | −0.12 | −0.14 | −0.13 | −0.14 | −0.27 | −0.07 | −0.16 |
| | ±0.5 | ±.36 | ±.04 | ±.08 | ±.03 | ±.03 | ±.09 | ±.15 | ±.08 | ±.15 | ±.03 | ±.12 |
| VAL | −0.46 | +0.33 | +0.14 | +0.02 | +0.31 | +0.49 | +0.62 | +1.12 | +0.67 | +0.37 | ±1.34 | +1.26 |
| | ±.17 | ±.68 | ±.08 | ±.11 | ±.26 | ±.23 | ±.46 | ±1.01 | ±.23 | ±.45 | ±.17 | ±.65 |
| ILE | −0.24 | +0.12 | +0.08 | +0.06 | +0.27 | +0.42 | +0.49 | +0.39 | +0.42 | +0.51 | +.80 | +0.97 |
| | ±.03 | ±.30 | ±.02 | ±.08 | ±.19 | ±.15 | ±.21 | ±.15 | ±.04 | ±.21 | ±.07 | ±.48 |
| LEU | −0.43 | +0.04 | +0.06 | −0.08 | +0.30 | +0.50 | +0.51 | +0.57 | +0.61 | +0.69 | +1.14 | +1.44 |
| | ±.09 | ±.54 | ±.07 | ±.08 | ±.25 | ±.24 | ±.33 | ±.39 | ±.06 | ±.33 | ±.13 | ±.68 |
| TOTAL BCAA | −1.14 | +0.49 | +0.28 | −0.03 | +0.88 | +1.40 | +1.64 | +2.09 | +1.71 | +1.57 | +3.28 | +3.67 |
| | ±.26 | ±1.51 | ±.14 | ±.19 | ±.57 | ±.50 | ±.86 | ±1.54 | ±.22 | ±.83 | ±.18 | ±1.43 |
| TOTAL NITROGEN | −19.05 | −3.59 | −6.52 | −3.25 | −7.39 | −1.80 | −7.70 | −8.42 | −2.50 | −7.40 | −3.27 | −7.60 |
| | ±4.06 | ±12.1 | ±1.81 | ±3.07 | ±.52 | ±6.40 | ±5.90 | ±1.90 | ±2.50 | ±8.70 | ±1.62 | ±2.91 |

Example 6

The Effects of Glutamine Enriched Oral Diet on Small Bowel after Intestinal Resection

A. Introduction

Compensatory growth of the small intestine after partial resection involves all layers of the bowel wall, but is dominated by villus hyperplasia. Increased villous height and crypt depth are accompanied by dilation and lengthening of the intestinal remnant (Williamson, R. C. N., *N. Engl. J. Med.*, 298:1393-1444 (1978)). Small bowel resection is followed by adaptive morphological and functional changes. Oral intake has been proved to be an important stimulus in the regulation of mucosal hyperplasia after intestinal resection (levine et al., *Dig. Dis.* 21:542-545 (1976)). Luminal nutrients are important in maintaining normal mucosal growth and if oral intake is not maintained after resection of small bowel, the residual bowel loses its weight and becomes hypoplastic. Patients with short bowel after small bowel resection are supported by parenteral nutrition; their survival depends on the capacity of the residual intestinal system to adapt. The use of elemental diets and parenteral nutrition allows sufficient time for the development of intestinal adaptation and a slow return to complete oral intake (Weser, E., *Gastroenterology* 71:146-150 (1976)).

GLN is an important fuel for enterocytes, and its utilization by the intestine appears to increase after surgical stress (Souba, W. W., et al., *Surgery* 94:342 (1983)). GLN could serve as a local trophic factor promoting mucosal growth when intestinal hypoplasia develops. The purpose of the present study was to test the effects of GLN-supplemented nutrition on the growth of small intestinal mucosal cells in an in vivo experimental model system, subtotal resection, that provided both a systemic stress and a stimulus to intestinal mucosal hyperplasia.

B. Materials and Methods

1. Preparation of Animals

Male Wistar rats, weighing 175-200 gm, purchased from Charles River Breeding Laboratories, Inc., were allowed to acclimatize to the laboratory for 5 days. The rats were provided free access to water and fed with Purina chow diet. They were kept in individual cages and weighed every other day. After acclimatization, the rats with normal weight gain were randomly divided into four groups.

On the first day of study, the rats were anesthetized with intraperitoneal (i.p.) injection of pentobarbital (50 mg/kg). The abdomen was opened via a midline incision, the whole length of small intestine from the ligament of Treitz to the ileocaecal valve was exteriorized and measured twice without stretch by a long black thread. The mean of the two measurements was determined. Then two-thirds resection of the small intestine beginning 5 cm distal to the ligament of Treitz was performed by the method of Lambert (*Surgery of the Digestive System of the Rat*, Charles C. Thomas, Springfield, Ill., pp. 32-35, 413-416 (1965)). The resection margins were anastomosed end to end with 6-0 prolene. The intestine was replaced in the abdominal cavity and the abdominal wall was closed with 2-0 prolene. The control group was sham operated, undergoing transection and reanastomosis of the small intestine at the distal site, two-thirds of total length measured beginning 5 cm distal to the ligament of Treitz. Animals were placed separately in metabolic cages and, starting on the day after surgery, were pair-fed orally with a balanced control diet (−GLN) that provided adequate amounts of carbohydrate, lipid, amino acids, vitamins, and salts or a GLN-supplemented diet (+GLN) that was identical except for the substitution of GLN for a fraction of the nonessential amino acids. The GLN content was either 0 or 25% of the amino acids, which is in contrast to a normal diet, in which GLN represents ~5% of amino acids.

2. Preparation of Glutamine-Supplemented Diets

The defined oral diets contained 427 calories/100 g and included 0.2% (w/w) choline chloride, 10% corn oil, 46.9% dextrin-white, 23.4% sucrose, 5% salt mixture, 0.5% vitamin mixture. Both diets consisted of 14% amino acids, including 7.17% total essential amino acids and 6.83% total nonessential amino acids. The diet lacking GLN (−GLN) contained 0.937% each of alanine, asparagine, aspartic acid, proline and serine. The GLN-enriched diet (+GLN) contained 0.237% of these amino acids and 3.5% GLN. Thus, GLN represented 25% of total amino acids and 51% of nonessential amino acids in the +GLN diet.

3. Preparation of Tissues

After 7 days of feeding, the rats were sacrificed. They were anesthetized with i.p. injection of pentobarbital (50 mg/kg). The abdomen was opened and the incision extended to the chest cavity. Five ml of blood was drawn by puncture of the right ventricle for determination of blood ammonia and plasma GLN levels. The intestine was harvested immediately following blood withdrawal. The entire small intestine was removed with careful separation of the mesentery, keeping close to the intestinal serosa. The removed intestine was suspended under fixed tension of 4.5 gm, and 9 points were marked. For the rats with bowel resection, points of 5, 10 and 12.5 cm proximal to the anastomosis which represented the proximal jejunum and distal duodenum, and points of 2, 5 and 10 cm distal to the anastomosis which represented the residual proximal ileum close to the anastomosis, and points of 5, 10 and 15 cm proximal to the ileocaecal valve which represented the residual distal ileum, were marked with straight pins passed through the bowel. The six intestinal segments were separated. For the rats in sham-operated group, the proximal two segments were marked from 1 cm distal to the ligament of Treitz and measured upward. Segments 1a, 2a and 3a were rinsed in chilled saline and embedded in 10% buffered formalin for 4 hours, then transferred into 70% ethanol for fixation. Segments 1b, 2b and 3b were rinsed in chilled saline, their lumens were opened and were weighed wet weight. The intestinal segments were transferred into 5 ml of chilled saline and minced with sharp scissors. A homogenate was prepared, using two fifteen second periods on a Polytron homogenizer (Brinkman Instruments, Westbury, N.Y.), followed by sonication with a sonicator (Heat System Laboratories, Plainview, N.Y.) at a power setting of 2, for thirty seconds. Saline homogenates for DNA and protein analysis were stored at −30° C.

4. Analytic Methods

The intestinal homogenates were analyzed for total protein by the Lowry method. DNA was determined according to the method of Burton (Biochem 62:315-323 (1965)). Histologic sections were embedded in paraffin, stained with hematoxylin and eosin, and examined under a light microscope at 40× magnification. Twenty representative, tall, well-oriented complete villi were chosen to measure mucosal thickness and villous height using an eyepiece micrometer, and an average value obtained. The villus number was counted with the intestine put in the central horizontal line of 40× magnified field.

C. Results

During the first 5 days, there was a progressive increase in food consumption from 10 gm/day to 15 gm/day and, thereafter, food intake remained constant. In spite of identical intake of the 2 diets in the pair-fed animals, the rate of weight gain in the 2 groups was different in the immediate post-operative period. In the control animals, body weight remained constant for the first 3 post-operative days and thereafter increased linearly at the rate of 5 gm/day. In the GLN-fed group, there was no lag period, but an immediate and continuous weight gain at 5 gm/day starting on the first post-operative day. On the 2nd and 3rd post-operative days, body weight was significantly higher in the GLN-fed group than in the control group ($p<0.05$). Although body weight increased subsequently at the same rate in animals on both diets, the greater body weight in the GLN-fed group persisted through the 8th post-operative day ($32.0\pm0.2.8$ vs. $23.7\pm3.7$ g cumulative weight gain, $p<0.03$). Carcass analysis indicated that the increase in weight did not result from the accumulation of total body water ($71\pm1\%$ in +GLN vs. $73\pm1\%$ in −GLN controls), but was an effect of GLN on lean body mass. The relationship between GLN concentration in the diet and body weight change during the first 3 post-operative days was studied in additional animals. Approximately 25% of dietary amino acids were required as GLN for a maximal growth effect.

The increase in body weight with the 25% GLN-supplemented diet was associated with increased weight of the residual segments of jejunum and ileum. On the 3rd post-operative day, the total small intestinal tissue weight was $3.55\pm0.16$ g in the GLN-fed group and $2.97\pm0.10$ g in the control animals ($p<0.05$). On the 8th post-operative day, intestinal weights were $3.30\pm0.23$ and $2.81\pm0.16$ g, respectively ($p<0.05$). The increase in intestinal weight accounted for only 5% of the total change in body weight on the GLN supplemented diet and, thus, the effect of GLN feeding included but was not limited to the intestine.

The cellularity of the jejunum and ileum was more directly assessed by determining the DNA content and by quantitative histology (Table X). With GLN feeding, there was a significant increase in DNA content in the jejunum on the 3rd day and the ileum on both the 3rd and 8th days after operation. In comparison with non-operated control animals, the combination of resection and the feeding of a nutritionally adequate, GLN supplemented elemental diet resulted in a 54% increase in jejunal DNA content per cm on the 3rd post-operative day. This adequate hyperplasia was decreased nearly by half if GLN in the diet was replaced with a balanced mixture of nonessential amino acids. Histologic measurements of mucosal thickness generally confirmed the findings on DNA content (Table X). With the GLN supplemented diet, an increase in mean villus height in the jejunum and ileum was evident on the 3rd and 8th post-operative days. This response was limited to the villi, with no GLN effect on either crypt depth or on the thickness of the submucosal muscularis layer.

TABLE X

|  | 0 GLN (n = 10) | 2% GLN (n = 11) | 3% GLN (n = 10) | CHOW (n = 11) |
|---|---|---|---|---|
| Plasma GLN (umol/L) | 890.3 ± 42.4 | 1105.8 ± 98.8* | 717.1 ± 46 |  |
| Full Thickness WT (mg/cm) | 30.6 ± 0.8 | 31.4 ± 1.0 | 32. ± 0.6 | 46.6 ± 3.6 |
| Mucosal WT (mg/cm) | 17.7 ± 0.7 | 20.4 ± 1.1** | 20.3 ± 1.0** | 29.3 ± 2.3 |
| Jejunal DNA (ug/cm) | 252.8 ± 9.5 | 279.9 ± 7.3** | 303.1 ± 19.4* | 370.2 ± 33.0 |
| Mucosal DNA (ug/cm) | 101.75 ± 5.9 | 134.0 ± 7.1*** | 125.1 ± 7.6** | 171.0 ± 12.7 |
| Villus HT (um) | 266.5 ± 8.4 | 294.0 ± 7.9** | 306.4 ± 9.9*** | 405.6 ± 17.3 |
| Mucosal Thickness (um) | 422.6 ± 9.7 | 448.1 ± 8.9* | 452.6 ± 11.5* | 589.6 ± 20.9 |

*p < 0-.05, p < 0.025, *p < 0.005 vs 0 GLN
GLN = glutamine

The effect of GLN on villus height was maximal when GLN represented 25% of the total weight of amino acids and thus 51% of the nonessential amino acids in the diet. At lower concentrations, a consistent effect in both the jejunum and ileum was not evident. When GLN content was increased to 31.25% and other nonessential amino acids were further decreased, the trophic effect on the intestinal mucosa was lost. This apparently results from such extensive alteration of the amino acid composition of the diet to accommodate GLN that other amino acids become limiting. Provision of GLN as 25% of total amino acids resulted in a modest but significant increase in plasma GLN concentrations (800+40 vs. 654±48 μM on day 3 and 751±22 vs. 676±21 μM on day 8). There was no increase in plasma levels of glutamic acid or ammonia. Thus, a diet in which GLN represented 25% of the total amino acids led to more rapid post-operative weight gain and intestinal mucosal hyperplasia with no evidence of GLN excess or the accumulation of end products of GLN metabolism such as ammonia or glutamic acid.

Because it is often difficult to deliver adequate amounts of enteral nutrients to patients who require nutritional support, especially when the underlying disease process is associated with significant involvement of the gastrointestinal tract, we evaluated the effects of GLN provided as a component of a nutritionally inadequate diet. Rats were subjected to the same 60% intestinal resection procedure and then were pair-fed control or GLN-supplemented diets which provided adequate amino acids, vitamins, and salts equivalent to the complete diet but 50% fewer total calories. After 7 days on the calorie restricted diets, there was slightly greater body weight in the GLN-supplemented group, but little weight change with either diet. In spite of the caloric deficit, the marked GLN effects on the intestinal mucosa were still evident (Table XI). On the 7th post-operative day, mucosal wet weight was increased by 36% in the jejunum and 40% in the ileum with the GLN-supplemented diet in comparison with the control diet. Mucosal DNA content was increased by 48% and 32%, respectively. These measurements of mucosal cellularity were confirmed by quantitative histologic studies, which demonstrated consistent increases in mucosal thickness in the jejunum and ileum. Even in the setting of caloric deficiency, dietary GLN exerted its trophic effects and specifically supported growth of the intestinal mucosa.

TABLE XI

Effect of GLN as a component of a 50% calorie-restricted defined oral diet on residual intestinal segments after 60% small intestine resection.

|  | −GLN | +GLN |
|---|---|---|
| Mucosal Weight (mg/cm) |  |  |
| Jejunum | 35.2 ± 2.9 | 51.7 ± 4.5** |
| Ileum | 32.7 ± 2.7 | 48.5 ± 3.8*** |
| Mucosal DNA (μg/cm) |  |  |
| Jejunum | 180 ± 12 | 266 ± 15* |
| Ileum | 217 ± 22 | 287 ± 22*** |
| Mucosal Thickness (μM) | 826 ± 61 | 1042 ± 27** |
| Jejunum | 799 ± 27 | 925 ± 40* |
| Ileum |  |  |

Intestinal segments were obtained and analyzed as described in the legend to Table X. Data represent mean ± SEM for 10 pairs of animals studied 7 days after partial intestine resection. −GLN = 0% glutamine, +GLN = 25% GLN; *p < 0.05, p < 0.01, *p < 0.001, + GLN vs. −GLN by unpaired t-test.

The effects of GLN also were evident when GLN was provided intravenously. When rats were maintained on total parenteral nutrition (TPN) for 7 days after partial intestinal resection using a GLN-free formula designed to support optimal growth in the rat (Popp, M. B., et al., Am. J. Clin. Nutr. 36:1119 (1982), villus height decreased in the jejunum and remained unchanged in the ileum (Table XII). Thus, the trophic stimulus of partial small intestine resection

TABLE XII

Effect of GLN as a component of an IV total parenteral nutrition formula on residual intestinal segments after 60% small intestine resection.

|  | Pre-resection | | 7 Days Post-resection | |
|---|---|---|---|---|
|  | −GLN | +GLN | −GLN | +GLN |
| Villus Height (μM) |  |  |  |  |
| Jejunum | 478 ± 15 | 481 ± 13 | 383 ± 22 | 588 ± 35** |
| Ileum | 400 ± 24 | 419 ± 13 | 372 ± 38 | 488 ± 16* |

Data represent mean ± SEM for 9 pairs of animals. −GLN = 0% glutamine, +GLN = 23% glutamine. *p < 0.05, **p < 0.001, +GLN vs. −GLN by unpaired t-test. p < 0.05 Pp 0.005, post-resection vs. pre-resection by unpaired t-test.

was offset by the consequences of removing food from the lumen of the GI tract (Levine, G. M., et al., Gastroenterology 67: 975 (1974). Addition of GLN to the TPN formula in place of a fraction of the nonessential amino acid component (25% of total amino acids), restored the post-resection hyperplastic response (Table XII). In comparison with the GLN-free TPN formula, villus height was increased by 54% and 31% in the jejunum and the ileum, respectively. Consistent with these animal data, the addition of the dipeptide L-alanyl-L-glutamine to an intravenous feeding regimen in a recent human study was shown to improve postoperative nitrogen balance (Stehle, P., et al., *Lancet* i:231 (1989)).

D. Discussion

These observations with GLN-supplemented oral and intravenous diets are compatible with the hypothesis that the nonessential amino acid GLN becomes an essential nutrient following operative stress and intestinal resection. When included as a component of a balanced, defined oral diet, GLN exerts a generalized anabolic or anti-catabolic effect on body tissues and prevents the transient period of weight loss associated with the stress of operation. In the intestine, which is a tissue that normally utilizes GLN at a high rate and is known to increase its GLN extraction in response to stress, a clear trophic effect of GLN on the mucosa is evident. This results in an increase in the adaptive hyperplastic response to partial small intestinal resection, with increased villus height secondary to an expanded population of enterocytes. The increase in intestinal cellularity occurs even when total caloric intake is inadequate or when all nutrients are administered by the intravenous route.

The mechanisms of these effects are unknown. GLN could have regulatory effects on specific biochemical pathways, serve as a fuel or biosynthetic precursor, act as a secretagogue, or perform all of these functions. Whatever the specific mechanism, these studies provide evidence that GLN is a necessary nutrient to support growth of the intestinal mucosa. The increase in lean body mass following intestinal resection indicates that GLN may also have anabolic effects on muscle and other tissues. Taken together, the experimental data support the hypothesis that GLN is a conditionally essential nutrient during periods of stress. The endogenous production of GLN appears to be inadequate, resulting in a fall in plasma and tissue concentrations and associated changes in tissue morphology. The provision of exogenous GLN restores free GLN concentrations and stimulates a trophic response that includes effects on the intestinal mucosa and overall growth.

Example 7

Preservation of Small Bowel Mucosa Using Glutamine-Enriched Parental Nutrition Parental nutrition results in mucosal atrophy of the small intestine (Johnson, L.R., et al., *Gastroenterology* 68:1177-1183 (1975)). This response may be related to a decrease in gastrointestinal secretions and trophic hormones and also a relative lack of specific nutrients required for enterocyte proliferation. GLN is a major oxidative fuel for the small intestine but is not present in standard parenteral solutions. To determine the influence of dietary GLN the small intestinal response to the administration of parenteral solutions enriched with varying concentrations of this amino acid was evaluated.

A. Materials and Methods

Conditioned male Wistar rats (n=42, wt 210-230 g) underwent jugular venous catheterization and were fitted with a swivel assembly which allows long term infusion in unrestrained animals (Burt, M.E., et al., *J. Physiol.* 238:H599-603 (1980)). All rats were housed in individual metabolic cages and allowed access to drinking water. Control animals received 0.9% saline infusion and Purina rat chow ad libitum. Three groups of rats received i.v. nutrition. All nutrient solutions were isonitrogenous (0.9 g nitrogen/100 ml) and isocaloric (98K cal/100 ml), and contained equal concentrations of essential amino acids, nonessential amino acids and dextrose. The nonessential amino acid component of each solution was adjusted in order to provide GLN concentrations of 0.1 or 3 g/100 ml. Parenteral solutions were infused at a rate of 48 ml/24 hrs. Urine output and nitrogen excretion were measured daily. Animals were sacrificed following 7 days of parenteral nutrition and blood was obtained for determination of GLN and ammonia concentrations. Both full thickness jejunal segments and mucosal samples were obtained from defined sections of the intestine. All samples were weighed, and homogenates were assayed for DNA and protein. Histologic paraffin sections of 5 um were prepared. Measurements of jejunal villus height, number and mucosal thickness were performed in a blinded fashion.

B. Results and Discussion

Wet weight, DNA, protein and villus height decreased in all rats receiving i.v. nutrition when compared to orally fed controls (Table XIII). Plasma GLN concentration increased following infusion of solutions containing GLN. Jejunal mucosal weight increased significantly when compared to rats receiving GLN free solutions. Full thickness jejunal weight did tend to increase with GLN intake although the response was not statistically significant. Both mucosal and full thickness jejunal DNA increased following GLN infusion at 2 and 3% concentrations. These changes were accompanied by histological evidence of mucosal growth. Villus height and mucosal thickness increased in a dose dependent manner in proportion to quantity of GLN administered. All animals were in positive nitrogen balance but rats receiving the 2% GLN solution retained the greatest quantity of nitrogen throughout the study.

The provision of GLN in parenteral solutions results in an increase in jejunal mucosal weight, DNA content and villus height when animals are maintained on i.v. nutrition. An increase in the mucosal mass of the small intestine may improve small bowel function and facilitate the introduction of enteral nutrition. GLN may be a nutrient necessary for mucosal support which is not present in standard parental solutions at the present time.

TABLE XIII

|  | 0 GLN (n = 10) | 2% GLN (n = 11) | 3% GLN (n = 10) | CHOW (n = 11) |
|---|---|---|---|---|
| Plasma GLN (umol/L) | 890.3 ± 42.4 | 1105.8 ± 98.8* | 717.1 ± 46 | |
| Full Thickness WT (mg/cm) | 30.6 ± 0.8 | 31.4 ± 1.0 | 32. ± 0.6 | 46.6 ± 3.6 |
| Mucosal WT (mg/cm) | 17.7 ± 0.7 | 20.4 ± 1.1** | 20.3 ± 1.0** | 29.3 ± 2.3 |
| Jejunal DNA (ug/cm) | 252.8 ± 9.5 | 279.9 ± 7.3** | 303.1 ± 19.4* | 370.2 ± 33.0 |

TABLE XIII-continued

|  | 0 GLN (n = 10) | 2% GLN (n = 11) | 3% GLN (n = 10) | CHOW (n = 11) |
|---|---|---|---|---|
| Mucosal DNA (ug/cm) | 101.7 ± 5.9 | 134.0 ± 7.1*** | 125.1 ± 7.6** | 171.0 ± 12.7 |
| Villus HT (um) | 266.5 ± 8.4 | 294.0 ± 7.9** | 306.4 ± 9.9*** | 405.6 ± 17.3 |
| Mucosal Thickness (um) | 422.6 ± 9.7 | 448.1 ± 8.9* | 452.6 ± 11.5* | 589.6 ± 20.9 |

*p < 0.05, p < 0.025, *p < 0.005 vs 0 GLN
GLN = glutamine

Example 8

Effect of Glutamine-Enriched Parenteral Nutrition Following Treatment With 5-Fluorouracil To determine whether GLN-supplemented parenteral nutrition was advantageous in the preservation or repair of the intestinal mucosa following injury, GLN-enriched nutrition was administered for four days preceding, and immediately following, treatment with increasing doses of 5-flurouracil (5FU), a chemotherapeutic agent which has marked toxicity on the GI mucosa in animals and in man (Muggia et al., 1963; Roche et al., 1970; Bounous et al., 1977; Stanford et al., 1977; Shaw et al., 1979).

A. Materials and Methods

1. Preparation of Animals

Rats were prepared and housed essentially as described in Example 6 and Example 7 above and were randomized into groups to receive parenteral nutrition solutions containing 0 or 2 g GLN/dl.

2. 5-FU Induced GI Injury and GLN Infusion

Rats were catheterized as previously described and after a minimum of 3 hr following recovery from anesthesia, groups of animals received 100, 150 or 200 mg/kg of 5-FU by i.p. injection. A control group received injections of 0.9% saline (0 mg/kg of 5-FU) Each dose group received either 0 or 2% GLN. The nutrition infusion, started 4 hr after 5-FU or saline, was continued for 4 d. at a rate of 46 ml/24 hr. These times were chosen because studies have shown that mucosal recovery from 5-FU damage is underway at this stage (Roche et al., 1970), GLN effects on mucosal regeneration are likely to be seen at this time.

3. GLN Feedings before Induction of Intestinal Injury

Following catheterization, rats received half-strength nutrition for 12 hr and full-strength nutrition (0 or 2 g GLN/dl) for the subsequent 8 d. The 5-FU was administered i.p. on the fourth day of parenteral feeding and the rats sacrificed four days later. A single dose of 5-FU (150 mg/kg) was chosen since induces general malaise and severe intestinal injury without increasing mortality. Urinary nitrogen excretion was measured daily and nitrogen balance calculated.

4. Tissue Sampling

Blood and intestinal tissue were sampled and prepared for analysis as described in the examples above. The hemoglobin, white blood cell and platelet numbers were determined as measures of the general hematological toxicity of the various doses of 5-FU.

5. Analytical and Statistical Methods

All analyses were performed as previously described in Examples 6 and 7. Statistical analyses were performed using two-way analysis of variance comparing both diets and dose of 5-FU. Unpaired t tests were used to compare two treatment groups at one dose of 5-FU. Differences were considered statistically significant at a p value of <0.05.

B. Results

1. Effects of Parenteral Feeding After Injury

Animals were generally well for about 36 hr following 5-FU injection, after which time they became lethargic. Five of 60 animals entered into the study were excluded for technical reasons (non-functioning catheters or infusion pump failure) and 6 died from 5-FU treatment (2 from the GLN-fed group and 4 from the control group.) Of the 49 rats that were analyzed, 23 had received 0 GLN and 26 had received 2% GLN.

a. Intestinal Indices

Jejunal wet weight, DNA, and protein all decreased following 5-FU administration. However, all these measures were significantly higher in animals receiving GLN compared with the non-GLN controls; this difference was considerably greater for the mucosal measurements of weight, DNA and protein (Tables XIV and XV). Microscopic examination demonstrated preservation of intestinal architecture in the GLN rats, reflected in the measurements of mucosal thickness and villus height (Tables XIV and XV).

b. Hematology

While hemoglobin levels were maintained at all doses of 5-FU, there was a marked decline in the circulating white blood cell and platelet counts in all drug-treated animals independently of the dietary regime employed (Tables XIV and XV).

2. Effects of Parenteral Feeding Before Injury

In contrast to rats given parenteral feeding after 5-FU, here there was a noticeably increased rate of mortality: 6 of 12 animals in the 0 GLN group died compared to 2 deaths out of 12 in the GLN-fed group. This difference was statistically significant only at the p=0.06 level (Fisher exact test).

a. Intestinal Indices

Jejunal and mucosal wet weight was significantly higher in the GLN-fed animals, as was mucosal DNA and protein, but full thickness DNA and protein did not differ in the two groups (Tables XIV and XV). Histological analysis confirmed the biochemical findings with increased mucosal thickness and villous height in the animals receiving GLN.

b. Hematology

No differences in hematological parameters were detectable in either group: hemoglobin was maintained while white cell and platelet counts dropped independently of the diets (Tables XIV and XV).

3. Plasma GLN and Amino Acids Following 5-FU

Plasma GLN was elevated in all animals following 5-FU administration, even when GLN was not present in the diet. Increased release of GLN from muscle in this catabolic state, combined with decreased cellularity of the intestine (and possibly some degree of 5-FU-induced renal toxicity) may account for the increase in circulating GLN levels.

4. Nitrogen Balance

Improved nitrogen retention had been demonstrated in animals receiving 2% GLN in the initial series of studies. Similar changes were noted in animals that received GLN-supplemented parenteral nutrition before 5-FU treatment. Daily nitrogen balance was significantly greater in the GLN-fed group up to the sixth day of feeding. Cumulative nitrogen retention in the 2% GLN rats was 1106±85 mg nitrogen compared to 736±149 mg for the 05 GLN rats ($p<0.05$).

Patients were randomized into one of two groups: standard or GLN containing TPN. The diets were isonitrogenous and isocaloric but contained 0 GLN in the standard formula and 0.57 g GLN/kg body weight/day in the experimental solution. The patient, bone marrow transplant physicians and the investigators who see the patients were blinded as to treatment group. Under this design, the electrolyte requirements for individuals may vary over time depending on the clinical conditions and the physician may vary the electrolyte content of the solution depending on blood levels and clinical status in consultation with the investigators and Nutrition Support Service.

Patients took oral nutrient ad libitum throughout the

TABLE XIIV

| | Intestinal and Hematological Indices in Animals Receiving Parenteral Nutrition After Injury | | | | | | | | | |
|---|---|---|---|---|---|---|---|---|---|---|
| Dose of 5-FU (mg/kg) | 0 | | 100 | | 150 | | 200 | | | |
| Glutamine in TPN | 0% | 2% | 0% | 2% | 0% | 2% | 0% | 2% | p value* | |
| No. of Animals | 7 | 8 | 4 | 5 | 6 | 6 | 6 | 7 | Diet | Dose |
| Hemoglobin (g/dl) | 13.0 | 12.4 | 12.2 | 12.6 | 11.6 | 13.0 | 12.3 | 12.5 | NS | NS** |
| White cell count ($10^9$/l) | 9.0 | 7.8 | 2.8 | 4.2 | 1.8 | 2.5 | 3.4 | 3.6 | NS | <0.001 |
| Platelets ($10^9$/l) | 809 | 854 | 365 | 369 | 140 | 146 | 412 | 261 | NS | <0.001 |
| Plasma glutamine ($\mu$mol/l) | 819 | 1028 | 1103 | 1050 | 1054 | 1250 | 1060 | 1016 | NS | NS |
| Jejunal wet weight (mg/cm) | 33.8 | 38.9 | 32.8 | 34.2 | 30.4 | 34.6 | 32.6 | 37.0 | <0.01 | <0.05 |
| Jejunal DNA ($\mu$g/cm) | 232 | 246 | 193 | 206 | 184 | 216 | 178 | 246 | <0.05 | NS |
| Jejunal protein (mg/cm) | 33.3 | 3.7 | 3.3 | 3.2 | 2.6 | 3.3 | 2.9 | 3.5 | <0.05 | NS |
| Mucosal wet weight (mg/cm) | 21.9 | 27.6 | 17.9 | 26.0 | 15.6 | 21.9 | 20.7 | 24.7 | <0.001 | <0.01 |
| Mucosal DNA ($\mu$g/cm) | 136 | 181 | 120 | 166 | 80 | 117 | 120 | 142 | <0.001 | <0.001 |
| Mucosal protein (mg/cm) | 1.9 | 2.4 | 1.4 | 2.2 | 1.3 | 2.0 | 1.5 | 1.9 | <0.01 | <0.05 |
| Mucosal thickness ($\mu$) | 551 | 616 | 496 | 555 | 457 | 525 | 463 | 495 | <0.05 | <0.05 |
| Villous height ($\mu$) | 356 | 422 | 300 | 360 | 247 | 320 | 239 | 299 | <0.05 | <0.05 |

*Using two-way analysis of variance comparing diets and doses of 5-FU.
**NS = not significant.

Example 9

Effect of Glutamine-Enriched Parenteral Nutrition Following Radiation, Chemotherapy, and Bone Marrow Transplantation This study was performed to determine in a randomized, blinded clinical trial whether the provision of dietary GLN to patients undergoing total body irradiation and/or chemotherapy would alter nitrogen balance, improve clinical outcome and accelerate general recovery.

The study population included patients already enrolled in the autologous and allogeneic bone marrow transplant protocols.

A. Materials and Methods

1. Patients

Patients were recruited from those already enrolled in autologous or allogenic bone marrow transplant treatment protocols. Under these protocols eligible patients are between the ages of 18 and 60 and of either sex, diagnosed with acute myelogenous leukemia (AML) in first remission (allogenic transplant), AML in second remission (autologous transplant), myelodysplasyic syndromes, lymphoma, aplastic anemia and other leukemias including chronic myelogenous leukemia (CML). The patients in this protocol required parenteral nutrition and had a dedicated central line for infusion. They had normal hepatic function (total bilirubin<3 mg/dl), normal renal function (creatinine<1.2 mg/dl), absence of diabetes (blood glucose<200 mg/dl without insulin or oral hypoglycemic agents). They were in the stable phase of their disease (e.g., in remission). Patients had not lost more than 20% of body weight below their ideal body weight.

2. Study Design study if allowed by their primary physicians. Daily oral calorie, protein, fat and carbohydrate intake was recorded.

Administration of the blinded test solution was initiated within five days after the day of bone marrow transplantation (referred to as day 0). After an initial equilibration period of 3 days, collection of all urine and stool began each 24-hours for the next seven days. No collections were performed the next seven days but resumed for the subsequent 7 days (i.e., approximately the third week post-transplant). Collections were from 4 p.m. to 4 p.m., corresponding to the time when the solution bags are hung and administered by the 9D nursing staff.

Blood was drawn weekly for GLN, glutamate, ammonia, amino acids, C-reactive protein and prealbumin. Other blood samples were obtained by the primary care physician for monitoring TPN and organ function The patients were randomized to treatment or control groups by unblinded research pharmacists. The groups were balanced for diagnosis and within the AML group in 1st remission, the groups were also balanced for treatment (with or without total body irradiation).

The study was terminated when the patient no longer required TPN as indicated by three consecutive days of ad libitum oral intake which averages 50% of calorie requirements. The third day of 50% oral intake is defined as the end of TPN. In all cases, the patients were included in the final outcome analysis only if they received at least 60% of required calories and protein of the blinded solution during the time period when TPN was required. The protocol calls for patients to be dropped from the study if 5 consecutive days pass during which he receives none of the blinded solution.

3. Nutritional Intake

Calorie intake was set at approximately 1.5 times estimated metabolic rate (based on height and weight. The nonprotein calorie intake was approximately 70% dextrose and 30% fat emulsion. The protein intake was 1.5 g/kg/day. Electrolytes and minerals were added in adequate amounts to maintain blood concentrations within the normal range. Vitamins were added as MVI-12 10 ml/24-hr. Trace element solution were added as Lypho-med 1 ml/24 hr. The TPN solution was administered on a 4 p.m. to 4 p.m. schedule by the ward nurses. In patients exceeding 20% of ideal body weight, the calorie and protein requirements were based on ideal weight for age and sex.

4. Medication

All medication and non-TPN fluids were given to these patients as deemed necessary by their physicians. All drugs and fluids which the patients received were recorded.

5. Additional Methods of Evaluation and End Points

Patients were evaluated for body composition (pre- and post-TPN), mid-arm muscle mass (pre and post treatment), hand grip strength (pre, days 7 and 21, and post-TPN),lactulose permeability (days 7 and 21, and post-TPN), sepsis severity score (weekly), graft vs. host disease, mcositis score (three times a week), general assessment of well-being (pre- and post-TPN).

The major end points evaluated included: (1) Nitrogen balance (week 1 and week 3); (2) Excretion of 3-methyl histidine and creatinine (mean of 3 urine values collected during days 5–7 of week 1 and week 3); (3) CRP (averaged over the first 4–6 weeks of TPN); (4) Body composition; (5) Mean weekly sepsis score; (6) Mean weekly fever and weekly mean of daily maximal temperature; and (7) Mean weekly GVH grade The minor end points evaluated include: (1) Days in unit (from time of transplant, T=0); (2) Days from transplant until recontamination; (3) Hospital charges, total antibiotic charges; (4) Antibiotic(s) ordered times the number of days administered, i.e., antibiotic days—only while on TPN and only counting those antibiotics added to the patient's treatment for known or suspected infection; (5) Days until leukocyte counts return to >500 and >1,000 cells/cm$^3$; (6) Days from transplant until absolute neutrophil count returns to >500 cells/cm$^3$; (7) Lactulose permeability, measured on two occasions at the end of two balance study periods; (8) Units of transfused platelets and red blood cells; (9) Days on TPN until 50% oral intake or discharge; and (10) Feeling of well-being.

B. Results

Figure 7:
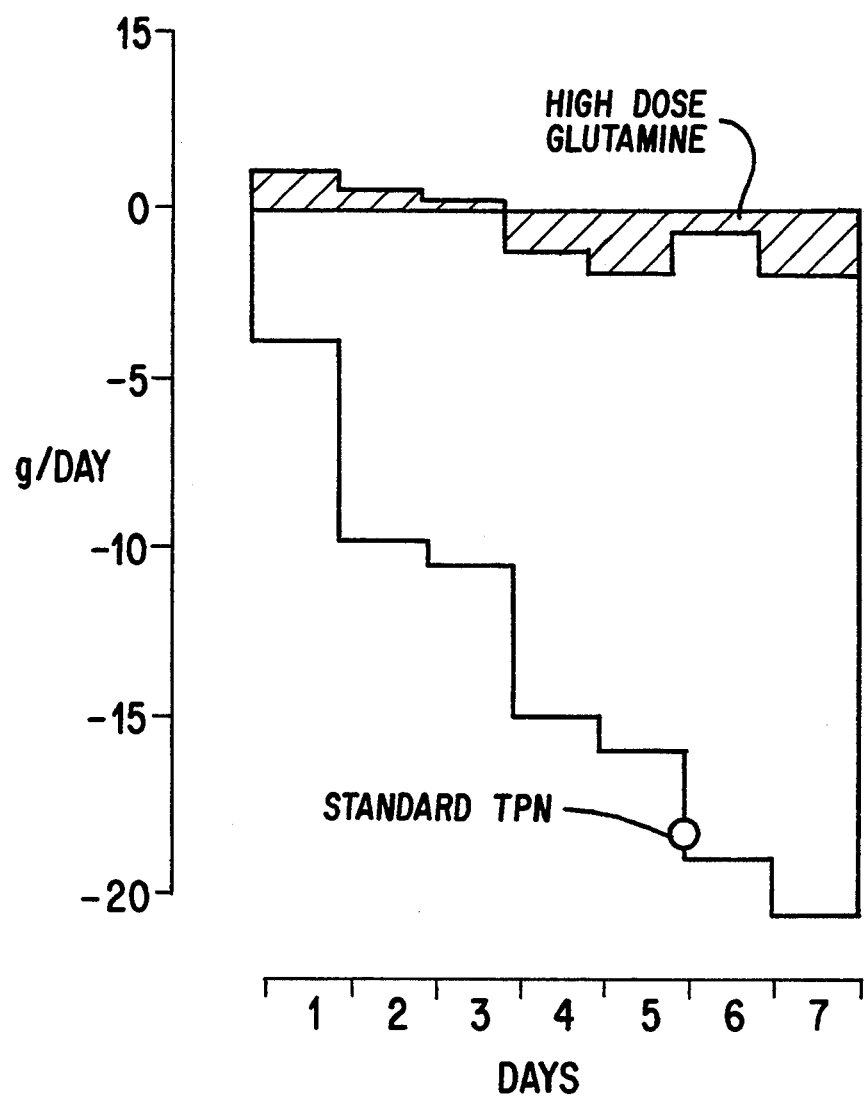
FIG. 7 is a graphic presentation of data demonstrating the effect of high dose GLN TPN on cumulative nitrogen balance after allogeneic bone marrow transplantation.

Results obtained with 2 patients are shown in FIG. 7 and Table XVI. TPN with high dose GLN induced a marked improvement in the clinical status of the transplant patients. This treatment prevented the increasingly negative nitrogen balance, decreased the severity of oral mucositis (largely induced by the chemotherapy), and improved the patients general health as assessed by the 3 clinical criteria shown. It is concluded that GLN has a palliative effect on the health of this class of severely ill patient.

TABLE XVI

Effect of Glutamine-supplemented TPN Following Bone Marrow Transplantation

|  | Standard TPN | High Dose GLN |
| --- | --- | --- |
| Nitrogen Balance (g/day) | −2.9 | +0.6 |
| Antibiotic Days[1] | 60 | 43 |

TABLE XVI-continued

Effect of Glutamine-supplemented TPN Following Bone Marrow Transplantation

|  | Standard TPN | High Dose GLN |
| --- | --- | --- |
| Days in Unit[2] | 46 | 39 |
| Days until Contamination[3] | 36 | 28 |
| Mucositis Score[4] | 2.5 | 1.0 |

[1]Product of the number of additional antibiotics added to the standard regimen and the number of days the patient is kept on the antibiotic
[2]Number of days patients are kept in Protective Environment (laminar air-flow rooms) until a clinical decision is made to release them (criteria include WBC > 1000, no fever, readiness to eat by mouth, etc.)
[3]Number of days patient is kept germ-free until physical contact with "contaminated" individual (usually a family member) is allowed. This is also a clinical decision.
[4]Clinical grading to oral mucositis on a scale of 0 to 4 of increasing severity)

Example 10

Effects of Glutamine-enriched Parenteral Nutrition on the Exocrine Pancreas

Total parenteral nutrition (TPN) is associated with intestinal and pancreatic atrophy and pancreatic exocrine insufficiency. Recent investigations have demonstrated that the addition of GLN to i.v. feedings attenuates TPN-associated intestinal atrophy. Furthermore, previous studies have shown that GLN, which is not present in standard amino acid formulas, is a preferred oxidative fuel for the pancreas and that a large proportion of exogenously administered GLN is consumed by pancreatic exocrine tissue. However, the effect of GLN supplemented i.v. feedings on the pancreas has not been reported. This study investigated the effects of an i.v. infusion of either a 2 gm/100 ml GLN-enriched diet (Glutamine) or an isonitrogenous, isocaloric, diet without GLN (Control) on the composition and structure of the exocrine pancreas in laboratory rats.

A. Materials and Methods

1. Animal Preparation

Male Wistar rats were maintained as described in Example 6–8. Only rats showing satisfactory weight gain while maintained on a diet of standard Purina ® rat chow were studied. In the first experiment (n=32) all animals underwent a 60% mid jejuno-ileal bowel resection and jugular vein catheterization whereas animals in the second experiment (n=24) underwent jugular venous catheterization and sham small bowel resection. Chow fed animals (n=18), were included to serve as a reference.

These operative procedure were performed as described in Example 6. Of the 69 rats entered into the study, no rats were excluded from the chow-fed groups, whereas 13 rats were excluded from the TPN groups because of catheter sepsis, anastomotic leak, intestinal obstruction, pump malfunction or catheter occlusion.

2. Study Protocol

After catheterization with or without small bowel resection, the animals were randomized to receive either standard rat chow (Chow) orally, a standard parenteral alimentation solution without GLN (Control) or a 2% GLN-enriched solution (Glutamine) by constant i.v. infusion for 7 days.

The i.v. diets provided all nutrients essential for growing rats (Popp et al., *Amer. J. Clin. Nutr.* 36:1119–1128 (1982)). The solutions were prepared and kept sterile. The parenteral diets were isocaloric (1.13 Kcal/ml), isonitrogenous (9.6 mg/ml) and differed from one another only in the composition of non-essential amino acids.

After recovery, rats were housed individually in metabolic cages and their infusion catheters attached to a swivel device (Instech labs, Inc.) that allowed for unrestricted movement during continuous infusion of nutrient solutions. In the first 16 hours following surgery, animals received 0.9% normal saline at 1 cc/hr and were allowed no oral intake. All animal were allowed free access to tap water from the first postoperative day until the end of the study. On the first postoperative day TPN-fed animals received 24 ml of the control or GLN-enriched diet to allow adaptation to the glucose infusion. Beginning on the second post-operative day, and continuing for the remainder of the study, adequate quantities (48 ml/day) of the parenteral diet were administered. Chow-fed animals, which always consumed all of the food given to them, were given a quantity of chow roughly equivalent in caloric density to the 24 hour caloric intake of TPN-fed rats. Thus, chow-fed animals were allowed 8 grams of Purina Rat Chow for the first 24 hours and 16 gm per day thereafter. The venous catheters of these animals were occluded on post operative day 2. Urine was collected daily in acidified wells beginning on the second post-operative day and aliquots were stored in acidified containers at $-20°$ C. Urine volume was recorded daily.

3. Tissue Preparation and Analytical Procedures

Animals were reweighed at the end of the study on the eighth post-operative day, anesthetized with pentobarbital (45 mg/kg i.p.), and blood was drawn from the heart into heparinized syringes. Whole blood GLN and glutamate concentrations were measured on these samples according to previously reported methods using reverse phase high performance liquid chromatography (Smith, R. J. et al., *J. Liq. Chromatography* 8:1783–1795 (1985)).

Following exsanguination a small piece of pancreas (3×3 mm) was immediately excised from the mid portion of the gland at the junction of the splenic and gastric segments, fixed in buffered 2.5% glutaraldehyde solution and stored at 4° C. until processed for histology. The remainder of the pancreas was carefully dissected and separated from adjacent mesenteric fat and lymphatic tissues. The pancreatic resections were performed in a blinded fashion. Pancreata were weighed, diluted (1:10, wt/vol) in ice cold distilled water and homogenized for 30 seconds with a Polytron tissue homogenizer. The homogenate was sonicated for 30 seconds and stored at $-70°$ C. until analyzed for DNA, protein, and enzyme contents. The livers excised, weighed, dried at 90° C. for 72 hr and the dry weight determined.

4. Biochemical Assays

Aliquots of urine from each day were pooled to estimate cumulative daily nitrogen balance. The nitrogen content of the acidified urine samples were determined using a macroKjeldahl technique. The protein content of pancreatic homogenates was measured by the method of Lowry (Lowry, Ohio et al., *J. Biol. Chem.* 193:265–275 (1951)) and DNA using a modification of the method of Burton (Burton, K. A., *Biochem. J.* 62:315–322 (1965)). A portion of each pancreatic homogenate was diluted to a protein concentration of 200 mgm/ml with buffer containing 0.01% bovine serum albumin and stored at $-20°$ C. prior to determination of enzyme activities. Amylase activities in diluted samples were determined using a modification of the method of Bernfeld (Bernfeld, P., Amylases: alpha and beta, In: Colowick SP, eds. Kaplan NO, *Methods of Enzymology*, Vol. I. Academic Press, NY, 149–158 (1955)), and trypsin activities were determined by the method of Hummel (Hummel B.C., *Can J. Biochem. Physiol.* 37(12):1393–1399 (1959)). Activation of trypsinogen was produced by incubation of 400 ml of sample with 0.0492 mg of procine enterokinase at 37° C. for 4 hours. Lipase activities were measured on a Kodak Ektachem 700 Analyzer using the 2 point rate method of Mauck (Mauck, J. C. et al., *Clin.* (1984)). Enzyme activities are expressed in units (U) of micromoles of product generated per minute (1 KU=$10^3$ units).

5. Pancreatic Histology

Pancreatic tissue was fixed at 4° C. in 2.5% glutaraldehyde phosphate buffer and post-fixed in 1% osmium tetroxide for 2 hours at room temperature. The tissue specimens were then dehydrated in ascending grades of alcohol and embedded in Araldite. One micron thick sections were stained with 1.0% toludene blue for light microscopy. A LKB Nova ultra microtone was used to prepare 600–800 A thick sections for electron microscopy. These sections were stained with uranyl acetate and lead citrate, and then examined in a Phillips 301-transmission electron microscope. Acinar cells were photographed by electron microscopy and then enlarged to working prints at a final magnification of 2793× and 7127×.

6. Data Analysis

Results are expressed as the mean ± standard error of the mean (s.e.m.). Pancreatic wet weight, DNA, and protein content are expressed per total pancreas and per 100 g of body weight. Pancreatic weight and protein content were also calculated per mg of DNA as an index of cell size. Ideally, for these indices, comparisons between groups are made after correction for body weight since a linear relationship exists between total body-weight and total pancreas wet weight in male Wistar rats between 100 and 300 grams in size. Pancreatic enzyme activities (Units/mg protein) are expressed as total gland content and as specific activity (Units/mg pancreatic DNA). Mean profile diameters of zymogen granules were calculated according to the method of Weibel (Weibel, E. R. et al., *Principles and Techniques of Electron Microscopy: Biological Applications*, Vol. 3, ed. M. A. Hayat, Van Nostrand Reinhold, N.Y. (1973)).

Two way analysis of variance was used to assess the effects of GLN and intestinal resection (Winer, B. J., *Statistical Principles in Experimental Design* (2nd ed.), McGrawHill, N.Y. (1971)). If the analysis of variance indicated a significant main effect, unpaired t-tests were used for the planned post-hoc comparisons between animals given the GLN-enriched diet and their appropriate controls. Data from chow fed animals are included to demonstrate the degree of pancreatic atrophy in the treatment groups, but were not included in the analyses of overall treatment effects. Differences were considered statistically significant when probability (p) values were less than 0.05.

B. Results

1. Body Weight, Nitrogen Balance and Plasma Glutamine and Glutamate.

Changes in body weight and nitrogen balance were similar in GLN-fed and control animals with or without small bowel resection (Table XVII. In the animals that underwent small bowel resection, plasma GLN (1143±75 vs. 890±41, GLN vs. Control, p<0.05) and plasma glutamate concentrations (177±12 vs. 144±8, GLN vs. Control, p<0.05) were significantly higher in the GLN group as compared to the Control group. No other significant differences were observed between GLN-fed and control animals.

2. Pancreatic Indices

TPN-fed animals had significantly smaller mean pancreatic wet weight (33–43%), less protein (25–58%) and DNA (14–30%) compared to chow fed animals (Table XVIII).

In the non-resected animals, GLN infusion was associated with increased pancreatic weight (22%), DNA (32%) and protein (24%) per 100 gram body weight as compared to controls. These differences were significant for pancreatic weight (p<0.05) and DNA (p<0.005) respectively but not for pancreatic protein (p=0.06). In these animals pancreatic protein/DNA and pancreatic weight/DNA ratios were not significantly different (Table XVIII.)

The pancreata of animals who underwent 60% small bowel resection and were fed GLN were significantly heavier (14%, p<0.05), and had greater total pancreatic protein per 100 gm body weight (31%, p<0.05) as compared to controls. Total DNA content, pancreatic weight/DNA and protein/DNA ratios were not significantly different, though the latter was 20% larger in the GLN group.

3. Pancreatic Enzymes

TPN-fed animals had decreased total pancreatic enzyme activity as compared to chow-fed animals (Table XIX). In resected animals, total pancreatic trypsinogen (p<0.005) and trypsinogen specific activity (p<0.005) were significantly greater in the GLN group as compared to the Control group. There were no other differences in enzyme content or specific activity between the GLN-fed and control animals.

4. Pancreatic Histology and Ultrastructure

Exocrine pancreatic tissue and the islets of Langerhans appeared normal in all animals under light microscopy; there was no evidence of pancreatitis or edema to account for increased weight or protein contents seen in rats fed the GLN-enriched diet. The mean profile diameter of zymogen granules for non-resected TPN-fed animals and was significantly smaller than that in rats fed chow (3.88±0.06 for GLN, 3.80±0.05 for Controls, and 4.69±0.10 for Controls, p<0.05 by 1-way ANOVA); The Glutamine and Control groups were not significantly different. When similarly oriented acinar unit profiles were compared, an increase in cell volume density, number or zymogen granules, and percent area of the cell volume occupied by zymogen granules were apparent in GLN-fed animals compared to controls.

5. Analysis of Treatment Effects from Combined Series

Animals fed the GLN-enriched diet or that underwent small bowel resection had significantly elevated plasma GLN (p<0.02) and glutamate (p<0.02) concentrations. GLN infusion did not affect cumulative nitrogen balance whereas intestinal resection had a significant negative effect. Pancreatic weight (p<0.0001), protein (p<0.002), and DNA (p<0.004) contents were significantly higher in animals given GLN and these effects were independent of intestinal resection. Intestinal resection significantly decreased mean total pancreatic protein content (p<0.006) and the pancreatic protein/DNA ratio (p<0.05).

Animals fed GLN had significantly greater pancreatic trypsinogen (p<0.02) and lipase content (p<0.03). The total amylase content and all enzyme specific activities were not affected by GLN infusion. Intestinal resection had a profound negative effect (p<0.0001) on the total content and specific activities of trypsinogen, amylase, and lipase.

In conclusion, GLN-supplemented TPN significantly attenuated the loss in pancreatic weight (14–22%), DNA (12–32%) and protein (24–31%) that occurred in animals receiving the Control diet. Overall, GLN fed animals had significantly increased total pancreatic trypsinogen (53%) and lipase (30%) contents, but no difference in enzyme specific activities, as compared to controls. GLN is therefore an important nutrient for pancreatic exocrine tissue during TPN. The trophic effect of GLN on the pancreas during i.v. feeding has important clinical implications.

TABLE XVII

| Body Weight, Nitrogen Balance, Plasma Glutamine and Glutamate in TPN and Chow-fed Rats | | | | | | |
|---|---|---|---|---|---|---|
| | Non-Restricted | | | Restricted | | |
| | Control | Glutamine | Chow | Control | Glutamine | Chow |
| No. of Animals | 7 | 7 | 10 | 12 | 12 | 8 |
| Body Weight (gm) | | | | | | |
| Day 0 | 197 ± 4 | 193 ± 4 | 187 ± 2 | 208 ± 3 | 209 ± 3 | 197 ± 5 |
| Day 8 | 179 ± 3 | 180 ± 5 | 197 ± 2 | 193 ± 3 | 193 ± 4 | 199 ± 5 |
| Cumulative Nitrogen Balance (gm) | 2.3 ± 0.0 | 2.3 ± 0.0 | 3.3 ± 0.0 | 1.1 ± 0.0 | 1.1 ± 0.0 | 3.3 ± 0.0 |
| Plasma Glutamine ($\mu$mol/L) | 823 ± 68 | 896 ± 63 | 644 ± 26 | 890 ± 41 | 1143 ± 75* | 545 ± 57 |
| Plasma Glutamate ($\mu$mol/L) | 108 ± 5 | 123 ± 5 | 80 ± 6 | 144 ± 8 | 177 ± 12 | 79 ± 2 | data are expressed as mean ± s.e.m.
*p < 0.05 compared to the respective control group by unpaired t-test after 2-way ANOVA

TABLE XVIII

| Pancreatic Indices and Liver Wet Weight in PTN and Chow-fed Animals | | | | | | |
|---|---|---|---|---|---|---|
| | Non-Restricted | | | Restricted | | |
| | Control | Glutamine | Chow | Control | Glutamine | Chow |
| No. of Animals | 7 | 7 | 10 | 12 | 12 | 8 |
| Pancreatic DNA Total (mg) | 2.8 ± 0.2 | 3.6 ± 0.2*** | 4.2 ± 0.3 | 3.0 ± 0.1 | 3.4 ± 0.3 | 4.3 ± 0.3 |
| Pancreatic Wet Weight | | | | | | |
| Total (mg) | 555 ± 26 | 680 ± 39* | 999 ± 52 | 602 ± 19 | 704 ± 25*** | 1080 ± 63 |

TABLE XVIII-continued

Pancreatic Indices and Liver Wet Weight in PTN and Chow-fed Animals

| | Non-Restricted | | | Restricted | | |
|---|---|---|---|---|---|---|
| | Control | Glutamine | Chow | Control | Glutamine | Chow |
| mg/100 μg DNA Pancreatic Protein | 20 ± 1 | 19 ± 1 | 24 ± 1 | 20 ± 1 | 22 ± 1 | 25 ± 1 |
| Total (mg) | 82 ± 8 | 102 ± 6 | 147 ± 6 | 68 ± 4 | 90 ± 6*** | 186 ± 13 |
| mg/mg DMA | 30 ± 2 | 28 ± 1 | 35 ± 1 | 23 ± 2 | 28 ± 2 | 43 ± 2 |
| Liver Wet Weight (gm) | 8.16 ± 0.16 | 8.40 ± 0.28 | 9.2 ± 0.34 | 9.90 ± 0.24 | 10.1 ± 0.50 | 8.8 ± 0.80 | data are expressed as mean ± s.e.m.
*p < 0.05 compared to the respective control group by unpaired t-test after 2-way ANOVA

TABLE XIX

Pancreatic Enzyme Activities

| | Non-Restricted | | | Restricted | | |
|---|---|---|---|---|---|---|
| | Control | Glutamine | Chow | Control | Glutamine | Chow |
| No. of Animals | 7 | 7 | 10 | 9 | 11 | 3 |
| Amylase | | | | | | |
| KU/total Pancreas | 15.0 ± 2.0 | 14.5 ± 0.5 | 16.7 ± 1.5 | 0.35 ± 0.26 | 1.18 ± 0.66 | 18.9 ± 4.6 |
| KU/mg DNA | 5.7 ± 0.8 | 4.0 ± 0.2 | 4.2 ± 0.4 | 0.14 ± 0.11 | 0.39 ± 0.22 | 4.4 ± 0.5 |
| Trypsinogen | | | | | | |
| U/Pancreas | 374 ± 74 | 496 ± 96 | 611 ± 75 | 139 ± 23 | 283 ± 22*** | — |
| U/mg DNA | 137 ± 20 | 132 ± 20 | 140 ± 9 | 50 ± 9 | 87 ± 6*** | — |
| Lipase | | | | | | |
| KU/Pancreas | 10.7 ± 1.4 | 14.9 ± 2.4 | 27.4 ± 2.6 | 7.5 ± 1.1 | 9.6 ± 0.7 | 25.7 ± 2.8 |
| KU/mg DNA | 19.4 ± 2.4 | 22.8 ± 4.5 | 30.9 ± 2.7 | 12.6 ± 1.6 | 13.7 ± 0.9 | 26.8 ± 2.6 | data are expressed as mean ± s.e.m
KU = $10^3$ units; 1 unit = 1 μmole substrate formed per minute
***p < 0.005 by unpaired t-test after 2-way ANOVA

Example 11

Glutamine Prevents Pancreatic Atrophy During Feeding of an Elemental Enteral Diet In vitro studies demonstrate that GLN is an important respiratory fuel for the pancreas but the role of GLN-supplemented enteral diets on the structure and function of the pancreas is unknown. The effects of standard and GLN-supplemented elemental diets on pancreatic and intestinal growth following operative stress were examined in male Wistar rats (n=25, wt 195–210 g). Following a 60% midjejuno-ileal intestinal resection and gastrostomy, rats were randomized to receive chow or a continuous infusion of a standard elemental diet (CON) or an isonitrogenous, isocaloric, 2 gm/100 ml GLN-supplemented diet (GLN). The elemental diets differed only in their source of nonessential nitrogen. Urine was collected daily and nitrogen balances determined over the study period. At sacrifice, body weight was determined and blood obtained for GLN, glutamate (GLU), and ammonia. Liver, intestine and pancreas were excised, weighed, assayed for DNA and protein content and prepared for histology. Liver and pancreas were also assayed for fat and enzyme contents. A portion of the data are shown as means ±sem in Table XX, below.

creatic protein content and prevented the gain in liver wet weight compared to the CON group. When data from the GLN and CON groups were pooled, pancreatic weight and DNA were related to plasma GLU (p<0.03) but not to GLN levels. Because body weight and nitrogen balance were similar between GLN and CON groups, the effects of GLN appear to be specific for the maintenance of pancreatic mass during the postoperative period. These findings further support the hypothesis that GLN is a conditionally essential nutrient for gastrointestinal tissues following surgical stress.

Example 12

Glutamine-enriched Parenteral Nutrition Suppresses Damage to Gut Wall Induced by 5-Fluorouracil Lactulose is a non-metabolizable sugar that is poorly absorbed from the gastrointestinal tract. In gastrointestinal disorders such as inflammatory bowel disease, lactulose is taken up through gaps in the mucosal membrane, allowing its excretion in the urine. The amount of urinary lactulose is therefore a measure of "leakage" across the gut mucosal barrier (Menzies, Biochem. Soc. Trans. 550: 1042–1047 (1974)).

Rats were treated with 5-fluorouracil as described in Example 8, above. Lactulose, 2 ml iso-osmolar solution of 100 mg/ml, was infused by gavage and urine was

TABLE XX

| | | Pancreas (mg/100 gm/Body wt.) | | | Liver | Plasma (μmoles/L) | |
|---|---|---|---|---|---|---|---|
| Treat | n | Wt. | DNA | Protein | Wt (gm) | GLN | GLU |
| Con | 8 | 343 ± 19 | 2.7 ± 0.2 | 68 ± 5 | 10.4 ± 0.4 | 976 ± 60 | 165 ± 12 |
| GLN | 9 | 439 ± 15* | 3.3 ± 0.3 | 95 ± 9* | 8.7 ± 0.4* | 1148 ± 104 | 109 ± 14 |
| Chow | 8 | 547 ± 38# | 2.2 ± 0.2 | 94 ± 7* | 8.8 ± 0.8* | 718 ± 61# | 101 ± 5# |

*p <0.05 vs CON; #: p <0.005 Chow vs CON or GLN (ANOVA)

Feeding the elemental diets decreased pancreatic weight relative to chow fed animals. GLN significantly attenuated the loss in pancreatic weight, increased pancollected over the subsequent 24 hr and frozen. Urinary lactulose was determined enzymatically as described by Ziegler et al. (*Arch. Surg.* 123: 1313–1319 (1988)).

Treatment with a single injection 5-FU was found to increase gut permeability to lactulose by 24 hr. This increase peaked at between 24 and 48 hrs. after chemotherapy. Over a three day period, animals receiving GLN-enriched TPN, had significantly reduced gut permeability compared to animals fed standard TPN. For example, at 48–72 hr. after 5-FU, 24 hr. lactulose excretion was reduced from 32 to 17 $\mu$moles in the GLN-treated rats.

It is concluded that GLN protects the gut wall from the increase in permeability that accompanies chemotherapeutic drugs. This effect is expected to be of major importance in preventing infection via the GI route, and likely contributes to the more rapid recovery of patients undergoing bone marrow transplantation, as described in Example 9, above.

Example 13

Glutamine Alleviates Immunosuppressive Effects of TPN

Rats were fed with either laboratory chow, TPN, or GLN-supplemented TPN as described in Example 10 (Materials and Methods, Sec. 2). Seven days after initiation of treatment, animals were sacrificed and the spleen, thymus, and mesenteric lymph nodes were harvested. Cell suspensions were prepared from these organs using standard techniques (see Klein, *Immunology: The Science of Self-Nonself Discrimination,* Wiley-Interscience, 1982). Lymphocyte proliferative responses in vitro in the presence of mitogens were carried out using methods well known in the art. Compared to the chow group, TPN for 1 week markedly reduced lymphocyte responsiveness by as much as 50%. This suppression was reversed by the presence of GLN in the parenteral solution, such that the GLN treated rats showed lymphocyte responses intermediate between those of the TPN animals and the control chow-fed rats.

The presence of GLN in the parenteral solution therefore significantly alleviates the immunosuppressed state produced by TPN in the absence of GLN. The breakdown of the gut mucosal barrier, as described in Example 12 above, combines with the compromised immune function to increase the susceptibility to infection of the animal maintained on TPN. Enhanced susceptibility is likely not only to bacteria and other microorganisms entering via the gut, but by any other route as well (due to the compromised immune function). GLN-supplemented TPN is capable then of promoting host defense by several independent mechanisms. The improved infectious status of the patients undergoing bone marrow transplantation (see Example 9, above) serves as corroborative evidence for such "pro-host" activity of GLN.

Having now fully described this invention, it will be appreciated by those skilled in the art that the same can be performed within a wide range of equivalent parameters, concentrations, and conditions without departing from the spirit and scope of the invention and without undue experimentation.

In this example, a double-blind, prospective, controlled trial in bone marrow transplant recipients determined whether glutamine supplementation improves nitrogen retention and reduces hospital morbidity compared to standard, glutamine-free parenteral feeding.

Patients and Methods

The patients were recruited from individuals treated with allogeneic bone marrow transplantation at the Brigham and Women's Hospital, Boston, Mass. Eligible study patients were randomized into control or experimental groups balanced for diagnosis, antineoplastic treatment, graft-versus-host disease prophylaxis regimen and sex. All individuals other than the research pharmacists were blinded to the randomization. The patients had no evidence of non-neoplastic systemic disease and were deemed to require intravenous nutritional support following transplantation. Patients were hospitalized one week before transplantation and placed in laminar airflow rooms. All patients received central venous catheters and underwent intestinal decontamination with daily administration of oral vancomycin, gentamicin and nystatin. A daily mouth and skin care regimen of 0.12% chlorohexidine gluconate was administered to inhibit microbial colonization. All received intravenous acyclovir for herpesvirus prophylaxis. The pre-transplant conditioning regimen consisted of high-dose chemotherapy and total body irradiation (1300 cGy; 26), or chemotherapy alone as noted below. Graft-versus-host disease prophylaxis consisted of ex-vivo T-lymphocyte depletion with ST-1 immunotoxin or intravenous methotrexate and cyclosporin (Antin et al. *Prog Clin Biol Res* 333: 207–15 (1990)).

The bone marrow was transfused following the conditioning regimen (day 0). Parenteral nutrition containing adequate micronutrients, was initiated the following day (day 1). Ad libitum food intake of a standardized diet providing only foods of low bacterial content was allowed. The meals were routinely tested for bacterial content, and foods such as fresh fruits or fish were prohibited. Food was prepared from standardized portions under a laminar air-flow hood in the transplant unit kitchen. The calories provided by parenteral nutrition were based on basal energy requirements (Wilmore D. W., The Metabolic Management of the Critically Ill, 2nd edition. New York: Plenum Medical Book Company, 1980) multiplied by 1.5 to provide estimated maintenance energy needs (Szeluga et al. *JPEN J Parenter Enteral Nutr* 9: 139–43 (1985)). Seventy percent (70%) of nonprotein calories given as dextrose and 30% as lipid emulsion (Intralipid, Kabi Vitrum, Stockholm, Sweden). Parenteral protein intake was provided as crystalline amino acids administered at a dose of 1.5 g protein/kg/day. The intravenous diets for each group were thus isocaloric and isonitrogenous and differed only in amino acid content.

Based on a pilot Phase I study (Ziegler et al. *JPEN J Parenter Enteral Nutr.* 14(suppl):137S–46S (1990)), patients received either a commercially available amino acid solution or an amino acid solution containing 0.57 g glutamine/kg/day. The primary strategy of the study was to compare the experimental diet to the standard of nutritional care in this transplant unit; thus, the control diet contained the glutamine-free amino acid formulation routinely utilized (Ziegler et al. *JPEN J Parenter Enteral Nutr.* 14(suppl):137S–46S (1990)). The experimental amino acid solution was formulated as previously described by combining a commercially available formulation with free L-glutamine (Ziegler et al. *JPEN J Parenter Enteral Nutr.* 14(suppl):137S–46S (1990)). Compared to the control formula, this solution had a lower amount of total essential amino acids as a percent of total amino acids (33% vs 45%) and lower amounts of most non essential amino acids. However, the major difference between the two formulas was the presence or absence of glutamine (Table 22). Other than clinically indicated electrolyte alterations, the content of the nutrient solution was fixed throughout the study. Parenteral nutrition was discontinued when the patient consumed at least 50% of nutritional requirements enterally for three consecutive days.

Patients were followed by the investigators daily until hospital discharge. All significant clinical events, including all administered drugs and blood products were recorded. The incidence and grade of acute graft-versus-host-disease were recorded five times weekly (Glucksberg et al. *Transplantation.* 18: 295-304 (1974)). The oral mucosa was examined for presence and severity of mucositis three times weekly and graded as a function of the degree of inflammation.

Intravenous antimicrobial agents were prescribed by the primary physicians. Biweekly surveillance cultures of the throat, stool and blood were obtained throughout hospitalization and other cultures were obtained as clinically indicated. All microbial culture results were tabulated from Day 0 until the initiation of gut/skin recontamination by the primary physicians. Recontamination included discontinuation of oral antibiotics and the oral administration of lactobacilli.

Clinical infection was defined as the presence of positive blood cultures or by signs and symptoms compatible with localized infection (with or without positive microbial cultures of the affected site) which prompted initiation or alteration of antibiotic administration and adjunctive care. The number of days of therapeutic antibiotic use after transplantation was calculated. The total number of antibiotic days was calculated by daily tabulation of all intravenous antimicrobial agents begun after day 0 (e.g. three antibiotics given in one day would be scored as 3).

All 24-hour intakes of enteral and parenteral calories, protein and fluid were determined using standard techniques as previously described (Wilmore D. W., The Metabolic Management of the Critically Ill, 2nd edition. New York: Plenum Medical Book Company, 1980; Ziegler et al. *JPEN J Parenter Enteral Nutr.* 14(suppl):137S-46S (1990)). Nitrogen balance was determined in the initial 24 patients after an initial 3-day equilibration period. All urine, stool and vomitus were collected in 24-hour pools between days 4 and 11, and nitrogen balance calculated (Ziegler et al. *JPEN J Parenter Enteral Nutr.* 14(suppl):137S-46S (1990)). Nitrogen intake potentially derived from infused blood products, and losses via blood draws (~50-75 ml/day), were not included in this calculation. Transfusions of blood (3 units of packed cells/patient) and platelets (4 units/patient) were similar during the balance period in each group. The balance data included corrections for daily creatinine excretion and changes in blood urea nitrogen (Wilmore, D. W., The Metabolic Management of the Critically Ill, 2nd edition. New York: Plenum Medical Book Company, 1980). Nitrogen losses from skin, hair and breath were assumed to be similar between groups and not included in the balance calculation. The urinary excretion of 3-methylhistidine was measured on days 9 to 11 and the urinary 3-methylhistidine/creatinine ratio calculated (28). A priori criteria allowed exclusion of nitrogen balance data from one patient requiring methylprednisolone for acute graft-versus-host disease during the balance period; thus balance data on 23 patients were analyzed.

All clinical laboratory determinations were recorded. Additional blood samples were obtained weekly in the initial 24 patients and analyzed for plasma amino acids, ammonia, and C-reactive protein. All biochemical analyses were performed using standard methods (Ziegler et al. *JPEN J Parenter Enteral Nutr.* 14(suppl):137S-46S (1990); Mondzac et al. *J Lab Clin Med* 66: 526-31 (1965); Smith et al. *J Liq Chromatog* 8: 1783-95 (1985); Wassner et al. *Anal Biochem* 104: 284-89 (1980)). Total days on parenteral nutrition, days until marrow engraftment (average neutrophil count greater than $0.5 \times 10^9/L$), days until initiation of recontamination, total blood and platelet transfusions, and total days in the hospital following transplantation were tabulated.

All data were tested for statistical outliers, as defined by those data falling outside of one and one-half times the interquartile distance from the median value determined by combining data from the two groups. Four such values were excluded. Nitrogen balance data in a control patient were markedly negative and were excluded from the analysis of nitrogen balance over time. This exclusion had no effect on the significance of the data. Three patients were hospitalized for a prolonged period of time because they were clinically dissimilar from the rest of the study group. Two glutamine-treated patients were kept in the hospital after engraftment due to hepatitis and uncontrolled hypertension; only their length of stay data (73 and 60 days respectively) were excluded. A control patient who rejected the first marrow transplant and received a second transplant (length of stay 95 days) was excluded from all data analysis. Paired and unpaired t-tests were utilized for comparisons of normally distributed data; the Mann-Whitney, chi-square and Fisher's tests were utilized as appropriate for nonparametric comparisons. Data from controls and glutamine-treated subjects assessed over time were compared using a repeated measures analysis of variance. Effects of parenteral nutrition on clinical laboratory data were determined during the first 21 days when all patients received parenteral nutrition. P values less than 0.05 were considered significant.

Results

The control and experimental groups were clinically comparable at entry. (Table 21). Human immunoglobulin was administered to a similar number of patients (62% of controls compared to 71% glutamine-treated, $P > 0.3$). Eight patients in each group were positive for cytomegalovirus antigen. Cytosine arabinoside, cyclophosphamide and total body irradiation were administered as conditioning therapy to 40 patients; three received cyclophosphamide and busulfan alone and two received cyclophosphamide, etoposide and carmustine alone. ST-1 immunotoxin was administered to 67% of control and 71% of glutamine-supplemented patients.

The length of time patients required parenteral nutrition and the mean daily intravenous, oral and total energy and nitrogen intakes were similar in both groups (Table 23). Both groups demonstrated similar maximal and mean daily temperature, cumulative mucositis scores, antibiotic usage, acute graftversus-host disease incidence and severity, use of corticosteroids, transfusion requirements, days until neutrophil engraftment and days until recontamination (Table 24)

Figure 8A:
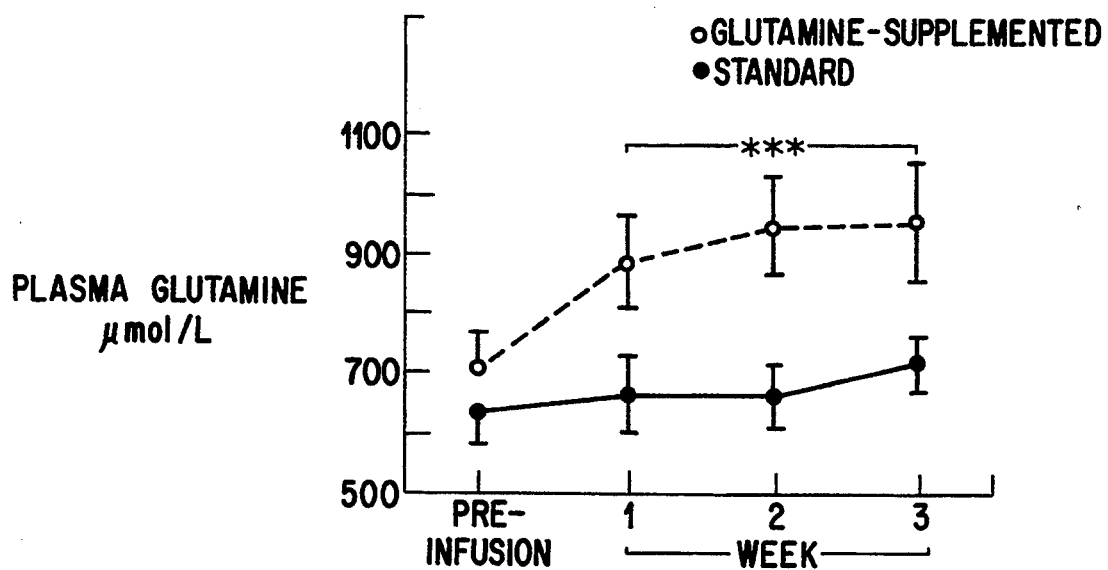
FIG. 8: Plasma glutamine, glutamate, and ammonia concentrations over time in the initial 24 patients. Glutamine levels rose with glutamine-supplemented nutrition ($p < 0.001$) and glutamate concentrations were similar between groups. Ammonia levels were significantly higher in the glutamine-supplemented patients prior to initiation of intravenous feeding. Levels rose gradually over time in each group but were unrelated to treatment.
Figure 8B:
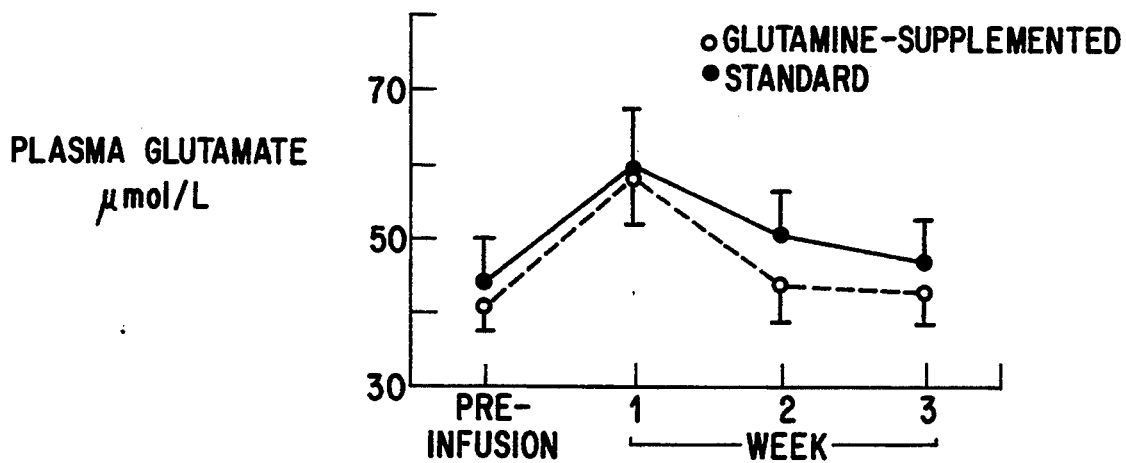
Figure 8C:
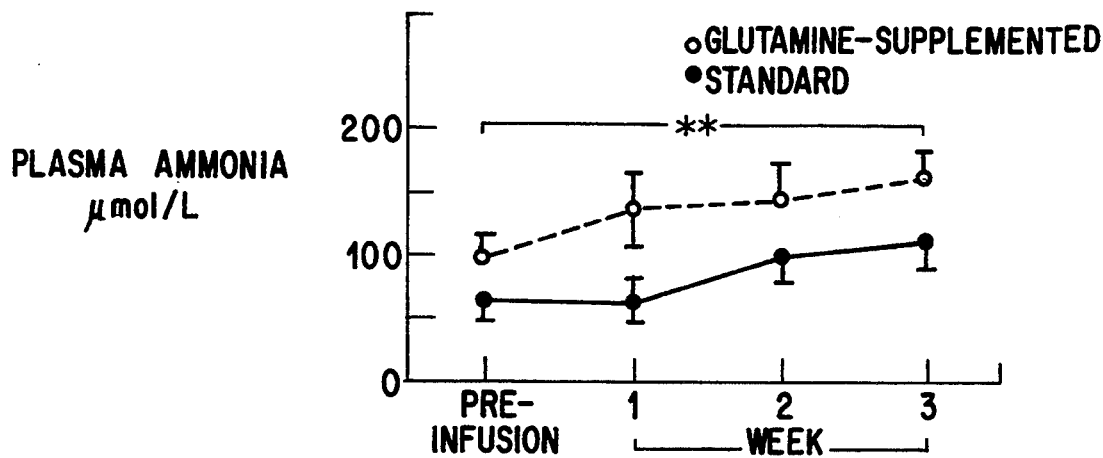

All subjects completed the trial without clinically significant deleterious effects attributable to the parenteral nutrition solutions. Plasma glutamine concentrations rose significantly (40%) in the experimental group during the first week of parenteral feeding. Alterations in glutamate and ammonia concentrations were unrelated to glutamine administration (FIG. 8) Other amino acid concentrations (not shown) reflected the composition of the solution infused. When blood chemistries and complete blood counts were evaluated, a significant treatment effect of glutamine over time was observed only for total bilirubin, which averaged $14\pm2$ μmol/L in the controls compared to $18\pm3$ μmol/L in the experimental patients (P=0.044). Leukocyte counts averaged $0.962\pm0.184\times10^9$/L in the controls compared to $0.786\pm0.095\times10^9$/L in the glutamine-supplemented patients between days 1 and 21 (not significant). The days until total leukocyte counts exceeded $0.5\times10^9$/L and $1.0\times10^9$/L were also similar for both groups ($16\pm1$ compared to $16\pm1$ and $18\pm1$ compared to $18\pm1$).

The glutamine-supplemented patients had a significantly lower incidence of positive microbial cultures and clinical infection (Table 24). For example, only one of the control patients (5%) had negative microbial culture results from the day of transplantation until the initiation of recontamination. In contrast, all cultures remained negative in 10 glutamine-supplemented patients (42%) during this time (P equal 0.005).

Overall, the majority of positive cultures (57%) were Candida albicans; 30% were coagulase-negative staphylococcus and 14% were of other organisms. Clinical infections (n equal 10) developed in 43% of the control patients (coagulase-negative Staphylococcal bacteremia 4; *Staphylococcus epidermitis* and Aspergillus species cellulitis 2; clinically evident pneumonia 3; coagulase-negative Staphylococcal catheter entrance site abscess 1). In contrast, only 12% of glutamine-treated patients (N equal 3) developed foci of infection (*Escherichia coli* urinary tract infection 2; coagulase-negative Staphylococcal bacteremia 1; P equal 0.041). Two control patients (10%) completed the hospital course without the addition of systemic antibiotics compared to five patients (21%) receiving glutamine.

Figure 9B:
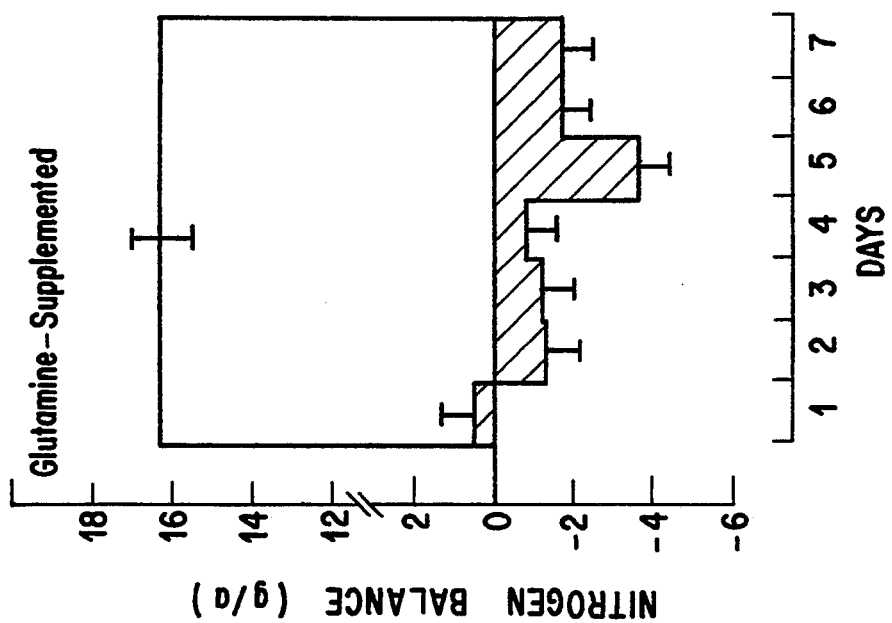
FIG. 9: Nitrogen balance in the two groups of patients receiving isocaloric, isonitrogenous parenteral feedings between days 4–11 posttransplant. Nitrogen intake (mean±S.E.M.) for the week is shown by the uppermost horizontal line and balance for each 24-hour period (mean±S.E.M.) is represented by the shaded areas. The group receiving the standard diet (N=11) received no glutamine, while the group receiving glutamine supplementation (N=12) received 0.57 g glutamine/kg/day. Daily nitrogen balance was significantly different between the two groups by analysis of variance (P=0.001). To convert grams to mmol, multiply by 71.4.
Figure 9A:
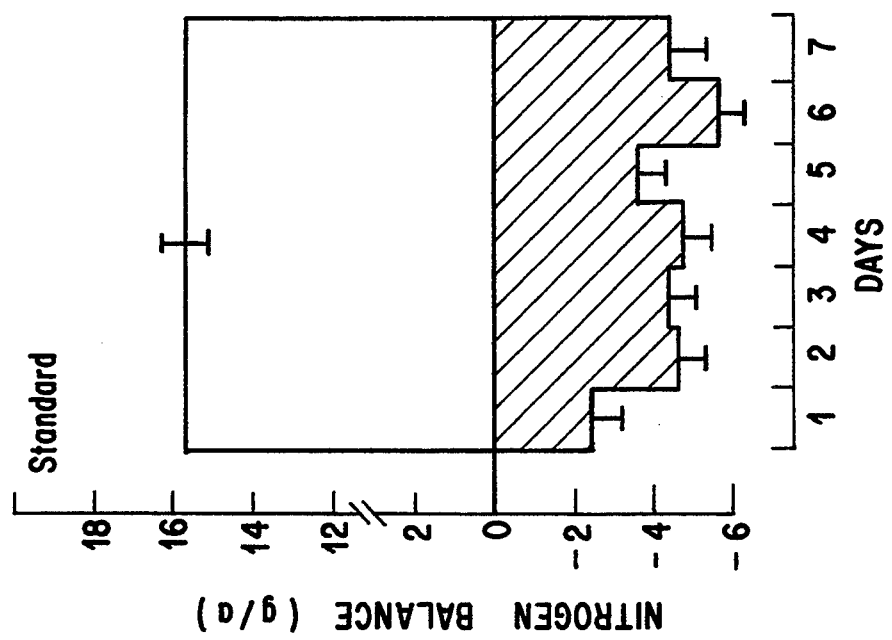

Nitrogen balance was markedly negative in the eleven control patients studied ($-4.2\pm1.2$ g/day); however, significantly improved nitrogen retention occurred in the patients receiving glutamine-supplemented parenteral nutrition (Table 23, FIG. 9). Cumulative nitrogen balance was significantly greater and the 3-methylhistidine/creatinine excretion ratio, (an index of myofibrillar protein breakdown), was significantly less in the experimental group (Table 23). The difference in nitrogen metabolism was not explained by indicators of infection/inflammation during the balance study which were similar between groups (mean daily temperature $37.6°\pm0.3°$ C. control compared to $37.4\pm0.2$ experimental; mean daily peak temperature $38.2°\pm0.2°$ C. compared to $38.0\pm0.2$; C-reactive protein concentration $62.7\pm13.4$ μg/L compared to $45.5\pm10.3$; infectious foci 18% of control patients compared to 8% of glutamine-supplemented).

All patients survived the transplantation protocol and were discharged from the hospital. The overall 100-day survival rate was similar between groups (control 86% vs. glutamine-supplemented 83%). However, hospital stay was significantly reduced in the experimental patients. Patients receiving standard parenteral nutrition were discharged $36\pm2$ days following transplantation; in contrast, patients receiving glutamine supplementation were discharged after $29\pm1$ days (p=0.017).

Discussion

In this prospective, randomized, double-blind trial, patients receiving the glutamine-enriched parenteral nutrition formula demonstrated significantly improved nitrogen retention, fewer infectious foci, significantly lower rates of microbial colonization and a reduced length of initial hospital stay versus results with standard, glutamine-free intravenous feedings. This study is the first demonstration in humans that glutamine-supplemented feeding improves clinical outcome and the first demonstration of reduced hospital morbidity in bone marrow transplant patients associated with a specific nutritional therapy (Weisdorf et al. *J Pediatr Gastroenterol Nutr* 3:95–100 (1984); Weisdorf et al. *Transplantation* 43:833–8 (1987); Lenssen et al. *JPEN J Parenter Enteral Nutr.* 11:112–8 (1987); Szeluga et al. *Cancer Res* 47:3300–16 (1987)). Glutamine-enriched parenteral nutrition was administered for an average of four weeks without significant clinical or biochemical side effects, confirming our previous Phase I trial in this patient population (Ziegler et al. *JPEN J Parenter Enteral Nutr.* 14(suppl):137S–46S (1990)).

Empiric administration of total parenteral nutrition has become routine in many centers; however, this trial is only the second randomized, blinded and controlled study evaluating parenteral nutrition in marrow transplant patients. Lenssen et al. provided similar protein and energy intakes with formulations containing either 23% or 45% of protein as branched-chain amino acids (Lenssen et al. *JPEN J Parenter Enteral Nutr.* 11:112–8 (1987)). No differences in clinical or nutritional indices were noted, while markedly negative nitrogen balance occurred in each patient group (Lenssen et al. *JPEN J Parenter Enteral Nutr.* 11:112–8 (1987)). The degree of nitrogen loss was similar to our control patients who received a comparable parenteral diet. Previous uncontrolled studies in similar patients demonstrate negative nitrogen balance despite infusion of conventional quantities of nutrients (Schmidt et al., *Exp Hematol* 8:506–11 (1980); Szeluga et al. *JPEN J Parenter Enteral Nutr* 9:139–43 (1985); Cheney et al. *Cancer* 59:1515–9 (1987); Cheney et al. *J Am Coll Nutr* 6:223–30 (1987); Lenssen et al. *JPEN J Parenter Enteral Nutr.* 11:112–8 (1987); and Reed et al. *Cancer* 51:1563–70 (1983)). The inability to achieve net nitrogen retention or even equilibrium with standard parenteral feeding in these severely stressed patients is comparable to observations in other critically ill patients (Streat et al. *J Trauma* 27:262–6 (1987)). In only one study was nitrogen equilibrium achieved in marrow transplant patients [the investigators provided large doses of nitrogen ($\approx 25$ g) and calories ($\approx 17000$ KJ/day)] (34). Such an approach does not represent the standard of care because of potential associated complications (e.g., azotemia, hepatic dysfunction and respiratory insufficiency) associated with overfeeding (Wilmore D. W., The Metabolic Management of the Critically Ill, 2nd edition. New York: Plenum Medical Book Company, 1980; Sheldon et al. *Arch Surg.* 113:504–8 (1978)). In our study, daily nitrogen losses in patients receiving glutamine supplementation averaged $\approx 2.8$ g less than observed in patients receiving standard parenteral feeding. The experimental diet resulted in nitrogen balances approaching equilibrium in the acute post-transplant period and thus appeared to exert improved protein-sparing effects compared to formulations previously utilized. As food intake was minimal, differences in nitrogen retention appear to be related to differences in the administered parenteral nutrient formulation, the major difference being the presence or absence of glutamine. However, the formulas did differ in the concentrations of several other amino acids. For example, the experimental formula contained ≈30% less total essential amino acids, which should favor protein utilization efficiency in the control group. It is unlikely that the reduction in commonly infused nonessential amino acids in the glutamine-enriched formula contributed to the effects observed.

Nitrogen balance was also determined between days 18 and 25 in 6 control and 5 glutamine-treated patients not receiving corticosteroids. Balance was neutral and not significantly different between groups. This improvement in balance with time in the controls is similar to previous studies in marrow transplant patients (Cheney et al. *J Am Coll Nutr* 6:223-30 (1987)). The clinical significance of attenuated protein-catabolic responses during the acute phase post-transplant in glutamine-supplemented patients is unclear. The difference in cumulative nitrogen balance of ~20 g represents ~0.5 kg of protein-rich tissue during this 7-period (Wilmore D. W., The Metabolic Management of the Critically Ill, 2nd edition. New York: Plenum Medical Book Company, 1980). Body protein loss may be associated with some loss of functional capacity (Wilmore D. W., The Metabolic management of the Critically Ill, 2nd edition. New York: Plenum Medical Book Company, 1980; Scrimshaw et al., *Am J Med Sci.* 237:367-403 (1973); and Wilmore et al. Injured man: Trauma and sepsis. In: Winters R. W., ed. Nutritional Support of the Seriously Ill Patient. New York: Academic Press, pp. 33-52 (1983)), however, glutamine may have improved clinical outcomes because of specific effects on other tissues (e.g. immunologic tissue: Kafkewitz et al. *Am J Clin Nutr* 37:1025-30 (1983); Ardawi MSM, *Metabolism* 37:99-103 (1988); Parry-Billings et al. *Lancet* 336:523-5 (1990); and Burke et al. *Arch Surg* 124:1396-9 (1989)), in addition to effects on protein metabolism.

The metabolic effects documented in this study are consistent with previous animal (O'Dwyer et al. *Clin Res* 35:369A (1987); Fox et al. *JPEN J Parenter Enteral Nutr.* 12:325-31 (1988); O'Dwyer et al. *JPEN J Parenter Enteral Nutr.* 13:579-85 (1989)) and human studies (Stehle et al. *Lancet* i:231-23 (1989); Hammarqvist et al. *Ann Surg* 209:455-61 (1989)). In stable postoperative patients, glutamine administration maintained skeletal muscle glutamine levels (Stehle et al. *Lancet* i:231-23 (1989); Hammarqvist et al. *Ann Surg* 209:455-61 (1989)) and skeletal muscle protein synthesis (Hammarqvist et al. *Ann Surg* 209:455-61 (1989)). In rats, intracellular glutamine concentrations in skeletal muscle were positively correlated with protein synthetic rates (Jepson et al. *Am J Physiol* 255:E166-72 (1988)). In this study, the reduced excretion ratio of 3-methylhistidine/creatinine suggests a reduction in total protein breakdown (Sjolin et al. *Am J Clin Nutr.* 49:62-70 (1989)), consistent with data in perfused rat skeletal muscle (MacLennan et al. *FEBS Lett* 237:133-36 (1988)). A portion of the improved nitrogen balance (~25%) may represent a relative increase in the free glutamine pool within skeletal muscle (e.g., nonprotein nitrogen balance) (Walser M., *Am J Clin Nutr.* 53:1337-8 (1991)); however, muscle biopsies to directly measure intracellular glutamine concentrations are necessary to confirm these estimates.

A significant reduction in clinically evident foci of infection and microbial colonization rates was observed in the glutamine-supplemented patients. The average number of cultures obtained per patient was comparable in both groups (19.3 compared to 19.0) and the period of observation for microbial colonization (time until recontamination) was also similar. The differences in infection/colonization are not explained by factors known to increase the risk of infection in bone marrow transplant patients as the two groups were well-matched for age, underlying disease, pre-transplant nutritional status, conditioning regimen, graft-versus-host disease prophylaxis regimen, and donor mismatches (Meyers J. D., In: Mandell G. L., Douglas R. G., Bennett J. E. (ed): Principles and Practice of Infectious Diseases, 3rd edition. New York: Churchill Livingstone; 2291-4 (1991); Pirsch et al. *Ann Int Med.* 104:619-31 (1986); and Meyers J. D., *Semin Oncol* 6(suppl):10-3 (1990)). A similar number of patients in each group developed acute graft-versus-host disease and received corticosteroids and human immunoglobulin (Sullivan et al. *N Engl J Med* 323:705-12 (1990)). Finally, no differences in mean serial leukocyte counts, time until neutrophil engraftment or antibiotic administration occurred between groups. Because these important factors involved in infectious complications were similar between groups, administration of the glutamine-supplemented solution appears to be the major factor responsible for the differences in incidence of infection.

The mechanisms responsible for the reduction in clinical infection and colonization are unclear. However, glutamine may alter function of circulating or fixed immune cells (Kafkewitz et al. *Am J Clin Nutr* 37:1025-30 (1983); Ardawi M. S. M., *Metabolism* 37:99-103 (1988); Parry-Billings et al. *Lancet* 336:523-5 (1990); and Burke et al. *Arch Surg* 124:1396-9 (1989)), may facilitate repair of mucosal barrier defenses (e.g., of the gastrointestinal tract [Windmueller H. G., *Adv Enzymol* 53:201-37 (1982); Newsholme et al. *Nutrition* 4:261-68 (1988); O'Dwyer et al. *Clin Res* 35:369A (1987); Klimberg et al. *Cancer* 66:62-8 (1990); Fox et al. *JPEN J Parenter Enteral Nutr.* 12:325-31 (1988); and Fox et al. *JPEN J Parenter Enteral Nutr.* 12(suppl):8S (1987)) or may maintain tissue antioxidant stores (Hong et al. *Surg Forum* 16:9-11 (1990)). Risk of infection is also influenced by nutritional status (Wilmore DW, The Metabolic Management of the Critically Ill, 2nd edition. New York: Plenum Medical Book Company, 1980; Scrimshaw et al., *Am J Med Sci.* 237:367-403 (1973)) and the reduced protein-catabolic responses may directly or indirectly improve resistance to infection or microbial clearance. These or other mechanisms must have accounted for the difference in infection and microbial colonization. Further study is required to define the precise mechanisms involved.

Overall, *Candida albicans* and coagulase negative *staphylococci* were the most common organisms isolated, and all of the bacteremias were caused by coagulase-negative *staphylococci*. The predominance of these organisms is consistent with previous studies in marrow transplant patients (Meyers J. D., In: Mandell G. L., Douglas R. G., Bennett J. E. (ed): Principles and Practice of Infectious Diseases, 3rd edition. New York: Churchill Livingstone; PP.2291-4 (1991); Pirsch et al. *Ann Int Med.* 104:619-31 (1986); Meyers J. D., *Semin Oncol* 6(suppl):10-3 (1990); Peterson et al. *JPEN J Parenter Enteral Nutr.* 10:58-62 (1986)) and is similar to previous patterns of colonization in this unit. Although the clinical importance of microbial colonization in our patients is unclear, previous studies suggest that surveillance cultures in neutropenic patients may predict subsequent infection (Cohen et al. *J Infect Dis* 147:789–93 (1983)). Five bacteremias were diagnosed in the entire study group (11%), however, four of these occurred in individuals receiving standard parenteral nutrition. Our overall rate of bacteremia is similar to a previous study of patients receiving total parenteral studied during a similar period after transplantation (Szeluga et al. *Cancer Res* 47:3300–16 (1987)).

Antibiotic administration was similar between groups despite reduced microbial colonization and infection. This may relate to the similar incidence of fever and duration of neutropenia in the groups; antibiotics were commonly administered following febrile episodes which may have been unrelated to infection (e.g. fever related to graft-versus-host disease). Once started, antibiotics were usually continued until neutrophil recovery. Recent studies evaluating the administration of granulocyte or granulocyte-macrophage colony stimulating factors in autologous bone marrow transplant patients (Rabinowe et al. *Blood* 76(suppl 1):167a (1990); and Nemunaitis et al. *N Engl J Med* 324:1773–8 (1991)) or in patients receiving chemotherapy (Crawford et al. *N Engl J Med* 325:164–70 (1991) have demonstrated accelerated neutrophil recovery which is associated with reduced use of antibiotics. A reduced incidence of infection (Nemunaitis et al. *N Engl J Med* 324:1773–8 (1991); Crawford et al. *N Engl J Med* 325:164–70 (1991)) occurred in some but not all studies (Rabinowe et al. *Blood* 76(suppl 1):167a (1990)), while hospital stay was reduced despite variable effects on febrile episodes (Rabinowe et al. *Blood* 76(suppl 1):167a (1990); Nemunaitis et al. *N Engl J Med* 324:1773–8 (1991); and Crawford et al. *N Engl J Med* 325:164–70 (1991)). Colony stimulating factors are felt to exert beneficial effects by enhancing granulocyte recovery and possibly cell function. Because glutamine-enriched nutrition and colony stimulating factors may exert effects by different mechanisms, studies evaluating possible additive or synergistic effects of these adjunctive therapies would be of interest.

The causes of the decreased length of hospital stay in this study are unclear at present. Because antibiotic requirements, time until marrow engraftment and the incidence of fever and graft-versus-host disease were similar between groups, this result may relate to other factors which could influence physician decision-making, including improved patient appetite or sense of well-being, in addition to the observed effects on nutritional status and infection rates. Further studies are in progress to evaluate the effect of glutamine supplementation on these endpoints.

In summary, this blinded, controlled trial suggests that glutamine-supplemented parenteral nutrition significantly reduces hospital morbidity following allogeneic bone marrow transplantation compared to results with standard, glutamine-free parenteral feeding. Larger, multicenter, controlled clinical trials appear indicated to determine the potential efficacy of glutamine-supplemented nutrition as adjunctive therapy in catabolic patients.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

TABLE 21

| Patient Characteristics at Study Entry | | |
|---|---|---|
| | (Mean ± SD or range) | |
| | Standard TPN | Glutamine-supplemented TPN |
| N | 21 | 24 |
| Sex: F | 13 | 16 |
| Age (yr) | 32.1 | 35.5 |
| | (20–48) | (20–49) |
| Weight (kg) | 68.6 | 67.2 |
| | (53.0–103.5) | (47.2–95.4) |
| % Ideal Body Weight (%) | 115 ± 22 | 108 ± 11 |
| Body Surface Area (m²) | 1.75 | 1.74 |
| | (1.54–2.12) | (1.42–2.12) |
| Triceps Skinfold Thickness (mm) | 19.8 ± 9.9 | 17.9 ± 6.4 |
| Midarm Muscle Circumference (cm) | 24.4 ± 2.5 | 24.8 ± 4.0 |
| Serum Albumin (g/L) | 34 ± 5 | 34 ± 5 |
| Diagnosis | | |
| AML | 9 | 11 |
| CML | 10 | 11 |
| ALL | 1 | 1 |
| Myelodysplasia | 0 | 1 |
| Hodgkin's Lymphoma | 1 | 0 |
| Donors other than matched siblings* | 4 | 5 |

AML = Acute myeloid leukemia; CML = Chronic myeloid leukemia; ALL = Acute lymphoblastic leukemia
*Single antigen mismatched, unrelated donor, or matched parental donor

TABLE 22

| Composition of amino acid formulas | | |
|---|---|---|
| Amino Acid (mg/100 ml) | Standard Formula | Glutamine-Supplemented Formula |
| LEUCINE | 790 | 324 |
| ISOLEUCINE | 570 | 270 |
| VALINE | 730 | 443 |
| METHIONINE | 570 | 270 |
| LYSINE | 900 | 243 |
| THREONINE | 570 | 205 |
| PHENYLALANINE | 790 | 265 |
| TRYPTOPHAN | 190 | 86 |
| HISTIDINE | 680 | 227 |
| ARGININE | 1120 | 340 |
| PROLINE | 680 | 189 |
| ALANINE | 1650 | 302 |
| GLYCINE | 790 | 162 |
| SERINE | 450 | 162 |
| TYROSINE | 30 | 22 |
| ASPARTATE | 330 | 0 |
| GLUTAMATE | 570 | 0 |
| GLUTAMINE | 0 | 2727 |
| total mg/100 ml | 11410 | 6237 |
| % Amino Acid/100 ml | 11.4% | 6.24% |

Novamine ® (Kabi Vitrum, Stockholm Sweden)
Renamine ® base amino acid solution (Baxter Health Care Corp., McGaw Park, IL).
To compare amino acid composition of isonitrogenous formulas, multiply figures in the glutamine-supplemented formula by 1.827.

TABLE 23

| Nutrient Intake Data | | |
|---|---|---|
| | Mean ± S.E.M. | |
| | Standard TPN | Gln-Supplemented TPN |
| Entire TPN Course | | |
| N | 21 | 24 |

TABLE 23-continued

Nutrient Intake Data

|  | Mean ± S.E.M. | |
| --- | --- | --- |
|  | Standard TPN | Gln-Supplemented TPN |
| Duration of TPN (days) | 28 ± 1 | 26 ± 2 |
| IV calories (kJ/day) | 9783 ± 232 | 9523 ± 221 |
| IV nitrogen (g/day) | 13.9 ± 0.3 | 14.4 ± 0.5 |
| Oral calories (kJ/day) | 1381 ± 132 | 1391 ± 174 |
| Oral nitrogen (g/day) | 1.3 ± 0.2 | 1.3 ± 0.2 |
| Initial 7 day Balance Period | | |
| N | 11 | 12 |
| IV calories (kJ/day) | 10682 ± 318 | 10334 ± 410 |
| IV nitrogen (g/day) | 14.9 ± 0.6 | 15.9 ± 0.7 |
| Oral calories (kJ/day) | 640 ± 79 | 774 ± 172 |
| Oral nitrogen (g/day) | 0.4 ± 0.2 | 0.3 ± 0.2 |
| Nitrogen balance (g/day) | −4.2 ± 1.2 | −1.4 ± 0.5§ |
| Cumulative nitrogen balance (g/7 days) | −29.6 ± 8.6 | −9.7 ± 3.4§ |
| 3-methylhistidine/ crreatinine ratio (mol/mol × 10³) | 13.3 ± 0.9 | 10.9 ± 4 ‖ |

§ P = 0.002
‖ P = 0.03

TABLE 24

Outcome Variables Following Transplantation
(Mean ± S.E.M. or number of patients)

| N | Standard TPN 21 | Gln-Supplemented 24 |
| --- | --- | --- |
| Average daily maximal temperature (°C.) | 37.7 ± 0.1 | 37.6 ± 0.1 |
| Cumulative mucositis score | 2.2 ± 0.5 | 2.1 ± 0.4 |
| Total days on antibiotics | 15 ± 2 | 13 ± 2 |
| Total antibiotic days | 44 ± 8 | 39 ± 7 |
| Patients receiving amphotericin B | 10 | 12 |
| Patients with AGVHD | 10 | 11 |
| Grade 1 | 4 | 6 |
| 2 | 5 | 5 |
| 3 | 1 | 0 |
| Patients receiving corticosteroids | 6 | 10 |
| Blood transfusions (total units) | 7 ± 1 | 7 ± 1 |
| Platelet transfusions (total units) | 9 ± 1 | 9 ± 1 |
| Days until average neutrophil count ≥ 0.5 × 10⁹/l (days) | 18 ± 1 | 20 ± 1 |
| Days until recontamination | 25 ± 2 | 25 ± 1 |
| Patients with no positive cultures | 1 | 10** |
| Patients with positive stool cultures | 16 | 10 |
| Patients with positive throat cultures | 18 | 13 |
| Patients with clinical infections | 9 | 3§§ |
| Length of stay post-transplant (days) | 36 ± 2 | 29 ± 1 ‖ ‖ | mucositis graded on 0–5 scale
**P = 0.005
P = 0.034
P = 0.0
§§ P = 0.041
‖ ‖ P = 0.017

What is claimed is:

1. A method for reducing the rate of infection by a pathogenic microorganism, which comprises administering to an animal in need of such a treatment a therapeutically effective amount GLN in an amount greater than that present in the normal diet of said animal.

2. The method of claim 1 wherein said parenteral administration is at the rate of 0.2 to 3 0 grams per kilogram of body weight per day of GLN.

3. The method of claim 2 wherein said parenteral administration is at the rate of 0.3 to 2.5 grams per kilogram of body weight per day of GLN.

4. The method of claim 3 wherein said parenteral administration is at the rate of 0.4 to 2.0 grams per kilograms of body weight per day of GLN.

5. The method accordingly to claim 3 wherein said pathogenic microorganisms is selected from the group consisting of *Candida albicans*, Staphylococcus sp., Aspergillus sp. and *E. coli*.

* * * * *